United States Patent
Long et al.

(10) Patent No.: US 10,947,229 B2
(45) Date of Patent: Mar. 16, 2021

(54) DIMETHYL AMINO AZETIDINE AMIDES AS JAK INHIBITORS

(71) Applicant: THERAVANCE BIOPHARMA R&D IP, LLC, South San Francisco, CA (US)

(72) Inventors: Daniel D. Long, South San Francisco, CA (US); Cameron Smith, South San Francisco, CA (US); Corbin Thompson, South San Francisco, CA (US)

(73) Assignee: Theravance Biopharma R&D IP, LLC, South San Francisco, CA (US)

(*) Notice: Subject to any disclaimer, the term of this patent is extended or adjusted under 35 U.S.C. 154(b) by 0 days.

(21) Appl. No.: 16/559,077

(22) Filed: Sep. 3, 2019

(65) Prior Publication Data

US 2020/0071323 A1 Mar. 5, 2020

Related U.S. Application Data

(60) Provisional application No. 62/726,562, filed on Sep. 4, 2018.

(51) Int. Cl.
*C07D 471/04* (2006.01)

(52) U.S. Cl.
CPC ................ *C07D 471/04* (2013.01)

(58) Field of Classification Search
CPC ................................................ C07D 471/04
See application file for complete search history.

(56) References Cited

U.S. PATENT DOCUMENTS

| | | |
|---|---|---|
| 6,534,524 B1 | 3/2003 | Kania et al. |
| 6,884,890 B2 | 4/2005 | Kania et al. |
| 7,884,109 B2 | 2/2011 | Ohlmeyer et al. |
| 8,450,340 B2 | 5/2013 | Hood et al. |
| 8,575,336 B2 | 11/2013 | Coe et al. |
| 8,648,069 B2 | 2/2014 | Akritopoulou-Zanze |
| 8,895,544 B2 | 11/2014 | Coe et al. |
| 10,100,049 B2 | 10/2018 | Fatheree et al. |
| 10,183,942 B2 | 1/2019 | Fatheree et al. |
| 10,196,393 B2 | 2/2019 | Fatheree et al. |
| 10,208,040 B2 | 2/2019 | Fatheree et al. |
| 10,251,874 B2 | 4/2019 | Dabros et al. |
| 10,392,386 B2 | 8/2019 | Fatheree et al. |
| 10,406,148 B2 | 9/2019 | Thalladi et al. |
| 10,493,077 B2 | 12/2019 | Fatheree et al. |
| 10,519,153 B2 | 12/2019 | Fatheree et al. |
| 10,526,330 B2 | 1/2020 | Fatheree et al. |
| 10,548,886 B2 | 2/2020 | Thalladi et al. |
| 10,550,118 B2 | 2/2020 | Fatheree et al. |
| 2005/0090529 A1 | 4/2005 | McAlpine et al. |
| 2015/0158864 A1 | 6/2015 | Thorarensen et al. |
| 2015/0329542 A1 | 11/2015 | Coe et al. |
| 2016/0289196 A1 | 10/2016 | Choi et al. |
| 2017/0121327 A1 | 5/2017 | Fatheree et al. |
| 2018/0258088 A1 | 9/2018 | Fatheree et al. |
| 2018/0311223 A1 | 11/2018 | Dabros et al. |
| 2018/0311226 A1 | 11/2018 | Thalladi et al. |
| 2018/0311255 A1 | 11/2018 | Fatheree et al. |
| 2019/0119275 A1 | 4/2019 | Fatheree et al. |
| 2019/0127371 A1 | 5/2019 | Fatheree et al. |
| 2020/0046719 A1 | 2/2020 | Fatheree et al. |
| 2020/0071324 A1 | 3/2020 | Colson et al. |
| 2020/0071325 A1 | 3/2020 | Long et al. |
| 2020/0087303 A1 | 3/2020 | Fatheree et al. |
| 2020/0121669 A1 | 4/2020 | Thalladi et al. |
| 2020/0131178 A1 | 4/2020 | Fatheree et al. |
| 2020/0181141 A1 | 6/2020 | Fatheree et al. |

FOREIGN PATENT DOCUMENTS

| | | |
|---|---|---|
| CN | 112279848 A | 1/2021 |
| JP | 2010111624 A | 5/2010 |
| WO | WO 2005/009389 A2 | 2/2005 |
| WO | WO 2010/114971 A1 | 10/2010 |
| WO | WO 2013/014567 A1 | 1/2013 |
| WO | WO 2015/173683 A1 | 11/2015 |

(Continued)

OTHER PUBLICATIONS

U.S. Appl. No. 16/701,426, Unpubliished, Fatheree et al.
Wilcken et al., "Principles and applications of halogen bonding in medicinal chemistry and chemical biology", Journal of Medicinal Chemistry, 56: 1363-1388 (2013).
International Search Report and the Written Opinion for PCT/US2019/049276 dated Oct. 28, 2019.
Gontcharov et al., "Development of a scalable synthesis for an inhaled pan-JAK inhibitor", Organic Process Research & Development 2019, XXX, XXX-XXX (published online).
Tanaka et al., "New insight into mechanisms of pruritus from molecular studies on familial primary localized cutaneous amyloidosis", British Journal of Dermatology, 161: 1217-1224 (2009).

(Continued)

*Primary Examiner* — John S Kenyon
(74) *Attorney, Agent, or Firm* — Jeffrey A. Hagenah; Florence Jovic

(57) ABSTRACT

The invention provides compounds of formula (I):

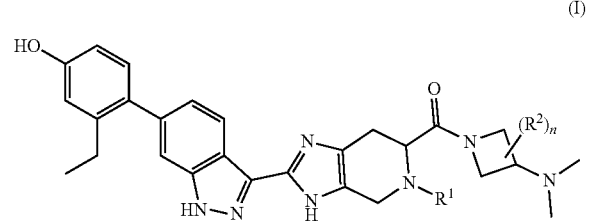

(I)

where the variables are defined in the specification, or a pharmaceutically-acceptable salt thereof, that are useful as JAK kinase inhibitors. The invention also provides pharmaceutical compositions comprising such compounds and methods of using such compounds to treat respiratory diseases.

15 Claims, No Drawings

(56) References Cited

FOREIGN PATENT DOCUMENTS

| WO | WO 2016/026078 A1 | 2/2016 | |
|---|---|---|---|
| WO | WO 2017/077283 A1 | 5/2017 | |
| WO | WO 2017/077288 A1 | 5/2017 | |
| WO | 2018165329 A1 | 9/2018 | |
| WO | WO-2018165392 A1 * | 9/2018 | ............. A61P 11/06 |
| WO | 2020/173400 A1 | 9/2020 | |
| WO | 2020/181034 A1 | 9/2020 | |

OTHER PUBLICATIONS

Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19: 908-911 (2009).

Vincenti et al., "Randomized phase 2b trial of tofacitinib (CP-690,550) in de novo kidney transplant patients: Efficacy, renal function and safety at 1 year", American Journal of Transplantation, 12: 2446-2456 (2012).

Ward et al., "Enantiomeric disposition of inhaled, intravenous and oral racemic-salbutamol in man—no evidence of enantioselective lung metabolish", J Clin Pharmacol, 49:15-22 (2000).

Weinbrand-Goichberg et al., "Eosinophilic esophagitis: an immune-mediated esophageal disease", Immunol Res, 56: 249-260 (2013).

Welz-Kubiak et al., "IL-31 is overexpressed in lichen planus but its level does not correlate with pruritus severity", Journal of Immunology Research, Article 854747, 6 pages (2015).

Woywodt et al., "Mucosal cytokine expression, cellular markers and adhesion molecules in inflammatory bowel disease", European Journal of Gastroenterology & Hepatology, 11: 267-276 (1999).

Xing et al., "Alopecia areata is driven by cytotoxic T lymphocytes and is reversed by JAK inhibition", Nature Medicine, 20(9): 1043-1049 (Sep. 2014).

Yamamoto et al., "Mucosal inflammation in the terminal ileum of ulcerative colitis patients: Endoscopic findings and cytokine profiles", Digestive and Liver Disease, 40: 253-259 (2008).

Yan et al., "Discovery of 3-(5'-Substituted)-benzimidazol-5-(1-(3,5-dichloropyridin-4-yl)ethoxy)-1H-indazoles as potent fibroblast growth factor receptor inhibitors: Design, synthesis, and biological evaluation", J. Med. Chem., 59: 6690-6708 (2016).

Yano et al., "Ipilimumab augments antitumor activity of bispecific antibody-armed T cells", Journal of Translational Medicine, 12: 191 (2014).

Zeiser et al., "Ruxolitinib in corticosteroid-refractory graft-versus-host disease after allogeneic stem cell transplantation: a multi-center survey", Leukemia, 29(10): 2062-2068 (Oct. 2015).

Zhou et al., "Cytokines and Behcet's Disease", Autoimmunity Reviews, 11: 699-704 (2012).

U.S. Appl. No. 62/751,967, Unpubliished, Fatheree et al.

U.S. Appl. No. 16/511,410, Unpubliished, Fatheree et al.

Abcouwer, "Angiogenic factors and cytokines in diabetic retinopathy", J Clin Cell Immunol, Supplement 1: 1-12 (2013).

Bao et al., "The involvement of the JAK-STAT signaling pathway in chronic inflammatory skin disease atopic dermatitis", JAK-STAT, 2(3): e24137-1-e24137-8 (2013). (1997).

Berastegui et al., "BALF cytokines in different phenotypes of chronic lung allograft dysfunction in lung transplant patients", Clinical Transplantation, 31: e12898 (2017).

Coghill et al., "Effector CD4+ T cells, the cytokines they generate, and GVHD: something old and something new", Blood, 117(12): 3268-3276 (Mar. 24, 2011).

Cottin, "Eosinophilic lung diseases", Clin Chest Med, 37: 535-556 (2016).

Craiglow et al., "Tofacitinib citrate for the treatment of vitiligo: A pathogenesis-directed therapy", JAMA Dermatology, 151: 1110-1112 (2015).

De La Torre et al., "Salbutamol metabolism how to differentiate oral vs. inhaled administrations: looking outside the box", World Anti-doping Agency (Nov. 20, 2015).

De Nitto et al., "Involvement of interleukin-15 and interleukin-21, two gamma-chain-related cytokines, in celiac disease", World J Gastroenterol, 15(37): 4609-4614 (Oct. 7, 2009).

Duffel et al., "On the mechanism of aryl sulfotransferase", J Biological Chemistry, 256(21):11123-11127 (1981).

Eaton et al., "Stereoselective sulphate conjugation of salbutamol by human lung and bronchial epithelial cells", Br J Clin Pharmacol, 41:201-206 (1996).

El-Hashemite et al., "Interferon-gamma-Jak-Stat signaling in pulmonary lymphangioleiomyomatosis and renal angiomyolipoma", Am J Respir Cell Mol Biol, 33: 227-230 (2005).

El-Hashemite et al., "Perturbed IFN-gamma-Jak-signal transducers and activators of transcription signaling in tuberous sclerosis mouse models: Synergistic effects of rapamycin-IFN-gamma treatment", Cancer Research, 64: 3436-3443 (May 15, 2004).

Fang et al., "Interleukin-6-572C/G polymorphism is associated with serum interleukin-6 levels and risk of idiopathic pulmonary arterial hypertension", Journal of the American Society of Hypertension, 11(3): 171-177 (2017).

Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).

Fenwick et al., "Effect of JAK inhibitors on release of CXCL9, CXCL10 and CXCL11 from human airway epithelial cells", PLOS One, 10(6): e0128757 (2015).

Foloppe et al., "Identification of a buried pocket for potent and selective inhibition of Chk1: Prediction and verification", Bioorganic & Medicinal Chemistry, 14: 1792-1804 (2006).

Funatsu et al., "Association of vitreous inflammatory factors with diabetic macular edema", Ophthalmology, 116: 73-79 (2009).

Gauthier et al., "Update on chronic lung allograft dysfunction", Curr Transplant Rep, 3(3): 185-191 (Sep. 2016).

Horai et al, "Cytokines in autoimmune uveitis", Journal of Interferon & Cytokine Research, 31(10): 733-744 (2011).

Huang et al., "Glycoprotein 130 inhibitor ameliorates monocrotalline-induced pulmonary hypertension in rats", Canadian Journal of Cardiology, 32: 1356.e1-1356.e10 (2016).

Jones et al., "Design and synthesis of a Pan-Janus kinase inhibitor clinical candidate (PF-06263276) suitable for inhaled and topical delivery for the treatment of inflammatory diseases of the lungs and skin", J. Med. Chem., 60: 767-786 (2017).

Knickelbein et al., "Inflammatory mechanisms of age-related macular degeneration", International Ophthalmology Clinics, 55(3): 63-78 (2015).

Kudlacz et al., "The JAK-3 inhibitor CP-690550 is a potent anti-inflammatory agent in a murine model of pulmonary eosinophilia", European Journal of Pharmacology, 582: 154-161 (2008).

Kumawat et al., "Microscopic colitis patients demonstrate a mixed Th17/Tc17 and Th1/Tc1 mucosal cytokine profile", Molecular Immunology, 55: 355-364 (2013).

Malaviya et al., "Janus Kinase-3 dependent inflammatory responses in allergic asthma", International Immunopharmacology, 10: 829-836 (2010).

Matsunaga et al., "Effects of a Janus kinase inhibitor, pyridone 6, on airway responses in a murine model of asthma", Biochemical and Biophysical Research Communications, 404: 261-267 (2011).

McBride et al., "Design and structure-activity relationship of 3-benzimidazol-2-yl-1H-indazoles as inhibitors of receptor tyrosine kinases", Bioorganic & Medicinal Chemistry Letters, 16: 3595-3599 (2006).

McBride et al., "3-Benzimidazol-2-yl-1H-indazoles as potent c-ABL inhibitors", Bioorganic & Medicinal Chemistry Letters, 16: 3789-3792 (2006).and renal angiomyolipoma, Am J Respir Cell Mol Biol, 33: 227-230 (2005).

Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).

Okiyama et al., "Reversal of CD8 T-cell-mediated mucocutaneous graft-versus-host-like disease by the JAK inhibitor tofacitinib", Journal of Investigative Dermatology, 134: 992-1000 (2014).

(56) References Cited

OTHER PUBLICATIONS

Owen et al., "Soluble mediators of diabetic macular edema: The diagnostic role of aqueous VEGF and cytokine levels in diabetic macular edema", Curr Diab Rep, 13(4): 476-480 (Aug. 2013).
Reimund et al., "Mucosal inflammatory cytokine production by intestinal biopsies in patients with ulcerative colitis and Crohn's disease", Journal of Clinical Immunology, 16(3): 144-150 (1996).
Sharan et al., "Pulmonary metabolism of resveratrol: in vitro and in vivo evidence", Drug Metab Dispos, 41:1163-1169 (May 2013).
Shino et al., "The prognostic importance of CXCR3 chemokine during organizing pneumonia on the risk of chronic lung allograft dysfunction after lung transplantation", PLOS One, 12(7): e0180281 (2017).
Simov et al., "Structure-based design and development of (benz)imidazole pyridones as JAK1-selective kinase inhibitors", Bioorganic & Medicinal Chemistry Letters, 26: 1803-1808 (2016).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
Wilcken et al., "Principles and applications of halogen bonding in medicinal chemistry and chemical biology", Journal of Med Chem, 56:1363-1388 (2013).

* cited by examiner

DIMETHYL AMINO AZETIDINE AMIDES AS JAK INHIBITORS

CROSS-REFERENCE TO RELATED APPLICATIONS

This application claims the benefit of U.S. Provisional Application No. 62/726,562, filed on Sep. 4, 2018, the disclosure of which is incorporated herein by reference in its entirety.

BACKGROUND OF THE INVENTION

Field of the Invention

The invention is directed to compounds useful as JAK kinase inhibitors. The invention is also directed to pharmaceutical compositions comprising such compounds and methods of using such compounds to treat respiratory diseases.

State of the Art

Asthma is a chronic disease of the airways for which there are no preventions or cures. The disease is characterized by inflammation, fibrosis, hyper-responsiveness, and remodeling of the airways, all of which contribute to airflow limitation. An estimated 300 million people worldwide suffer from asthma and it is estimated that the number of people with asthma will grow by more than 100 million by 2025. In the United States, asthma afflicts about 6% to 8% of the population, making it one of the most common chronic diseases in the country. Although most patients can achieve control of asthma symptoms with the use of inhaled corticosteroids that may be combined with a leukotriene modifier and/or a long acting beta agonist, there remains a subset of patients with severe asthma whose disease is not controlled by conventional therapies. Severe persistent asthma is defined as disease that remains uncontrolled on high doses of inhaled corticosteroids. While severe asthmatics are estimated to account for approximately 5% of all asthma sufferers, they have a high risk of morbidity and mortality and are responsible for a disproportionate share of health care resource utilization among asthmatics. There remains a need for novel therapies to treat these patients.

Cytokines are intercellular signaling molecules which include chemokines, interferons, interleukins, lymphokines, and tumor necrosis factor. Cytokines are critical for normal cell growth and immunoregulation but also drive immune-mediated diseases and contribute to the growth of malignant cells. Elevated levels of many cytokines have been implicated in the pathology of asthma inflammation. For example, antibody-based therapies targeted at interleukins (IL)-5, and 13 have been shown to provide clinical benefit in subsets of severe asthma patients. Among the cytokines implicated in asthma inflammation, many act through signaling pathways dependent upon the Janus family of tyrosine kinases (JAKs), which signal through the Signal Transducer and Activator of Transcription (STAT) family of transcription factors. Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF).

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings. Each of the four members of the JAK family is implicated in the signaling of at least one of the cytokines associated with asthma inflammation. Consequently, a chemical inhibitor with pan-activity against all members of the JAK family could modulate a broad range of pro-inflammatory pathways that contribute to severe asthma.

However, the broad anti-inflammatory effect of such inhibitors could suppress normal immune cell function, potentially leading to increased risk of infection. Evidence of increased infection risk has been observed with the JAK inhibitor tofacitinib, which is dosed orally for the treatment of rheumatoid arthritis. In asthma, inflammation is localized to the respiratory tract. Inflammation of the airways is characteristic of other respiratory diseases in addition to asthma. Chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and sarcoidosis are also respiratory tract diseases in which the pathophysiology is believed to be related to JAK-signaling cytokines. Local administration of a JAK inhibitor to the lungs by inhalation offers the potential to be therapeutically efficacious by delivering a potent anti-cytokine agent directly to the site of action, limiting systemic exposure and therefore limiting the potential for adverse systemic immunosuppression. The need remains for a potent JAK inhibitor suitable for local administration to the lungs for treatment of respiratory disease.

JAK-signaling cytokines also play a major role in the activation of T cells, a sub-type of immune cells that is central to many immune processes. Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipient's T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., *Curr. Transplant. Rep.*, 2016, 3(3), 185-191). CLAD is poorly responsive to treatment and therefore, there remains a need for effective compounds capable of preventing or treating this condition. Several JAK-dependent cytokines such as IFNγ and IL-5 are up-regulated in CLAD and lung transplant rejection (Berastegui et al, *Clin. Transplant.* 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, *PLOS One,* 2017, 12 (7), e0180281). Systemic JAK inhibition has been shown to be effective in kidney transplant rejection (Vicenti et al., *American Journal of Transplantation,* 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD) which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, *Leukemia,* 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD.

SUMMARY OF THE INVENTION

In one aspect, the invention provides novel compounds having activity as JAK kinase inhibitors.

Accordingly, the invention provides a compound of formula (I):

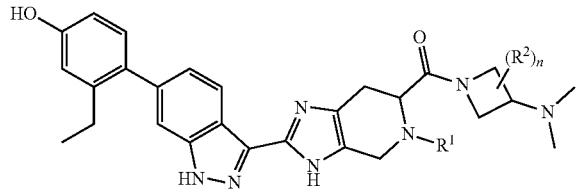

wherein:
n is 0, 1 or 2;
$R^1$ is $C_{1-3}$ alkyl; and
each $R^2$ is independently $C_{1-3}$ alkyl;
or a pharmaceutically-acceptable salt thereof.

The invention also provides a pharmaceutical composition comprising a compound of the invention and a pharmaceutically-acceptable carrier.

The invention also provides a method of treating respiratory disease, in particular, asthma and CLAD, in a mammal, the method comprising administering to the mammal a therapeutically effective amount of a compound, or of a pharmaceutical composition of the invention.

The invention also provides a compound of the invention as described herein for use in medical therapy, as well as the use of a compound of the invention in the manufacture of a formulation or medicament for treating respiratory disease in a mammal.

DETAILED DESCRIPTION OF THE INVENTION

In one aspect, the invention provides compounds having activity as a JAK kinase inhibitor. Accordingly, the invention provides a compound of formula (I):

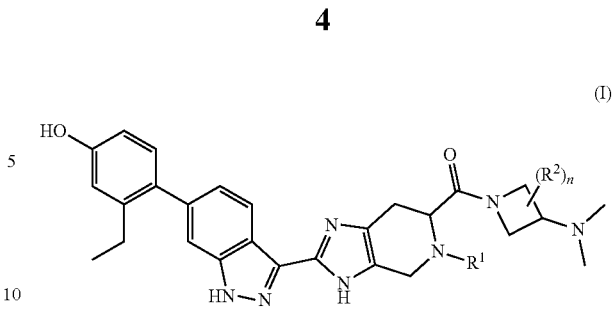

wherein:
n is 0, 1 or 2;
$R^1$ is $C_{1-3}$ alkyl; and
each $R^2$ is independently $C_{1-3}$ alkyl;
or a pharmaceutically-acceptable salt thereof.

In some embodiments, the compound has the formula (II):

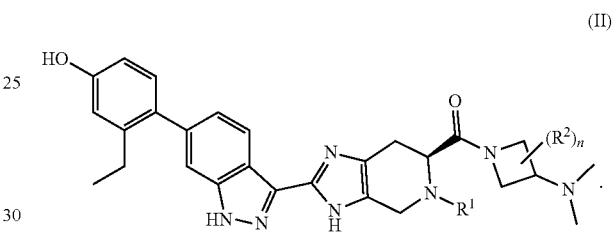

In some embodiments, the compound has the formula (III):

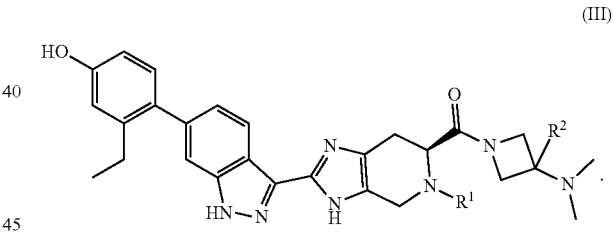

In some embodiments, $R^1$ is selected from the group consisting of ethyl, propyl, and isopropyl. In some embodiments, n is 0. In some embodiments, n n is 1. In some embodiments, n is 1 and $R^2$ is methyl.

In another embodiment, the invention provides a compound of formula 1:

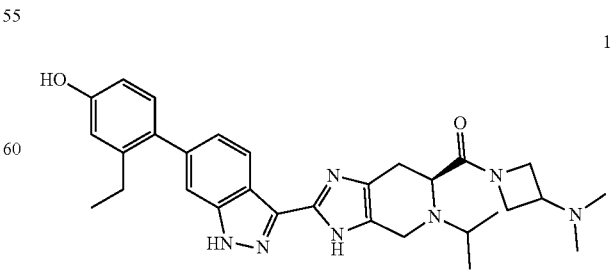

or a pharmaceutically-acceptable salt thereof.

In another embodiment, the invention provides a compound of formula 1:

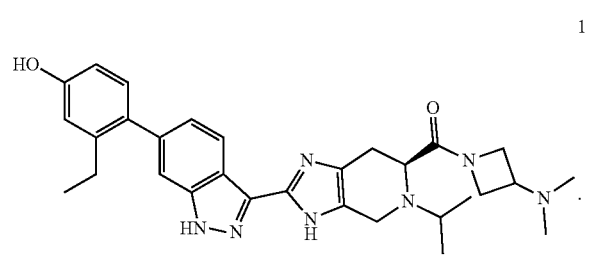 [SMILES: CCc1cc(O)ccc1-c1ccc2c(-c3nc4c([nH]3)CN(C(C)C)[C@H](C(=O)N3CC(N(C)C)C3)C4)n[nH]c2c1]
1

In another embodiment, the invention provides a compound of formula 2

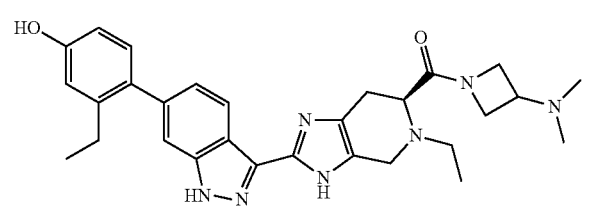
2 or a pharmaceutically-acceptable salt thereof.

In another embodiment, the invention provides a compound of formula 2

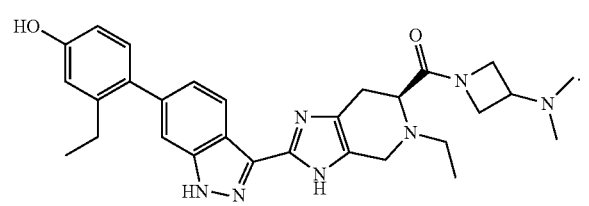
2

In another embodiment, the invention provides a compound of formula 3

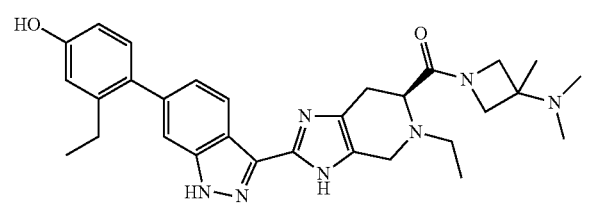
3 or a pharmaceutically-acceptable salt thereof.

In another embodiment, the invention provides a compound of formula 3

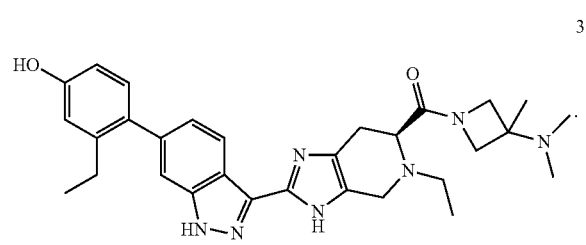 [SMILES: CCc1cc(O)ccc1-c1ccc2c(-c3nc4c([nH]3)CN(CC)[C@H](C(=O)N3CC(C)(N(C)C)C3)C4)n[nH]c2c1]
3

In another embodiment, the invention provides a compound of formula 4

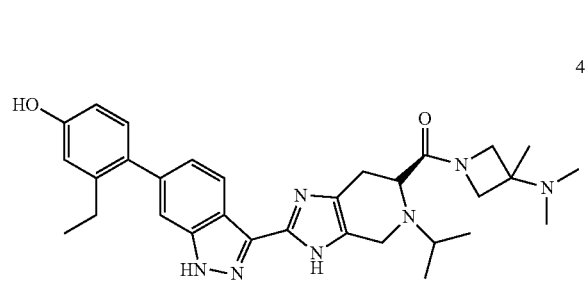
4 or a pharmaceutically-acceptable salt thereof.

In another embodiment, the invention provides a compound of formula 4

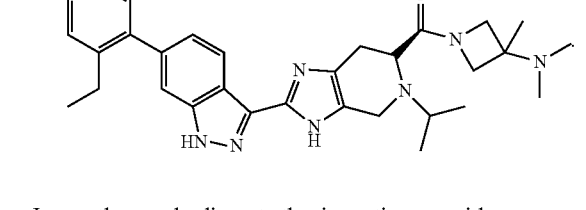
4

In another embodiment, the invention provides a compound of formula 5

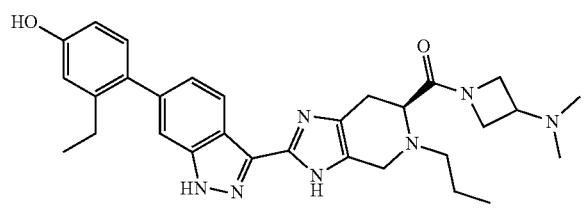
5 or a pharmaceutically-acceptable salt thereof.

In another embodiment, the invention provides a compound of formula 5

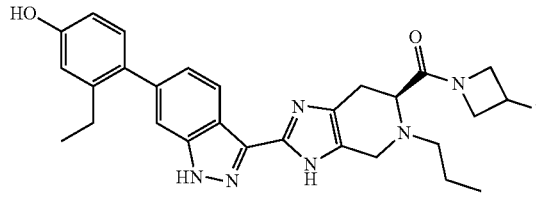

5

In another embodiment, the invention provides a compound of formula 6

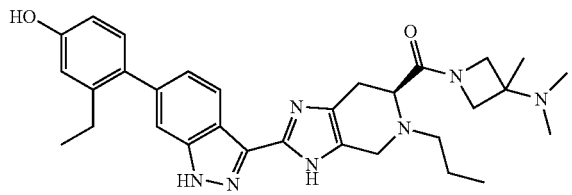

6 or a pharmaceutically-acceptable salt thereof.

In another embodiment, the invention provides a compound of formula 6

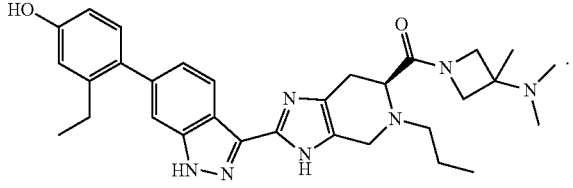

6

Chemical structures are named herein according to IUPAC conventions as implemented in ChemDraw software (PerkinElmer, Inc., Cambridge, Mass.). Compound 1 is designated as (S)-(3-(dimethylamino)azetidin-1-yl)(2-(6-(2-ethyl-4-hydroxyphenyl)-1H-indazol-3-yl)-5-isopropyl-4,5,6,7-tetrahydro-3H-imidazo[4,5-c]pyridin-6-yl)methanone.

Furthermore, the imidazo portion of the tetrahydroimidazopyridine moiety exists in tautomeric forms, illustrated below for a fragment of the compounds of the disclosure

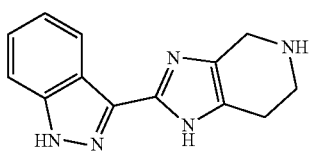

A

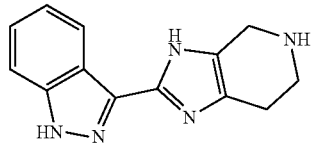

B

According to the IUPAC convention, these representations give rise to different numbering of the atoms of the imidazole portion: (1H-indazol-3-yl)-4,5,6,7-tetrahydro-1H-imidazo[4,5-c]pyridine (structure A) vs. (1H-indazol-3-yl)-4,5,6,7-tetrahydro-3H-imidazo[4,5-c]pyridine (structure B). It will be understood that although structures are shown, or named, in a particular form, the invention also includes the tautomer thereof.

The compounds of the disclosure may contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

The compounds of the disclosure may also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), (II) and (III), i.e., compounds of formula (I), (II) and (III) where one or more atom has been replaced or enriched with an atom having the same atomic number but an atomic mass different from the atomic mass that predominates in nature. Examples of isotopes that may be incorporated into a compound of formula (I), (II) and (III) include, but are not limited to, $^2H$, $^3H$, $^{11}C$, $^{13}C$, $^{14}C$, $^{13}N$, $^{15}N$, $^{15}O$, $^{17}O$, and $^{18}O$. Of particular interest are compounds of formula (I), (II) and (III) enriched in tritium or carbon-14, which compounds can be used, for example, in tissue distribution studies. Also of particular interest are compounds of formula (I), (II) and (III) enriched in deuterium especially at a site of metabolism, which compounds are expected to have greater metabolic stability. Additionally of particular interest are compounds of formula (I), (II) and (III) enriched in a positron emitting isotope, such as $^{11}C$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl (cBu), cyclopentyl, cyclohexyl, cycloheptyl, cyclooctyl, adamantyl, and the like.

The term "heterocyclyl", "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclyl groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "halo" means fluoro, chloro, bromo or iodo.

The term "therapeutically effective amount" means an amount sufficient to effect treatment when administered to a patient in need of treatment.

The term "treating" or "treatment" means preventing, ameliorating or suppressing the medical condition, disease or disorder being treated (e.g., a respiratory disease) in a patient (particularly a human); or alleviating the symptoms of the medical condition, disease or disorder.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), (II) or (III), i.e. a form where one or more amino groups have been protonated by an acid. Typically, the salt is a pharmaceutically acceptable salt, although this is not required for salts of intermediate compounds that are not intended for administration to a patient.

General Synthetic Procedures

Compounds of this invention, and intermediates thereof, can be prepared according to the following general methods and procedures using commercially-available or routinely-prepared starting materials and reagents. The substituents and variables (e.g., $R^1$, $R^2$, n, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

A general method of preparing final compounds of the invention is illustrated in the following Scheme.

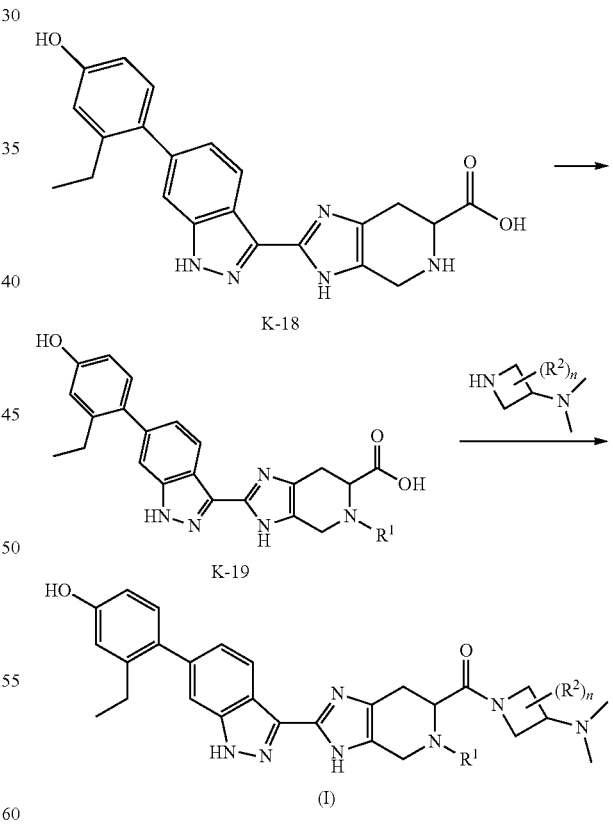

Compound K-18 is reacted with a ketone or aldehyde in the presence of a reducing agent to provide the compound of formula K-19. Compound K-19 is then reacted with a substituted azetidine under typical amide bond formation conditions to give compound (I). Typically, the carboxylic acid is contacted with between about 1 and about 4 equivalents of the substituted azetidine in the presence of an excess of base. The amide bond formation reaction may utilize coupling agents, such as N,N,N'N'-tetramethyl-O-(7-azabenzotriazol-1-yl)uronium hexafluorophosphate (HATU) or other amide coupling agents known in the art. Hydrazine can be added to cleave undesired byproducts. The reaction is typically conducted at room temperature for between about 5 minutes and about 24 hours or until the reaction is substantially complete.

Pharmaceutical Compositions

The compounds of the invention and pharmaceutically-acceptable salts thereof are typically used in the form of a pharmaceutical composition or formulation. Such pharmaceutical compositions may advantageously be administered to a patient by inhalation. In addition, pharmaceutical compositions may be administered by any acceptable route of administration including, but not limited to, oral, rectal, nasal, topical (including transdermal) and parenteral modes of administration.

Accordingly, in one of its compositions aspects, the invention is directed to a pharmaceutical composition comprising a pharmaceutically-acceptable carrier or excipient and a compound of formula (I), (II) or (III), where, as defined above, "compound of formula (I), (II) or (III)" means a compound of formula (I), (II) or (III) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formula (I) and pharmaceutically-acceptable salts thereof The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a compound of the invention in micronized form. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In another particular embodiment, the pharmaceutical composition is administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the invention; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another particular aspect, the pharmaceutical composition is administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 μg/mL to about 20 mg/mL of a compound of the invention and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat Softmist Inhalaler (Boehringer Ingelheim); the AERx Pulmonary Delivery System (Aradigm Corp.); the PART LC Plus Reusable Nebulizer (Pari GmbH); and the like.

In yet another aspect, the pharmaceutical compositions of the invention may alternatively be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form, the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the pharmaceutical compositions of the invention.

Alternative formulations may also include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present invention.

Dry Powder Composition

A micronized compound of formula (I) (1 g) is blended with milled lactose (25 g). This blended mixture is then loaded into individual blisters of a peelable blister pack in an amount sufficient to provide between about 0.1 mg to about 4 mg of the compound of formula (I) per dose. The contents of the blisters are administered using a dry powder inhaler.

Dry Powder Composition

A micronized compound of formula (I) (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound of formula (I) per dose.

Metered-Dose Inhaler Composition

A micronized compound of formula (I) (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 0.1 mg to about 4 mg of the compound of formula (I) per dose when administered by the metered dose inhaler.

Nebulizer Composition

A compound of formula (I) (25 mg) is dissolved in a solution containing 1.5-2.5 equivalents of hydrochloric acid, followed by addition of sodium hydroxide to adjust the pH to 3.5 to 5.5 and 3% by weight of glycerol. The solution is stirred well until all the components are dissolved. The solution is administered using a nebulizer device that provides about 0.1 mg to about 4 mg of the compound of formula (I) per dose.

Utility

The JAK inhibitors of the invention have been designed for the treatment of inflammatory and fibrotic disease of the respiratory tract. In particular, the compounds have been designed to enable delivery of a potent anti-cytokine agent directly to the site of action of respiratory disease in the lung while limiting systemic exposure.

The compounds of the invention have been shown to be potent inhibitors of the JAK family of enzymes: JAK1, JAK2, JAK3, and TYK2. In addition, compound 1-6 have demonstrated potent inhibition of pro-inflammatory and pro-fibrotic cytokines. It has been recognized that the broad anti-inflammatory effect of JAK inhibitors could suppress normal immune cell function, potentially leading to increased risk of infection. The present compounds have therefore been optimized to limit absorption from the lung into the plasma, thus minimizing the risk of immunosuppression.

As described in the experimental section below, the absorption and distribution of compounds 1-6 have been profiled in preclinical assays. Compounds 1-6 were tested in mice and showed at 5 hours post-dosing high concentration in lung tissue and low absorption into plasma. Compounds 1-6 have been shown to inhibit an effect of the pro-inflammatory cytokine IL-13 in mouse lung tissue. Specifically, the compounds have demonstrated inhibition of IL-13-induced phosphorylation of STAT6 in lung tissue which provides evidence of local lung JAK target engagement in vivo. This effect has been observed when the pro-inflammatory cytokine IL-13 is administered 4 hours after administration of the test compound, providing further evidence of significant retention in the lung.

Compounds 1-6 have been demonstrated to exhibit both potent inhibitory activity at the cellular level and significant retention in lung tissue. Extensive investigation by the present inventors has determined that while it is possible to identify compounds that are potent at the cellular level or compounds that show significant retention in the lung, it is far more difficult to discover compounds that exhibit both desirable characteristics at the same time.

The anti-inflammatory activity of JAK inhibitors has been robustly demonstrated in preclinical models of asthma (Malaviya et al., *Int. Immunopharmacol.*, 2010, 10, 829-836; Matsunaga et al., *Biochem. and Biophys. Res. Commun.*, 2011, 404, 261-267; Kudlacz et al., *Eur. J. Pharmacol*, 2008, 582, 154-161). Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF). Accordingly, the compounds of the invention are expected to be useful for the treatment of inflammatory respiratory disorders, in particular, asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, and sarcoidosis. The present compounds, therefore, are also expected to be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, and sarcoidosis.

When compared to their corresponding fluoro analog (compound C-1 to C-6), compounds 1-6 have been shown to have similar JAK activity. However, they have the advantage of giving rise to significantly less sulfation metabolism, as demonstrated in Assay 5. This is significant as sulfation metabolism occurs in the lungs, which could lead to a rapid decrease in exposure of the active parent compound.

Compounds 1-6 of the disclosure have demonstrated inhibition of cytokines associated with inflammation. Therefore, the compounds of the disclosure are likely to be useful for the treatment of certain specific respiratory diseases, as detailed below.

Eosinophilic airway inflammation is a characteristic feature of diseases collectively termed eosinophilic lung diseases (Cottin et al., *Clin. Chest. Med.*, 2016, 37(3), 535-56). Eosinophilic diseases have been associated with IL-4, IL-13 and IL-5 signaling. Eosinophilic lung diseases include infections (especially helminthic infections), drug-induced pneumonitis (induced for example by therapeutic drugs such as antibiotics, phenytoin, or l-tryptophan), fungal-induced pneumonitis (e.g. allergic bronchopulmonary aspergillosis), hypersensitivity pneumonitis and eosinophilic granulomatosis with polyangiitis (formerly known as Churg-Strauss syndrome). Eosinophilic lung diseases of unknown etiology include idiopathic acute eosinophilic pneumoni, idiopathic chronic eosinophilic pneumonia, hypereosinophilic syndrome, and Löffler syndrome.

A polymorphism in the IL-6 gene has been associated with elevated IL-6 levels and an increased risk of developing pulmonary arterial hypertension (PAH) (Fang et al., *J. Am. Soc. Hypertens.*, 2017, 11(3), 171-177). Corroborating the role of IL-6 in PAH, inhibition of the IL-6 receptor chain gp130 ameliorated the disease in a rat model of PAH (Huang et al., *Can. J. Cardiol.*, 2016, 32(11), 1356.e1-1356.e10).

Cytokines such as IFNγ, IL-12 and IL-6 have been implicated in a range of non-allergic lung diseases such as sarcoidosis, and lymphangioleiomyomatosis (El-Hashemite et al., *Am. J. Respir. Cell. Mol. Biol.*, 2005, 33, 227-230, and El-Hashemite et al., *Cancer Res.*, 2004, 64, 3436-3443). The compounds of the invention have also been shown to inhibit IL-6 and IFNγ signaling.

Bronchiectasis and infiltrative pulmonary diseases are diseases associated with chronic neutrophilic inflammation.

Pathological T cell activation is critical in the etiology of multiple respiratory diseases. Autoreactive T cells play a role in bronchiolitis obliterans organizing pneumonia (also termed COS). Similar to COS the etiology of lung transplant rejections is linked to an aberrant T cell activation of the recipients T cells by the transplanted donor lung. Lung transplant rejections may occur early as Primary Graft Dysfunction (PGD), organizing pneumonia (OP), acute rejection (AR) or lymphocytic bronchiolitis (LB) or they may occur years after lung transplantation as Chronic Lung Allograft Dysfunction (CLAD). CLAD was previously known as bronchiolitis obliterans (BO) but now is considered a syndrome that can have different pathological manifestations including BO, restrictive CLAD (rCLAD or RAS) and neutrophilic allograft dysfunction. Chronic lung allograft dysfunction (CLAD) is a major challenge in long-term management of lung transplant recipients as it causes a transplanted lung to progressively lose functionality (Gauthier et al., *Curr Transplant Rep.*, 2016, 3(3), 185-191). CLAD is poorly responsive to treatment and therefore, there remains a need for effective compounds capable of preventing or treating this condition. Several JAK-dependent cytokines such as IFNγ and IL-5 are up-regulated in CLAD and lung transplant rejection (Berastegui et al, *Clin. Transplant.* 2017, 31, e12898). Moreover, high lung levels of CXCR3 chemokines such as CXCL9 and CXCL10 which are downstream of JAK-dependent IFN signaling, are linked to worse outcomes in lung transplant patients (Shino et al, *PLOS One*, 2017, 12 (7), e0180281). Systemic JAK inhibition has been shown to be effective in kidney transplant rejection (Vicenti et al., *American Journal of Transplantation*, 2012, 12, 2446-56). Therefore, JAK inhibitors have the potential to be effective in treating or preventing lung transplant rejection and CLAD. Similar T cell activation events as described as the basis for lung transplant rejection also are considered the main driver of lung graft-versus-host disease (GVHD)

which can occur post hematopoietic stem cell transplants. Similar to CLAD, lung GVHD is a chronic progressive condition with extremely poor outcomes and no treatments are currently approved. A retrospective, multicenter survey study of 95 patients with steroid-refractory acute or chronic GVHD who received the systemic JAK inhibitor ruxolitinib as salvage therapy demonstrated complete or partial response to ruxolitinib in the majority of patients including those with lung GVHD (Zeiser et al, *Leukemia,* 2015, 29, 10, 2062-68). As systemic JAK inhibition is associated with serious adverse events and a small therapeutic index, the need remains for an inhaled lung-directed, non-systemic JAK inhibitor to prevent and/or treat lung transplant rejection or lung GVHD. The compounds of the invention have the characteristics required to meet this need. More recently, immune-checkpoint inhibitor induced pneumonitis, another T cell mediated lung disease emerged with the increased use of immune-checkpoint inhibitors. In cancer patients treated with these T cell stimulating agents, fatal pneumonitis can develop.

The mixed lymphocyte reaction assay is an in-vitro assay that mimics transplant rejection. Compound 1 was shown to effectively inhibit IFNγ secretion.

In one aspect, therefore, the invention provides a method of treating a respiratory disease in a mammal (e.g., a human), the method comprising administering to the mammal a therapeutically-effective amount of a compound of the invention, or a pharmaceutically acceptable salt thereof, or of a pharmaceutical composition comprising a pharmaceutically-acceptable carrier and a compound of the invention, or a pharmaceutically acceptable salt thereof.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, or sarcoidosis. In another aspect, the respiratory disease is asthma or chronic obstructive pulmonary disease.

In one aspect, the respiratory disease is a lung infection, an eosinophilic disease, a helminthic infection, pulmonary arterial hypertension, sarcoidosis, lymphangioleiomyomatosis, bronchiectasis, an infiltrative pulmonary disease, drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, acute and chronic lung transplant rejections (including PGD, OP, LB, AR and CLAD, BO, restrictive CLAD and neutrophilic allograft dysfunction), lung graft-versus-host disease bronchiolitis obliterans organizing pneumonia, pulmonary arterial hypertension, bronchiectasis, or immune-checkpoint-inhibitor induced pneumonitis.

The invention further provides a method of treating asthma in a mammal, the method comprising administering to the mammal a therapeutically-effective amount of a compound of the invention, or a pharmaceutically acceptable salt thereof, or of a pharmaceutical composition comprising a pharmaceutically-acceptable carrier and a compound of the invention, or a pharmaceutically acceptable salt thereof.

When used to treat asthma, the compounds of the invention will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

The disclosure further provides a method of treating a respiratory disease (including but not limited to the disease described herein) in a mammal, the method comprising administering to the mammal a therapeutically-effective amount of a compound of the disclosure, or a pharmaceutically acceptable salt thereof, or of a pharmaceutical composition comprising a pharmaceutically-acceptable carrier and a compound of the disclosure, or a pharmaceutically acceptable salt thereof.

When used to treat a respiratory disease (including but not limited to the disease described herein), the compounds of the disclosure will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

As JAK inhibitors, the compounds of the disclosure may also be useful for a variety of other diseases. The compounds of the disclosure may be useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J. Clin. Immunology,* 1996, 16, 144-150), Crohn's disease (Woywodt et al., *Eur. J. Gastroenterology Hepatology,* 1999, 11, 267-276), collagenous colitis (Kumawat et al., *Mol. Immunology,* 2013, 55, 355-364), lymphocytic colitis (Kumawat et al., 2013), eosinophilic esophagitis (Weinbrand-Goichberg et al., *Immunol. Res.,* 2013, 56, 249-260), graft versus host disease-related colitis (Coghill et al., *Blood,* 2001, 117, 3268-3276), infectious colitis (Stallmach et al., *Int. J. Colorectal Dis.,* 2004, 19, 308-315), Behcet's disease (Zhou et al., *Autoimmun. Rev.,* 2012, 11, 699-704), celiac disease (de Nitto et al., *World J. Gastroenterol.,* 2009, 15, 4609-4614), immune checkpoint inhibitor induced colitis (e.g., CTLA-4 inhibitor-induced colitis; (Yano et al., *J. Translation. Med.,* 2014, 12, 191), PD-1- or PD-L1-inhibitor-induced colitis), and ileitis (Yamamoto et al., *Dig. Liver Dis.,* 2008, 40, 253-259) are characterized by elevation of certain pro-inflammatory cytokine levels. As many pro-inflammatory cytokines signal via JAK activation, compounds described in this application may be able to alleviate the inflammation and provide symptom relief. In particular, the compounds of the disclosure may be useful for the induction and maintenance of remission of ulcerative colitis, and for the treatment of Crohn's disease, immune checkpoint inhibitor induced colitis, and the gastrointestinal adverse effects in graft versus host disease. In one aspect, therefore, the disclosure provides a method of treating a gastrointestinal inflammatory disease in a mammal (e.g., a human), the method comprising administering to the mammal a compound of the disclosure, or a pharmaceutically acceptable salt thereof, or a pharmaceutical composition comprising a pharmaceutically-acceptable carrier and a compound of the disclosure, or a pharmaceutically acceptable salt thereof.

Atopic dermatitis and other inflammatory skin diseases have been associated with elevation of proinflammatory cytokines that rely on the JAK-STAT pathway. Therefore, the compounds of the disclosure, or a pharmaceutically acceptable salt thereof, may be beneficial in a number of dermal inflammatory or pruritic conditions that include, but are not limited to atopic dermatitis, alopecia areata, vitiligo, psoriasis, dermatomyositis, cutaneous T cell lymphoma (Netchiporouk et al., *Cell Cycle* 2014; 13, 3331-3335) and subtypes (Sezary syndrome, mycosis fungoides, pagetoid reticulosis, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT*, 2013, 2, e24137), alopecia areata (Xing et al., *Nat. Med.* 2014, 20, 1043-1049), vitiligo (Craiglow et al, *JAMA Dermatol.* 2015, 151, 1110-1112), prurigo nodularis (Sonkoly et al., *J. Allergy Clin. Immunol.* 2006, 117, 411-417), lichen planus (Welz-Kubiak et al., *J. Immunol. Res.* 2015, ID:854747), primary localized cutaneous amyloidosis (Tanaka et al., *Br. J. Dermatol.* 2009, 161, 1217-1224), bullous pemphigoid (Feliciani et al., *Int. J. Immunopathol. Pharmacol.* 1999, 12, 55-61), and dermal manifestations of graft versus host disease (Okiyama et al., *J. Invest. Dermatol.* 2014, 134, 992-1000) are characterized by elevation of certain cytokines that signal via JAK activation. Accordingly, compounds of the disclosure, or a pharmaceutically acceptable salt thereof, may be able to alleviate associated dermal inflammation or pruritus driven by these cytokines. In particular, compounds of the disclosure, or a pharmaceutically acceptable salt thereof, may be expected to be useful for the treatment of atopic dermatitis and other inflammatory skin diseases. In one aspect, therefore, the disclosure provides a method of treating an inflammatory skin disease in a mammal (e.g., a human), the method comprising applying a pharmaceutical composition comprising a compound of the disclosure, or a pharmaceutically acceptable salt thereof and a pharmaceutical carrier to the skin of the mammal. In one aspect, the inflammatory skin disease is atopic dermatitis.

Many ocular diseases have been shown to be associated with elevations of proinflammatory cytokines that rely on the JAK-STAT pathway. The compounds of the disclosure, or a pharmaceutically acceptable salt thereof, therefore, may be useful for the treatment of a number of ocular diseases that include, but are not limited to, uveitis, diabetic retinopathy, diabetic macular edema, dry eye disease, age-related macular degeneration, and atopic keratoconjunctivitis. In particular, uveitis (Horai and Caspi, *J. Interferon Cytokine Res.*, 2011, 31, 733-744), diabetic retinopathy (Abcouwer, *J. Clin. Cell. Immunol.*, 2013, Suppl 1, 1-12), diabetic macular edema (Sohn et al., *American Journal of Opthamology*, 2011, 152, 686-694), dry eye disease (Stevenson et al, *Arch. Ophthalmol.*, 2012, 130, 90-100), and age-related macular degeneration (Knickelbein et al, *Int. Ophthalmol. Clin.*, 2015, 55(3), 63-78) are characterized by elevation of certain pro-inflammatory cytokines that signal via the JAK-STAT pathway. Accordingly, compounds of the disclosure, or a pharmaceutically acceptable salt thereof, may be able to alleviate the associated ocular inflammation and reverse disease progression or provide symptom relief. In one aspect, therefore, the disclosure provides a method of treating an ocular disease in a mammal, the method comprising administering a pharmaceutical composition comprising a compound of the disclosure or a pharmaceutically-acceptable salt thereof and a pharmaceutical carrier to the eye of the mammal. In one aspect, the ocular disease is uveitis, diabetic retinopathy, diabetic macular edema, dry eye disease, age-related macular degeneration, or atopic keratoconjunctivitis. In one aspect, the method comprises administering the compound of the disclosure, or a pharmaceutically acceptable salt thereof by intravitreal injection. Compounds of the disclosure, or a pharmaceutically acceptable salt thereof, may also be used in combination with one or more compound useful to ocular diseases.

The compounds of the disclosure, or a pharmaceutically acceptable salt thereof, may also be useful to treat other diseases such as other inflammatory diseases, autoimmune diseases or cancers. The compounds of the disclosure, or a pharmaceutically acceptable salt thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

Combination Therapy

Compounds of the disclosure or a pharmaceutically acceptable salt thereof may be used in combination with one or more agents which act by the same mechanism or by different mechanisms to treat a disease. The different agents may be administered sequentially or simultaneously, in separate compositions or in the same composition. Useful classes of agents for combination therapy include, but are not limited to, a beta 2 adrenoceptor agonist, a muscarinic receptor antagonist, a glucocorticoid agonist, a G-protein coupled receptor-44 antagonist, a leukotriene D4 antagonist, a muscarinic M3 receptor antagonist, a histamine H1 receptor antagonist, an immunoglobulin E antagonist, a PDE 4 inhibitor, an IL-4 antagonist, a muscarinic M1 receptor antagonist, a histamine receptor antagonist, an IL-13 antagonist, an IL-5 antagonist, a 5-Lipoxygenase inhibitor, a beta adrenoceptor agonist, a CCR3 chemokine antagonist, a CFTR stimulator, an immunoglobulin modulator, an interleukin 33 ligand inhibitor, a PDE 3 inhibitor, a phosphoinositide-3 kinase delta inhibitor, a thromboxane A2 antagonist, an elastase inhibitor, a Kit tyrosine kinase inhibitor, a leukotriene E4 antagonist, a leukotriene antagonist, a PGD2 antagonist, a TNF alpha ligand inhibitor, a TNF binding agent, a complement cascade inhibitor, an eotaxin ligand inhibitor, a glutathione reductase inhibitor, an histamine H4 receptor antagonist, an IL-6 antagonist, an IL2 gene stimulator, an immunoglobulin gamma Fc receptor IIB modulator, an interferon gamma ligand, an interleukin 13 ligand inhibitor, an interleukin 17 ligand inhibitor, a L-Selectin antagonist, a leukocyte elastase inhibitor, a leukotriene C4 antagonist, a Leukotriene C4 synthase inhibitor, a membrane copper amine oxidase inhibitor, a metalloprotease-12 inhibitor, a metalloprotease-9 inhibitor, a mite allergen modulator, a muscarinic receptor modulator, a nicotinic acetylcholine receptor agonist, a nuclear factor kappa B inhibitor, a p-Selectin antagonist, a PDE 5 inhibitor, a PDGF receptor antagonist, a phosphoinositide-3 kinase gamma inhibitor, a TLR-7 agonist, a TNF antagonist, an Abl tyrosine kinase inhibitor, an acetylcholine receptor antagonist, an acidic mammalian chitinase inhibitor, an ACTH receptor agonist, an actin polymerization modulator, an adenosine A1 receptor antagonist, an adenylate cyclase stimulator, an adrenoceptor antagonist, an adrenocorticotrophic hormone ligand, an alcohol dehydrogenase 5 inhibitor, an alpha 1 antitrypsin stimulator, an alpha 1 proteinase inhibitor, an androgen receptor modulator, an angiotensin converting enzyme 2 stimulator, an ANP agonist, a Bcr protein inhibitor, a beta 1 adrenoceptor antagonist, a beta 2 adrenoceptor antagonist, a beta 2 adrenoceptor modulator, a beta amyloid modulator, a BMP10 gene inhibitor, a BMP15 gene inhibitor, a calcium channel inhibitor, a cathepsin G inhibitor, a CCL26 gene inhibitor, a CCR3 chemokine modulator, a CCR4 chemokine antagonist, a cell adhesion molecule inhibitor, a chaperonin stimulator, a chitinase inhibitor, a collagen I antagonist, a complement C3 inhibitor, a CSF-1 antagonist, a CXCR2 chemokine antagonist, a cytokine receptor common beta chain modulator, a cytotoxic T-lymphocyte protein-4 stimulator, a deoxyribonuclease I stimulator, a deoxyribonuclease stimulator, a dipeptidyl peptidase I inhibitor, a DNA gyrase inhibitor, a DP prostanoid receptor modulator, an E-Selectin antagonist, an EGFR family tyrosine kinase receptor inhibitor, an elastin modulator, an Endothelin ET-A antagonist, an Endothelin ET-B antagonist, an epoxide hydrolase inhibitor, a FGF3 receptor antagonist, a Fyn tyrosine kinase inhibitor, a GATA 3 transcription factor inhibitor, a Glucosylceramidase modulator, a Glutamate receptor modulator, a GM-CSF ligand inhibitor, a Guanylate cyclase stimulator, a H+ K+ ATPase inhibitor, an hemoglobin modulator, an Heparin agonist, an Histone deacetylase inhibitor, an Histone deacetylase-2 stimulator, an HMG CoA reductase inhibitor, an I-kappa B kinase beta inhibitor, an ICAM1 gene inhibitor, an IL-17 antagonist, an IL-17 receptor modulator, an IL-23 antagonist, an IL-4 receptor modulator, an Immunoglobulin G modulator, an Immunoglobulin G1 agonist, an Immunoglobulin G1 modulator, an Immunoglobulin epsilon Fc receptor IA antagonist, an Immunoglobulin gamma Fc receptor IIB antagonist, an Immunoglobulin kappa modulator, an Insulin sensitizer, an Interferon beta ligand, an Interleukin 1 like receptor antagonist, an Interleukin 18 ligand inhibitor, an Interleukin receptor 17A antagonist, an Interleukin-1 beta ligand inhibitor, an Interleukin-5 ligand inhibitor, an Interleukin-6 ligand inhibitor, a KCNA voltage-gated potassium channel-3 inhibitor, a Kit ligand inhibitor, a Laminin-5 agonist, a Leukotriene CysLT1 receptor antagonist, a Leukotriene CysLT2 receptor antagonist, a LOXL2 gene inhibitor, a Lyn tyrosine kinase inhibitor, a MARCKS protein inhibitor, a MDR associated protein 4 inhibitor, a Metalloprotease-2 modulator, a Metalloprotease-9 modulator, a Mineralocorticoid receptor antagonist, a Muscarinic M2 receptor antagonist, a Muscarinic M4 receptor antagonist, a Muscarinic M5 receptor antagonist, a Natriuretic peptide receptor A agonist, a Natural killer cell receptor modulator, a Nicotinic ACh receptor alpha 7 subunit stimulator, a NK cell receptor modulator, a Nuclear factor kappa B modulator, an opioid growth factor receptor agonist, a P-Glycoprotein inhibitor, a P2X3 purinoceptor antagonist, a p38 MAP kinase inhibitor, a Peptidase 1 modulator, a phospholipase A2 inhibitor, a phospholipase C inhibitor, a plasminogen activator inhibitor 1 inhibitor, a platelet activating factor receptor antagonist, a PPAR gamma agonist, a prostacyclin agonist, a protein tyrosine kinase inhibitor, a SH2 domain inositol phosphatase 1 stimulator, a signal transduction inhibitor, a sodium channel inhibitor, a STAT-3 modulator, a Stem cell antigen-1 inhibitor, a superoxide dismutase modulator, a T cell surface glycoprotein CD28 inhibitor, a T-cell surface glycoprotein CD8 inhibitor, a TGF beta agonist, a TGF beta antagonist, a thromboxane synthetase inhibitor, a thymic stromal lymphoprotein ligand inhibitor, a thymosin agonist, a thymosin beta 4 ligand, a TLR-8 agonist, a TLR-9 agonist, a TLR9 gene stimulator, a Topoisomerase IV inhibitor, a Troponin I fast skeletal muscle stimulator, a Troponin T fast skeletal muscle stimulator, a Type I IL-1 receptor antagonist, a Type II TNF receptor modulator, an ion channel modulator, a uteroglobin stimulator, and a VIP agonist.

Specific agents that may be used in combination with the present JAK inhibitor compounds include, but are not limited to rosiptor acetate, umeclidinium bromide, secukinumab, metenkefalin acetate, tridecactide acetate, fluticasone propionate, alpha-cyclodextrin-stabilized sulforaphane, tezepelumab, mometasone furoate, BI-1467335, dupilumab, aclidinium, formoterol, AZD-1419, HI-1640V, rivipansel, CMP-001, mannitol, ANB-020, omalizumab, tregalizumab, Mitizax, benralizumab, golimumab, roflumilast, imatinib, REGN-3500, masitinib, apremilast, RPL-554, Actimmune, adalimumab, rupatadine, parogrelil, MK-1029, beclometasone dipropionate, formoterol fumarate, mogamulizumab, seratrodast, UCB-4144, nemiralisib, CK-2127107, fevipiprant, danirixin, bosentan, abatacept, EC-18, duvelisib, dociparstat, ciprofloxacin, salbutamol HFA, erdosteine, PrEP-001, nedocromil, CDX-0158, salbutamol, enobosarm, R-TPR-022, lenzilumab, fluticasone furoate, vilanterol trifenatate, fluticasone propionate, salmeterol, PT-007, PRS-060, remestemcel-L, citrulline, RPC-4046, nitric oxide, DS-102, gerilimzumab, Actair, fluticasone furoate, umeclidinium, vilanterol, AG-NPP709, Gamunex, infliximab, Ampion, acumapimod, canakinumab, INS-1007, CYP-001, sirukumab, fluticasone propionate, mepolizumab, pitavastatin, solithromycin, etanercept, ivacaftor, anakinra, MPC-300-IV, glycopyrronium bromide, aclidinium bromide, FP-025, risankizumab, glycopyrronium, formoterol fumarate, Adipocell, YPL-001, tiotropium bromide, glycopyrronium bromide, indacaterol maleate, andecaliximab, olodaterol, esomeprazole, dust mite vaccine, mugwort pollen allergen vaccine, vamorolone, gefapixant, revefenacin, gefitinib, Rejoin, tipelukast, bedoradrine, SCM-CGH, SHP-652, RNS-60, brodalumab, BIO-11006, umeclidinium bromide, vilanterol trifenatate, ipratropium bromide, tralokinumab, PUR-1800, VX-561, VX-371, olopatadine, tulobuterol, formoterol fumarate, triamcinolone acetonide, reslizumab, salmeterol xinafoate, fluticasone propionate, beclometasone dipropionate, formoterol fumarate, tiotropium bromide, ligelizumab, RUTI, bertilimumab, omalizumab, glycopyrronium bromide, SENS-111, beclomethasone dipropionate, CHF-5992, LT-4001, indacaterol, glycopyrronium bromide, mometasone furoate, fexofenadine, glycopyrronium bromide, azithromycin, AZD-7594, formoterol, CHF-6001, batefenterol, OATD-01, olodaterol, CJM-112, rosiglitazone, salmeterol, setipiprant, inhaled interferon beta, AZD-8871, plecanatide, fluticasone, salmeterol, eicosapentaenoic acid monoglycerides, lebrikizumab, RG-6149, QBKPN, Mometasone, indacaterol, AZD-9898, sodium pyruvate, zileuton, CG-201, imidafenacin, CNTO-6785, CLBS-03, mometasone, RGN-137, procaterol, formoterol, CCI-15106, POL-6014, indacaterol, beclomethasone, MV-130, GC-1112, Allergovac depot, MEDI-3506, QBW-251, ZPL-389, udenafil, GSK-3772847, levocetirizine, AXP-1275, ADC-3680, timapiprant, abediterol, AZD-7594, ipratropium bromide, salbutamol sulfate, tadekinig alfa, ACT-774312, dornase alfa, iloprost, batefenterol, fluticasone furoate, alicaforsen, ciclesonide, emeramide, arformoterol, SB-010, Ozagrel, BTT-1023, Dectrekumab, levalbuterol, pranlukast, hyaluronic acid, GSK-2292767, Formoterol, NOV-14, Lucinactant, salbutamol, prednisolone, ebastine, dexamethasone cipecilate, GSK-2586881, BI-443651, GSK-2256294, VR-179, VR-096, hdm-ASIT+, budesonide, GSK-2245035, VTX-1463, Emedastine, dexpramipexole, levalbuterol, N-6022, dexamethasone sodium phosphate, PIN-201104, OPK-0018, TEV-48107, suplatast, BI-1060469, Gemilukast, interferon gamma, dalazatide, bilastine, fluticasone propionate, salmeterol xinafoate, RP-3128, bencycloquidium bromide, reslizumab, PBF-680, CRTH2 antagonist, Pranlukast, salmeterol xinafoate, fluticasone propionate, tiotropium bromide monohydrate, masilukast, RG-7990, Doxofylline, abediterol, glycopyrronium bromide, TEV-46017, ASM-024, fluticasone propionate, glycopyrronium bromide, salmeterol xinafoate, salbutamol, TA-270, Flunisolide, sodium chromoglycate, Epsi-gam, ZPL-521, salbutamol, aviptadil, TRN-157, Zafirlukast, Stempeucel, pemirolast sodium, nadolol, fluticasone propionate+salmeterol xinafoate, RV-1729, salbutamol sulfate, carbon dioxide+perfluorooctyl bromide, APL-1, dectrekumab+VAK-694, lysine acetylsalicylate, zileuton, TR-4, human allogenic adipose-derived mesenchymal progenitor cell therapy, MEDI-9314, PL-3994, HMP-301, TD-5471, NKTT-120, pemirolast, beclomethasone dipropionate, trantinterol, monosodium alpha luminol, IMD-1041, AM-211, TBS-5, ARRY-502, seratrodast, recombinant midismase, ASM-8, deflazacort, bambuterol, RBx-10017609, ipratropium+fenoterol, fluticasone+formoterol, epinastine, WIN-901X, VALERGEN-DS, OligoG-COPD-5/20, tulobuterol, oxis Turbuhaler, DSP-3025, ASM-024, mizolastine, budesonide+salmeterol, LH-011, AXP-E, histamine human immunoglobulin, YHD-001, theophylline, ambroxol+erdosteine, ramatroban, montelukast, pranlukast, AG-1321001, tulobuterol, ipratropium+salbutamol, tranilast, methylprednisolone suleptanate, colforsin daropate, repirinast, and doxofylline.

Also provided, herein, is a pharmaceutical composition comprising a compound of the disclosure or a pharmaceutically acceptable salt thereof and one or more other therapeutic agents. The therapeutic agent may be selected from the class of agents specified above and from the list of specific agent described above. In some embodiments, the pharmaceutical composition is suitable for delivery to the lungs. In some embodiments, the pharmaceutical composition is suitable for inhaled or nebulized administration. In some embodiments, the pharmaceutical composition is a dry powder or a liquid composition.

Further, in a method aspect, the disclosure provides a method of treating a disease or disorder in a mammal comprising administering to the mammal a compound of the disclosure or a pharmaceutically acceptable salt thereof and one or more other therapeutic agents.

When used in combination therapy, the agents may be formulated in a single pharmaceutical composition, or the agents may be provided in separate compositions that are administered simultaneously or at separate times, by the same or by different routes of administration. Such compositions can be packaged separately or may be packaged together as a kit. The two or more therapeutic agents in the kit may be administered by the same route of administration or by different routes of administration.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
DCM=dichloromethane
DIPEA=N,N-diisopropylethylamine
DMF=N,N-dimethylformamide
EtOAc=ethyl acetate
h=hour(s)
HATU=N,N,N',N'-tetramethyl-O-(7-azabenzotriazol-1-yl)uronium hexafluorophosphate
IPA=isopropyl alcohol
IPAc=isopropylacetate
MeOH=methanol
min=minute(s)
Pd(PPh$_3$)$_4$=tetrakis(triphenylphosphine)palladium(0)
RT=room temperature
TFA=trifluoroacetic acid
THF=tetrahydrofuran
bis(pinacolato)diboron=4,4,5,5,4',4',5',5'-octamethyl-[2,2']bi[[1,3,2]dioxaborolanyl]

Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Preparative HPLC Conditions
Column: C18, 5 μm. 21.2×150 mm or C18, 5 μm 21×250 or C14, 5 μm 21×150 mm
Column temperature: Room Temperature
Flow rate: 20.0 mL/min
Mobile Phases: A=Water+0.05% TFA B=ACN+0.05% TFA,
Injection volume: (100-1500 μL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 μL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Preparation 1: 4-(benzyloxy)-2-ethylphenyl)trifluoro-$\lambda^4$-borane, potassium salt I-5

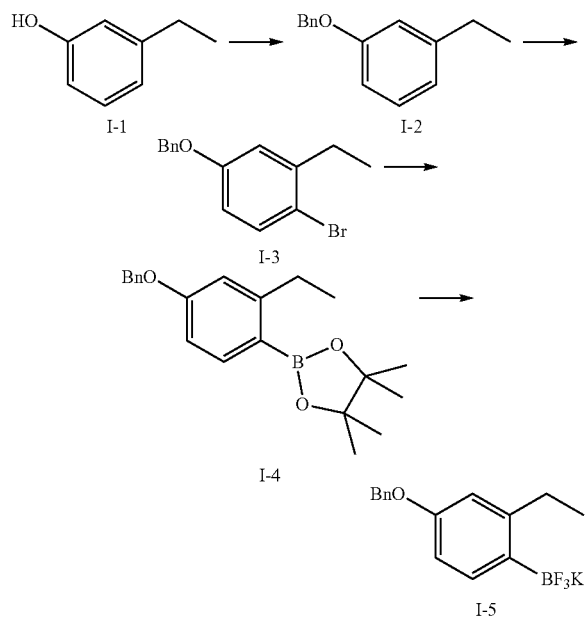

(a) 1-(benzyloxy)-3-ethylbenzene (I-2)

To a stirred solution of 3-ethylphenol (I-1) (25.0 g, 204.0 mmol) in ACN (250 mL, 10 vol) was added potassium carbonate (42.0 g, 306 mmol) at room temperature. The resulting reaction mass was stirred at room temperature for 15 minutes, followed by the addition of benzyl bromide (24.0 mL, 204 mmol) in drop wise manner. The resulting reaction mixture was stirred for 6 hours at room temperature. After completion of the reaction (TLC monitoring), the resulting reaction mass was poured into water (1.0 L) followed by the extraction of compound with EtOAc (2×2 L). The combined organics were washed with cold water, brine solution and dried over sodium sulfate, filtered and evaporated under reduced pressure. The crude product was then purified by column chromatography over silica gel (100-200 M) by using eluents 2% EtOAc in hexane to get the desired product (I-2) as light yellow oily compound (35.0 g, 81%). $^1$H NMR (400 MHz, chloroform-d) δ 7.46-7.44 (m, 2H), 7.39 (t, J=7.6 Hz, 2H), 7.34-7.31 (m, 1H), 7.21 (t, J=7.6 Hz), 6.86-6.80 (m, 3H), 5.07 (s, 2H), 2.64 (q, J=7.6 Hz, 2H), 1.24 (t, J=7.6 Hz, 3H).

(b) 4-(benzyloxy)-1-bromo-2-ethylbenzene (I-3)

To an ice cold stirred solution of 1-(benzyloxy)-3-ethylbenzene (I-2) (35.0 g, 164 mmol) in ACN (525 mL, 15 vol) was added N-bromosuccinimide (32.0 g 181 mmol) in portions over a period of 15 minutes. The resulting reaction mixture was stirred for next 1 hour at room temperature. After completion of reaction (TLC monitoring), the resulting reaction mass was poured into ice cold water (1.50 L) followed by the extraction of compound with EtOAc (2×1 L). The combined organics were washed with water and dried over sodium sulfate, filtered and evaporated under reduced pressure to obtain the crude product. n-Hexane (250 mL) was added to the crude material, resulting in a slurry, followed by filtration through a sintered funnel. Mother liquor was evaporated under reduced pressure to obtain the desired product I-3 as light yellow oily compound (42.0 g, 87%). $^1$H NMR (400 MHz, chloroform-d) δ 7.52-7.29 (m, 7H), 6.88 (s, 1H), 6.68 (d, J=6.0 Hz, 1H), 5.04 (s, 2H), 2.69 (q, J=7.6 Hz, 2H), 1.20 (t, J=7.5 Hz, 3H).

(c) 2-(4-(benzyloxy)-2-ethylphenyl)-4,4,5,5-tetramethyl-1,3,2-dioxaborolane (I-4)

A stirred solution of 4-(benzyloxy)-1-bromo-2-ethylbenzene (I-3) (42.0 g, 144 mmol), bis(pinacolato) diboron (44.0 g, 173 mmol), and potassium acetate (28 g, 288 mmol) in dioxane (440 mL) was degassed by purging N2 (g) for 15 min followed by addition of PdCl$_2$(dppf).DCM complex (11.0 g, 15 mmol). The resulting reaction mixture was heated up to 80° C. for next 16 h. After completion of the reaction (TLC monitoring), the reaction mass was filtered through celite bed and mother liquor was evaporated under reduced pressure to obtain the crude product. Crude residue was purified by column chromatography over silica gel (100-200 M) by using eluents 1% EtOAc in hexane to get the desired product (I-4) as light yellow oily compound (32.0 g, 66%). $^1$H NMR (400 MHz, chloroform-d) δ 7.74 (d, J=8.4 Hz, 1H), 7.45-7.36 (m, 5H), 6.84-6.78 (m, 2H), 5.08 (s, 2H), 2.91 (q, J=7.6 Hz), 1.33 (s, 12H), 1.19 (t, J=7.6 Hz, 3H).

(d) (4-(benzyloxy)-2-ethylphenyl)trifluoro-$\lambda^4$-borane, potassium salt (I-5)

To a stirred solution of compound 2-(4-(benzyloxy)-2-ethylphenyl)-4,4,5,5-tetramethyl-1,3,2-dioxaborolane (I-4) (20 g, 59.0 mmol), in acetone:methanol (200 mL, 1:1 ratio, 10 vol), was added a 3M solution of potassium hydrogen fluoride (23.0 g, 295 mmol, dissolved in 98.0 mL of water). The resulting reaction mixture was stirred at room temperature for 16 hours. After completion of the reaction (TLC monitoring), the resulting reaction mass was evaporated under reduced pressure. The solid thus obtained was taken up in water (100 mL) and stirred at room temperature for 30 min. The resulting reaction mass was filtered through a sintered funnel, washed with n-hexane and dried under reduced pressure to provide the desired product (I-5) as a white solid (14.0 g, 74%). $^1$H NMR (400 MHz, chloroform-d) δ 7.43 (d, J=7.2 Hz, 2H), 7.37 (t, J=7.5 Hz, 2H), 7.30 (t, J=7.1 Hz, 1H), 7.22 (d, J=8.0 Hz), 6.58 (s, 1H), 6.53 (d, J=7.9 Hz, 1H), 5.00 (s, 2H), 2.65 (q, J=7.5 Hz, 2H), 1.07 (t, J=7.4 Hz, 3H).

Preparation 2: 6-benzyl 5-(tert-butyl) (S)-3-benzyl-3,4,6,7-tetrahydro-5H-imidazo[4,5-c]pyridine-5,6-dicarboxylate (I-11)

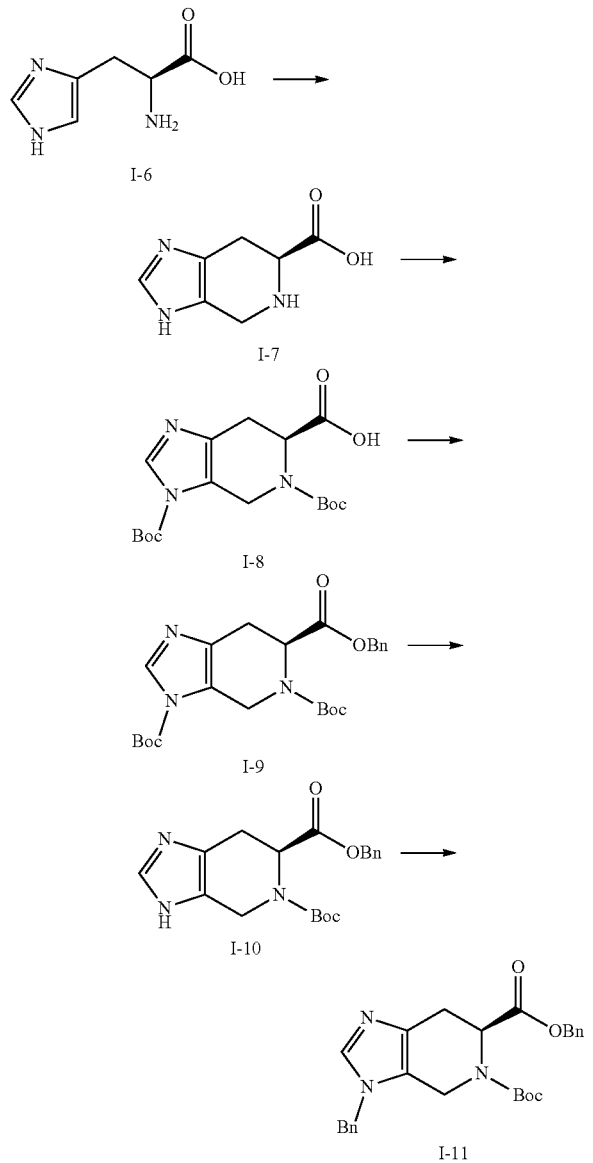

(a) (S)-4,5,6,7-tetrahydro-3H-imidazo[4,5-c]pyridine-6-carboxylic acid, hydrochloride salt (I-7)

To an ice cold stirred suspension of L-histidine (I-6) (5.0 kg, 32.14 mol) in water (40 L, 8 vol.) was added concentrated hydrochloric acid (3.93 L, 33.75 mol), followed by the addition of formaldehyde (5.50 L, 67.5 mol, 37% aq. solution) in drop wise manner. The resulting solution was stirred for 30 minute at same temperature and then heated at 80° C. for 8 hours. Reaction progress was monitored by LCMS. Water was removed under reduced pressure to obtain the crude product, and the resulting crude was stirred for 2 hours in Toluene (20 L). Organics were removed under reduced pressure to remove excess water and the compound was azeotropically dried. The resulting material was then taken in diethyl ether (20 L) and stirred for 2 hours. The solid material was then filtered and air dried to obtain the desired product (I-7) as an off-white solid (6.50 Kg, 85%). $^1$H NMR (400 MHz, D2O) δ 8.69 (s, 1H), 4.56 (d, J=15.4 Hz, 1H), 4.42 (d, J=15.5 Hz, 1H), 4.20 (dd, J=5.5, 5.2 Hz, 1H), 3.42 (dd, J=5.0, 17.0 Hz, 1H), 3.11 (dd, J=10.2, 16.8 Hz, 1H).

(b) (S)-3,5-bis(tert-butoxycarbonyl)-4,5,6,7-tetrahydro-3H-imidazo[4,5-c]pyridine-6-carboxylic acid (I-8)

To an ice cold stirred solution of (S)-4,5,6,7-tetrahydro-3H-imidazo[4,5-c]pyridine-6-carboxylic acid di-hydrochloride (I-7) (6.10 Kg, 25.40 mol) in 1,4-dioxane (48 L, 8 vol) and water (48 L, 8 vol) was added triethylamine (12.36 L, 89 mol) drop wise followed by the addition of di-tert-butyl dicarbonate (18.07 L, 78.74 mol, dissolved in 5 L of 1,4-dioxane) over a period of 30 min. The resulting reaction mixture was stirred at room temperature for next 16 hours. After completion of reaction (TLC & LCMS monitoring), the yellowish reaction mixture was diluted with water (10 L) and washed successively with diethyl ether (2×10 L) and EtOAc (2×7.50 L). The organic phase was discarded. The aqueous layer was cooled and brought to pH ~3 with 6N HCl solution; the aqueous phase was extracted with EtOAc (3×10 L). The combined organics were washed with brine solution, dried over sodium sulfate, and concentrated under reduced pressure. The oily residue was crystallized from 30% EtOAc:Hexanes to afford the desired product (I-8) as off-white solid (5.1 Kg, 55%). (m/z): [M+H]+ calcd for $C_{17}H_{25}N_3O_6$ 368.18 found 368.21.

(c) 6-benzyl 3,5-di-tert-butyl (S)-6,7-dihydro-3H-imidazo[4,5-c]pyridine-3,5,6(4H)-tricarboxylate (I-9)

To an ice cold solution of (S)-3,5-bis(tert-butoxycarbonyl)-4,5,6,7-tetrahydro-3H-imidazo[4,5-c]pyridine-6-carboxylic acid (I-8) (5.1 Kg, 13.88 mol) in DCM (51 L, 10 vol) was added sequentially saturated aqueous sodium bicarbonate (41.0 L, 8 vol), tetra-butyl ammonium iodide (5.13 Kg, 13.88 mol) and benzyl bromide (2.47 L, 20.82 mol). The resulting reaction mixture was stirred at room temperature for next 16 hours. After completion of the reaction (TLC & LCMS monitoring), the biphasic solution was separated. The aqueous layer was extracted with DCM (3×10 L). The combined organics were washed with brine solution, dried over sodium sulfate, filtered, and concentrated under reduced pressure to obtain the crude product, which was purified by column chromatography through silica gel (100-200 M) by using eluents 40% EtOAc in hexane to get the desired product (I-9) as viscous oil (4.50 Kg, 72%). (m/z): [M+H]+ calcd for $C_{24}H_{31}N_3O_6$ 458.22 found 458.60.

(d) 6-benzyl 5-(tert-butyl) (S)-3,4,6,7-tetrahydro-5H-imidazo[4,5-c]pyridine-5,6-dicarboxylate (I-10)

To an ice cold solution of 6-benzyl 3,5-di-tert-butyl (S)-6,7-dihydro-3H-imidazo[4,5-c]pyridine-3,5,6(4H)-tricarboxylate (I-9) (4.50 Kg, 9.84 mol) in IPA (45 L, 10 vol) was added ammonium hydroxide (36 L, 8 vol) drop wise. The resulting reaction mixture was further stirred at room temperature for the next 16 hours. After completion of the reaction (TLC & LCMS monitoring), the resulting mixture was diluted with water (25 L) followed by extraction with EtOAc (3×20 L). The combined organics were washed with brine solution, dried over sodium sulfate, filtered and concentrated under reduced pressure to yield the crude product which was purified by column chromatography through silica gel (100-200 M) by using eluents 2% MeOH in DCM to obtain the desired product (I-10) as a thick viscous oil (2.70 Kg, 77%). (m/z): [M+H]+ calcd for $C_{19}H_{23}N_3O_4$ 358.17 found 358.33.

(e) 6-benzyl 5-(tert-butyl) (S)-3-benzyl-3,4,6,7-tetrahydro-5H-imidazo[4,5-c]pyridine-5,6-dicarboxylate (I-11)

To an ice cold solution of 6-benzyl 5-(tert-butyl) (S)-3,4,6,7-tetrahydro-5H-imidazo[4,5-c]pyridine-5,6-dicarboxylate (I-10) (2.70 kg, 7.55 mol) in DCM (32.4 L, 12 vol) was added aqueous 1N sodium hydroxide (24.3 L, 9 vol) followed by the sequential addition of tetra-butyl ammonium iodide (2.80 Kg, 7.55 mol) and benzyl bromide (0.99 L, 8.31 mol). The resulting reaction mixture was stirred at room temperature for next 2 hours. After completion of the reaction (TLC & LCMS monitoring), the biphasic solution was separated. The aqueous layer was extracted with DCM (3×10 L). The combined organics were washed with brine solution, dried over sodium sulfate, filtered, and concentrated under reduced pressure to yield the crude product which was purified by column chromatography over silica gel (100-200 M) by using eluents 40% EtOAc in hexane to obtain the desired product (I-11) as a viscous oil (1.70 Kg, 63%). (m/z): [M+H]+ calcd for $C_{26}H_{29}N_3O_4$ 448.22 found 448.20.

Preparation 3: 6-benzyl 5-(tert-butyl) (S)-3-benzyl-2-(6-(4-(benzyloxy)-2-ethylphenyl)-1H-indazol-3-yl)-3,4,6,7-tetrahydro-5H-imidazo[4,5-c]pyridine-5,6-dicarboxylate (I-16)

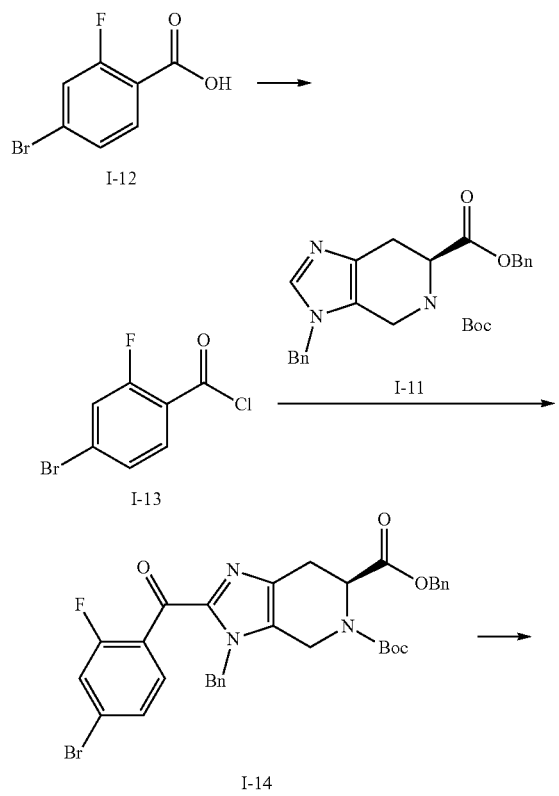

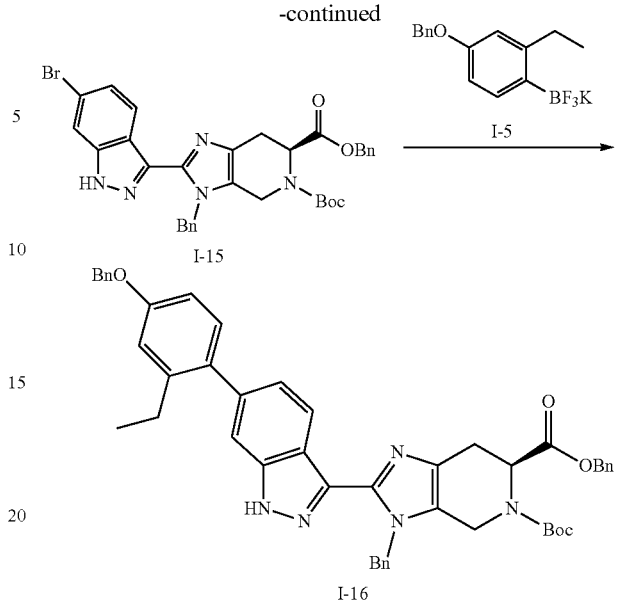

(a) 4-bromo-2-fluorobenzoyl chloride (I-13)

To an ice cold stirred solution of 4-bromo-2-fluorobenzoic acid (I-12) (1.25 Kg, 5.71 mol) in DCM (12.5 L, 15 vol), was added oxalyl chloride (0.98 L, 11.42 mol) in a drop wise manner. The resulting reaction mixture was stirred for 10 min at the same temperature. DMF (150 mL) was then added in a drop wise manner to the reaction mixture. The resulting reaction mass was allowed to warm to room temperature and stirred for 2 hours. After completion of the reaction (by TLC monitoring), excess oxalyl chloride was removed under reduced pressure under a nitrogen atmosphere to obtain the crude product (I-13) (1.08 Kg, 80%), which was used in the next step without further purification.

(b) 6-benzyl 5-(tert-butyl) (S)-3-benzyl-2-(4-bromo-2-fluorobenzoyl)-3,4,6,7-tetrahydro-5H-imidazo[4,5-c]pyridine-5,6-dicarboxylate (I-14)

To a stirred solution of 6-benzyl 5-(tert-butyl) (S)-3-benzyl-3,4,6,7-tetrahydro-5H-imidazo[4,5-c]pyridine-5,6-dicarboxylate (I-11) (1.70 Kg, 3.80 mol) in ACN (13.6 L, 8 vol) was added triethylamine (2.11 L, 15.2 mol) followed by the addition of 4-bromo-2-fluorobenzoyl chloride (I-13) (1.08 Kg, 4.56 mol in 3.4 L ACN, 2 vol) at room temperature. After completion of addition, the resulting reaction mixture color turned brown from light yellow. The resulting reaction mixture was stirred at same temperature for 30 min, and reaction progress was monitored by TLC. The resulting reaction mixture was quenched with ice cold water (10 L), followed by extraction with EtOAc (3×5 L) and combined organics were washed with brine solution. The organics were dried over sodium sulfate, filtered, and concentrated under reduced pressure to yield the crude product which was purified by column chromatography over silica gel (100-200 M) by using eluents 20% EtOAc in hexane to obtain the desired product (I-14) (1.74 Kg, 71%). %). (m/z): [M+H]+ calcd for $C_{33}H_{31}BrFN_3O_5$ 648.14 found 648.20.

(c) 6-benzyl 5-(tert-butyl) (S)-3-benzyl-2-(6-bromo-1H-indazol-3-yl)-3,4,6,7-tetrahydro-5H-imidazo[4,5-c]pyridine-5,6-dicarboxylate (I-15)

To a stirred solution of 6-benzyl 5-(tert-butyl) (S)-3-benzyl-2-(4-bromo-2-fluorobenzoyl)-3,4,6,7-tetrahydro- 5H-imidazo[4,5-c]pyridine-5,6-dicarboxylate (I-14) (1.74 Kg, 2.68 mol) in THF (26.0 L, 15 vol) was added hydrazine hydrate (0.705 L, 13.4 mol) at room temperature. The resulting reaction mixture was heated at 60° C. for 3 hours. After completion of the reaction (TLC monitoring), the resulting reaction mass was poured into ice cold water (10 L) followed by extraction of compound with EtOAc (3×10 L). The combined organics were washed with brine and dried over sodium sulfate, filtered, and evaporated under reduced pressure to yield the crude product, which was purified by column chromatography over silica gel (100-200 M) by using eluents 20% EtOAc in hexane to obtain the desired product (I-15) as an off-white solid (1.12 Kg, 65%). (m/z): [M+H]+ calcd for $C_{33}H_{32}BrN_5O_4$ 642.16 found 642.21.

(d) 6-benzyl 5-(tert-butyl) (S)-3-benzyl-2-(6-(4-(benzyloxy)-2-ethylphenyl)-1H-indazol-3-yl)-3,4,6,7-tetrahydro-5H-imidazo[4,5-c]pyridine-5,6-dicarboxylate (I-16)

Bis(pinacolato)diboron (250 g, 984 mmol) was charged to a 5 L 3-neck single walled flask previously etched using fluoride chemistry, along with propan-2-ol (1882 mL, 2.46 E+04 mmol) and the mixture was stirred until fully dissolved. Dissolution was endothermic (−4° C.). In a 4 L Erlenmeyer flask, previously etched using fluoride chemistry, potassium fluoride hydrofluoride (538 g, 6891 mmol) was dissolved in water (2.306 L, 1.28 E+05 mmol) to form a 3M solution. The dissolution was endothermic (−12° C.). The solution was then filtered to remove a small amount of insoluble material from the potassium fluoride hydrofluoride. Once both solutions were fully dissolved, the contents of the Erlenmeyer flask were charged into the single walled flask portion-wise over 15 minutes. A moderate exotherm was observed (+10° C.). The solution became a thick and translucent semi-opaque gray slurry during the addition and stirring was increased to keep the contents well mixed. The mixture was stirred for 1.5 h, and then filtered through a coarse glass fritted funnel (4 L, previously etched). The filtration required 30-45 minutes to complete. The clear biphasic filtrate was discarded. The white solids were dried for 10 minutes on the filter (cracking of the cake was observed). The solids were transferred back into a cleaned 5 L 3-neck single walled flask and re-slurried with water (1.33 L, 7.38 E+04 mmol). The slurry was stirred for 2 h after which time it formed a clear homogenous hydrogel. The solution was stirred for another 1 h whereupon the solids/gel were filtered out using a 4 L coarse glass funnel (previously etched). The solids were allowed to dry on the filter for 30 minutes. The solids were transferred back to a cleaned 5 L 3-neck single walled flask and reslurried in acetone (1.084 L, 1.48 E+04 mmol). The white/gray slurry was stirred for 1 h and was then filtered on a 4 L coarse glass funnel (previously etched). The filtration required 20 minutes to complete, and was then dried on the funnel for another 1 h. During this time, the solids were occasionally agitated to ensure homogenous drying. A light white powder remained after drying on the filter. The solids were dried for 20 h at 55° C. under vacuum with a slow nitrogen bleed to afford a fluffy white solid (200.3 g were collected).

To a stirred solution of 6-benzyl 5-(tert-butyl) (S)-3-benzyl-2-(6-bromo-1H-indazol-3-yl)-3,4,6,7-tetrahydro-5H-imidazo[4,5-c]pyridine-5,6-dicarboxylate (I-15) (10.0 g, 16.0 mmol) in 2-methyl tetrahydrofuran (100 mL, 10 vol) was added (4-(benzyloxy)-2-ethylphenyl)trifluoro-$\lambda^4$-borane, potassium salt (I-5) (8.0 g, 20 mmol) and the fluffy white solid obtained above (0.20 g). The resulting reaction mixture was degassed with nitrogen gas for 30 minutes. To this solution, a prepared aqueous solution of cesium carbonate (20.0 g, 62.0 mmol in 60 mL water, 6 vol) was added. The resulting reaction mixture was further degassed for 15 minutes followed by addition of bis(di-tert-butyl(4-dimethylaminophenyl)phosphine)dichloropalladium(II) (0.66 g, 0.93 mmol), and the reaction mixture was evacuated under vacuum and flushed by nitrogen. The resulting reaction mixture was heated at 110° C. for 20 hours. After completion of the reaction (TLC & LCMS monitoring), the resulting reaction mixture was cooled to room temperature and filtered through a celite bed, then further washed with EtOAc (3×0.5 L). The combined organics were washed with 1N sodium hydroxide solution (3×0.5 L). The combined organics were then washed with brine and dried over sodium sulfate, filtered, and evaporated under reduced pressure to yield the crude product, which was purified by column chromatography over silica gel (100-200 M) by using eluents 20% EtOAc in hexane to obtain the desired product (I-16) (as mixture of N-benzyl regioisomers) as light yellow solid (8.0 g, 66%). (m/z): [M+H]+ calcd for $C_{48}H_{47}N_5O_5$ 774.36 found 774.59.

Preparation 4: (S)-2-(6-(2-ethyl-4-hydroxyphenyl)-1H-indazol-3-yl)-4,5,6,7-tetrahydro-3H-imidazo[4,5-c]pyridine-6-carboxylic acid, hydrochloride (I-18)

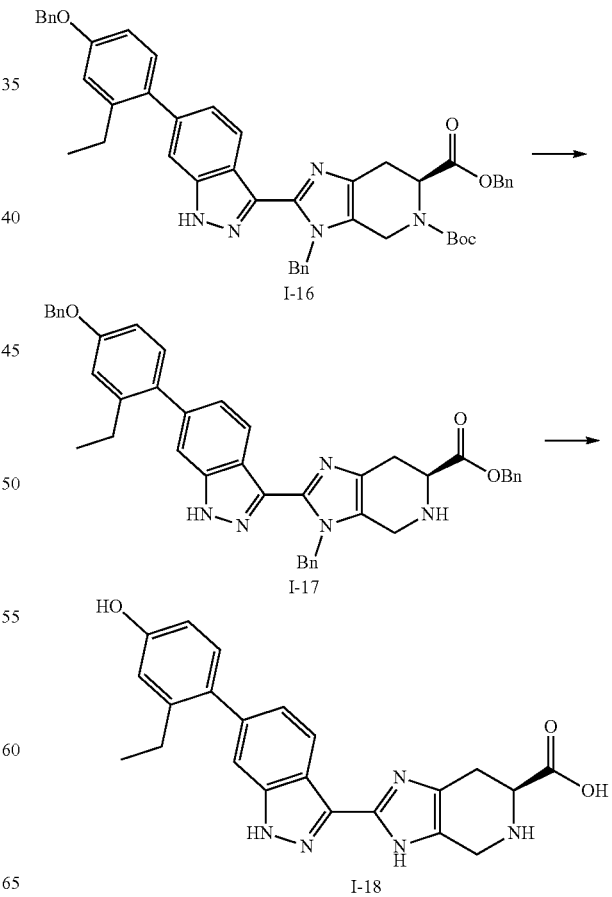

(a) benzyl (S)-3-benzyl-2-(6-(4-(benzyloxy)-2-ethylphenyl)-1H-indazol-3-yl)-4,5,6,7-tetrahydro-3H-imidazo[4,5-c]pyridine-6-carboxylate, hydrochloride (I-17)

6-Benzyl 5-(tert-butyl) (S)-3-benzyl-2-(6-(4-(benzyloxy)-2-ethylphenyl)-1H-indazol-3-yl)-3,4,6,7-tetrahydro-5H-imidazo[4,5-c]pyridine-5,6-dicarboxylate (I-16) (1.0 g, 1.292 mmol) was dissolved in dioxane (8 mL) and water (1.5 mL), then hydrogen chloride solution, 4 M in dioxane (7 mL, 28.0 mmol) was added and the reaction mixture was stirred at room temperature for 3 hours (reaction progress monitored by LCMS). The reaction mixture was then frozen and lyophilized, and the crude product (I-17) was used directly in the next reaction (quantitative yield was assumed). (m/z): [M+H]+ calcd for $C_{43}H_{39}N_5O_3$ 674.31 found 674.3.

(b) (S)-2-(6-(2-ethyl-4-hydroxyphenyl)-1H-indazol-3-yl)-4,5,6,7-tetrahydro-3H-imidazo[4,5-c]pyridine-6-carboxylic acid, hydrochloride (I-18)

Benzyl(S)-3-benzyl-2-(6-(4-(benzyloxy)-2-ethylphenyl)-1H-indazol-3-yl)-4,5,6,7-tetrahydro-3H-imidazo[4,5-c] pyridine-6-carboxylate, hydrochloride (I-17) (0.918 g, 1.292 mmol) was dissolved in 2-propanol (15 mL), hydrogen chloride solution, 5 M in water (0.258 mL, 1.292 mmol), and water (0.25 mL) at 50° C., then palladium, 10% wt. on carbon, 50% water (0.138 g, 0.065 mmol) was added. The reaction flask was then purged with nitrogen, a hydrogen balloon was attached, and the reaction mixture was stirred at 50° C. for 4 days with the hydrogen balloon being replenished as needed (reaction progress monitored by LCMS). All solids were then removed by filtration and the resulting solution was concentrated. The residue was dissolved in 1:1 ACN/Water, frozen, and lyophilized. The resulting powder (I-18) was used without further purification (quantitative yield was assumed). (m/z): [M+H]+ calcd for $C_{22}H_{21}N_5O_3$ 404.17 found 404.2.

Preparation 5: (S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid (I-19)

I-19

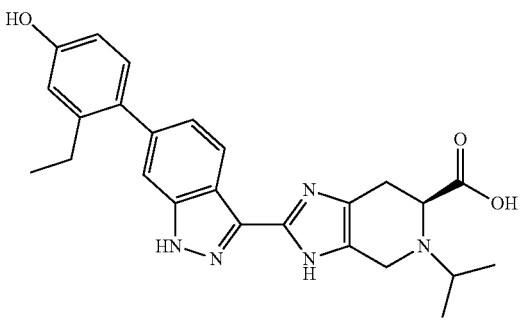

(S)-2-(6-(2-ethyl-4-hydroxyphenyl)-1H-indazol-3-yl)-4,5,6,7-tetrahydro-3H-imidazo[4,5-c]pyridine-6-carboxylic acid, HCl (I-18) (0.25 g, 0.568 mmol) was suspended in DMF (2.5 mL) and acetone (2.5 mL), then acetic acid (0.098 mL, 1.705 mmol) and sodium cyanoborohydride (0.179 g, 2.84 mmol) were added and the reaction mixture was stirred at room temperature for 24 hours (reaction progress was monitored by LCMS). The reaction mixture was concentrated, then the crude product was purified by reverse phase chromatography (5-70% ACN/Water gradient, 50 g C18 aq column) to provide the TFA salt of the title compound (149 mg, 47% yield). (m/z): [M+H]+ calcd for $C_{25}H_{27}N_5O_3$ 446.21 found 446.3.

Example 1: (S)-(3-(dimethylamino)azetidin-1-yl)(2-(6-(2-ethyl-4-hydroxyphenyl)-1H-indazol-3-yl)-5-isopropyl-4,5,6,7-tetrahydro-3H-imidazo[4,5-c]pyridin-6-yl)methanone

1

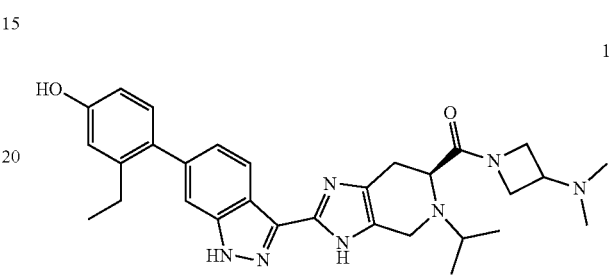

(S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid, TFA (1-19) (50 mg, 0.089 mmol), 3-(Dimethylamino)azetidine dihydrochloride (23.20 mg, 0.134 mmol), and DIPEA (0.078 mL, 0.447 mmol) were dissolved in DMF (1.5 mL), then HATU (51.0 mg, 0.134 mmol) was added and the reaction mixture was stirred at room temperature for 3 hours (reaction progress was monitored by LCMS). Hydrazine (0.014 mL, 0.447 mmol) was added to cleave undesired byproducts, and the solution was stirred at room temperature for 10 minutes. The reaction mixture was then concentrated and the crude product was purified by preparative HPLC (5-70% ACN/Water gradient, C18 column) to provide the TFA salt of the title compound (25 mg, 37% yield). (m/z): [M+H]+ calcd for $C_{30}H_{37}N_7O_2$ 528.30 found 528.3. $^1$H NMR (400 MHz, DMSO-d6) δ 13.09 (s, 1H), 9.40 (s, 1H), 8.27 (d, J=8.31, 1H), 7.30 (s, 1H), 7.04 (m, 2H), 6.71 (d, J=2.54, 1H), 6.64 (dd, J=2.53, 8.26, 1H), 4.26 (m, 1H), 4.06 (m, 2H), 3.82 (m, 2H), 3.64 (m, 2H), 3.03 (m, 2H), 2.74 (m, 2H), 2.47 (q, J=7.56, 2H), 2.07 (d, J=3.69, 6H), 1.07 (m, 6H), 1.00 (t, J=7.50, 3H).

Preparation 6: (S)-5-ethyl-2-(6-(2-ethyl-4-hydroxyphenyl)-1H-indazol-3-yl)-4,5,6,7-tetrahydro-3H-imidazo[4,5-c]pyridine-6-carboxylic acid

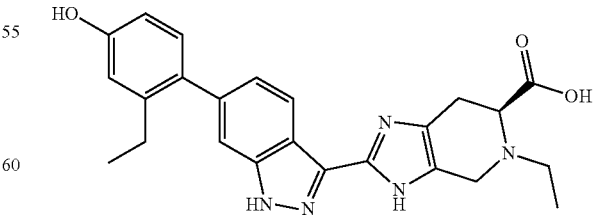

(S)-2-(6-(2-ethyl-4-hydroxyphenyl)-1H-indazol-3-yl)-4,5,6,7-tetrahydro-3H-imidazo[4,5-c]pyridine-6-carboxylic acid, HCl (0.100 g, 0.227 mmol) (I-18) and acetaldehyde (0.019 mL, 0.341 mmol) were dissolved in methanol (3.0 mL), then sodium cyanoborohydride (0.057 g, 0.909 mmol) was added and the reaction mixture was stirred at room temperature for 16 hours (reaction progress was monitored by LCMS). Sodium borohydride (9 mg, 0.227 mmol) was added to quench any remaining acetaldehyde, then the reaction mixture was concentrated. The crude product was then purified by reverse phase chromatography (5-70% ACN/Water gradient, 40 g C18 column) to provide the TFA salt of the title compound (62 mg, 50% yield). (m/z): [M+H]+ calcd for $C_{24}H_{25}N_5O_3$ 432.20 found 432.1.

Example 2: (S)-(3-(dimethylamino)azetidin-1-yl)(5-ethyl-2-(6-(2-ethyl-4-hydroxyphenyl)-1H-indazol-3-yl)-4,5,6,7-tetrahydro-3H-imidazo[4,5-c]pyridin-6-yl)methanone

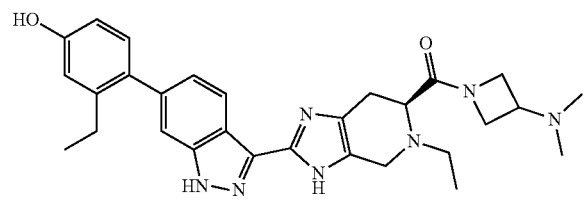

2

(S)-5-ethyl-2-(6-(2-ethyl-4-hydroxyphenyl)-1H-indazol-3-yl)-4,5,6,7-tetrahydro-3H-imidazo[4,5-c]pyridine-6-carboxylic acid, TFA (30 mg, 0.055 mmol), 3-(dimethylamino) azetidine dihydrochloride (14.28 mg, 0.082 mmol), and DIPEA (0.048 mL, 0.275 mmol) were dissolved in DMF (1.50 mL), then HATU (31.4 mg, 0.082 mmol) was added and the reaction mixture was stirred at room temperature for 1 hour (reaction progress was monitored by LCMS). Hydrazine (5.18 µl, 0.165 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (25 mg, 63% yield). (m/z): [M+H]+ calcd for $C_{29}H_{35}N_7O_2$ 514.29 found 514.2.

Example 3: (S)-(3-(dimethylamino)-3-methylazetidin-1-yl)(5-ethyl-2-(6-(2-ethyl-4-hydroxyphenyl)-1H-indazol-3-yl)-4,5,6,7-tetrahydro-3H-imidazo[4,5-c]pyridin-6-yl)methanone

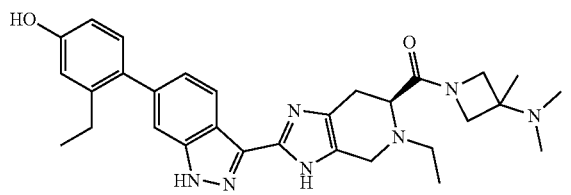

3

(S)-5-ethyl-2-(6-(2-ethyl-4-hydroxyphenyl)-1H-indazol-3-yl)-4,5,6,7-tetrahydro-3H-imidazo[4,5-c]pyridine-6-carboxylic acid, TFA (30 mg, 0.055 mmol), N,N,3-trimethyl-azetidin-3-amine hydrochloride (12.43 mg, 0.082 mmol), and DIPEA (0.048 mL, 0.275 mmol) were dissolved in DMF (1.50 mL), then HATU (31.4 mg, 0.082 mmol) was added and the reaction mixture was stirred at room temperature for 1 hour (reaction progress was monitored by LCMS). Hydrazine (5.18 µl, 0.165 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (25 mg, 62% yield). (m/z): [M+H]+ calcd for $C_{30}H_{37}N_7O_2$ 528.30 found 528.2.

Example 4: (S)-(3-(dimethylamino)-3-methylazetidin-1-yl)(2-(6-(2-ethyl-4-hydroxyphenyl)-1H-indazol-3-yl)-5-isopropyl-4,5,6,7-tetrahydro-3H-imidazo[4,5-c]pyridin-6-yl)methanone

4

(S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid (40 mg, 0.090 mmol) (I-19) N,N,3-trimethylazetidin-3-amine hydrochloride (20.29 mg, 0.135 mmol), and DIPEA (0.047 mL, 0.269 mmol) were dissolved in DMF (1.50 mL), then HATU (51.2 mg, 0.135 mmol) was added and the reaction mixture was stirred at room temperature for 16 hours (reaction progress was monitored by LCMS). Hydrazine (8.45 µl, 0.269 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (26 mg, 38% yield). (m/z): [M+H]+ calcd for $C_{31}H_{39}N_7O_2$ 542.32 found 542.2.

Preparation 7: (S)-2-(6-(2-ethyl-4-hydroxyphenyl)-1H-indazol-3-yl)-5-propyl-4,5,6,7-tetrahydro-3H-imidazo[4,5-c]pyridine-6-carboxylic acid (I-20)

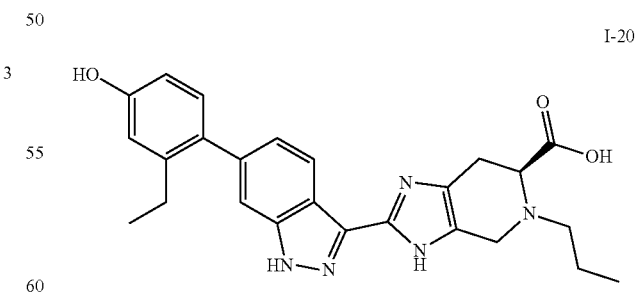

I-20

(S)-2-(6-(2-ethyl-4-hydroxyphenyl)-1H-indazol-3-yl)-4,5,6,7-tetrahydro-3H-imidazo[4,5-c]pyridine-6-carboxylic acid, HCl (I-18) (0.160 g, 0.364 mmol) and propionaldehyde (0.039 mL, 0.546 mmol) were dissolved in methanol (3.0 mL), then sodium cyanoborohydride (0.069 g, 1.091 mmol) was added and the reaction mixture was stirred at room temperature for 24 hours (reaction progress was monitored by LCMS). The reaction mixture was concentrated and the crude product was purified by reverse phase chromatography (5-70% ACN/Water gradient, 50 g C18 column) to provide the TFA salt of the title compound (78 mg, 38% yield). (m/z): [M+H]+ calcd for $C_{25}H_{27}N_5O_3$ 446.21 found 446.3.

Example 5: (S)-(3-(dimethylamino)azetidin-1-yl)(2-(6-(2-ethyl-4-hydroxyphenyl)-1H-indazol-3-yl)-5-propyl-4,5,6,7-tetrahydro-3H-imidazo[4,5-c]pyridin-6-yl)methanone

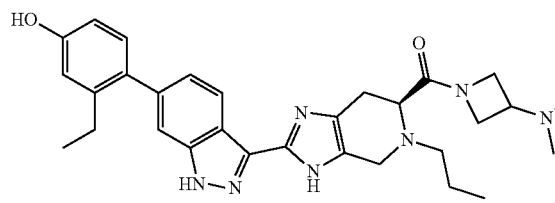

(S)-2-(6-(2-ethyl-4-hydroxyphenyl)-1H-indazol-3-yl)-5-propyl-4,5,6,7-tetrahydro-3H-imidazo[4,5-c]pyridine-6-carboxylic acid, TFA (30 mg, 0.054 mmol), (I-20) 3-(dimethylamino)azetidine dihydrochloride (13.92 mg, 0.080 mmol), and DIPEA (0.047 mL, 0.268 mmol) were dissolved in DMF (1.50 mL), then HATU (30.6 mg, 0.080 mmol) was added and the reaction mixture was stirred at room temperature for 1 hour (reaction progress was monitored by LCMS). Hydrazine (5.05 μl, 0.161 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (26 mg, 63% yield). (m/z): [M+H]+ calcd for $C_{30}H_{37}N_7O_2$ 528.30 found 528.2.

Example 6: (S)-(3-(dimethylamino)-3-methylazetidin-1-yl)(2-(6-(2-ethyl-4-hydroxyphenyl)-1H-indazol-3-yl)-5-propyl-4,5,6,7-tetrahydro-3H-imidazo[4,5-c]pyridin-6-yl)methanone

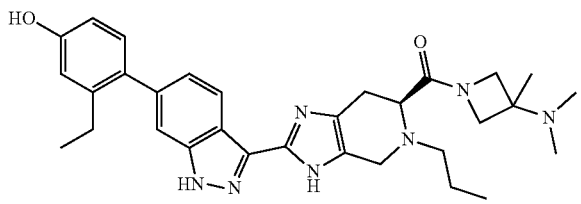

(S)-2-(6-(2-ethyl-4-hydroxyphenyl)-1H-indazol-3-yl)-5-propyl-4,5,6,7-tetrahydro-3H-imidazo[4,5-c]pyridine-6-carboxylic acid, TFA (30 mg, 0.054 mmol), (I-20) N,N,3-Trimethylazetidin-3-amine hydrochloride (12.12 mg, 0.080 mmol), and DIPEA (0.047 mL, 0.268 mmol) were dissolved in DMF (1.50 mL), then HATU (30.6 mg, 0.080 mmol) was added and the reaction mixture was stirred at room temperature for 1 hour (reaction progress was monitored by LCMS). Hydrazine (5.05 μl, 0.161 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (18 mg, 44% yield). (m/z): [M+H]+ calcd for $C_{31}H_{39}N_7O_2$ 542.32 found 542.2.

Preparation 8: 2-(4-(Benzyloxy)-2-ethyl-5-fluorophenyl)-4,4,5,5-tetramethyl-1,3,2-dioxaborolane

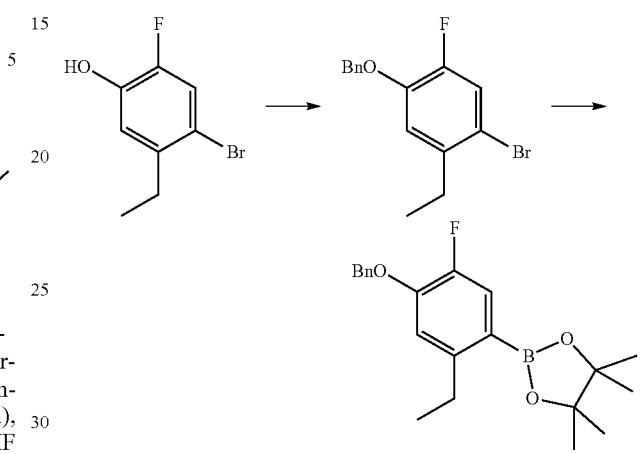

(a) 1-(Benzyloxy)-4-bromo-5-ethyl-2-fluorobenzene

To a solution of 4-bromo-5-ethyl-2-fluorophenol (20 g, 910.32 mmol) in ACN (250 mL) was added $K_2CO_3$ (31.55 g, 228.3 mmol) followed by benzyl bromide (13.10 mL, 109.58 mmol) drop wise. The resulting reaction mixture was stirred at 80° C. for 2 h. The aqueous layer was extracted with EtOAc (three times), combined and washed with brine. The organic layer was dried over $Na_2SO_4$ and evaporated under reduced pressure to afford the title intermediate as a pale yellow oily liquid (25 g, 89% yield). $^1$H NMR (400 MHz, Chloroform-d) δ 7.48-7.30 (m, 5H), 7.27 (d, J=10.5 Hz, 1H), 6.87 (d, J=8.7 Hz, 1H), 5.12 (s, 2H), 2.66 (q, J=7.5 Hz, 2H), 1.16 (t, J=7.5 Hz, 3H).

(b) 2-(4-(Benzyloxy)-2-ethyl-5-fluorophenyl)-4,4,5,5-tetramethyl-1,3,2-dioxaborolane To a solution of the product of the previous step (12.5 g, 40.45 mmol) in dioxane (100 mL) was added bis(pinacolato)diboron (15.40 g, 60.67 mmol) and KOAc (11.9 g, 121.35 mmol). The reaction mixture was purged with nitrogen for 15 min followed by addition of [1,1'-bis(diphenylphosphino)ferrocene]dichloropalladium(II), complex with dichloromethane (1.65 g, 2.023 mmol). The resulting reaction mixture was stirred and heated at 110° C. for 3 h, filtered through Celite and the residue washed with EtOAc. The filtrate was diluted with excess EtOAc (200 mL) and washed with water (100 mL) followed by brine (100 mL), dried over sodium sulfate and concentrated in vacuo to get crude product which was purified by column chromatography over (100-200) silica gel, eluted with 3-5% EtOAc:Hexane to afford the desired product as an off-white solid (9.50 g, 66% yield). $^1$H NMR (400 MHz, Chloroform-d) δ 7.54-7.27 (m, 6H), 6.81 (d, J=7.9 Hz, 1H), 5.16 (s, 2H), 2.84 (q, J=7.5 Hz, 2H), 1.32 (s, 12H), 1.14 (t, J=7.5 Hz, 3H).

Preparation 9: 6-(4-(benzyloxy)-2-ethyl-5-fluorophenyl)-1-(tetrahydro-2H-pyran-2-yl)-3-(trimethylstannyl)-1H-indazole

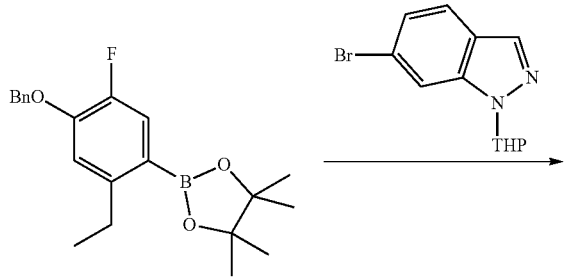

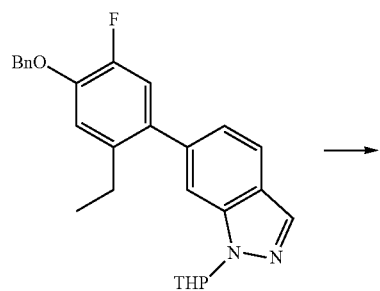

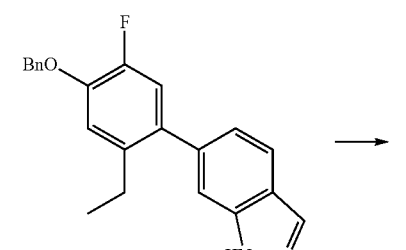

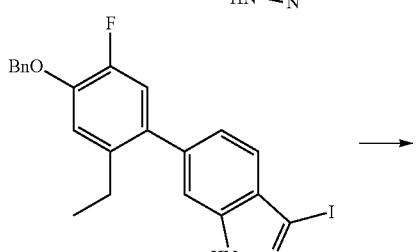

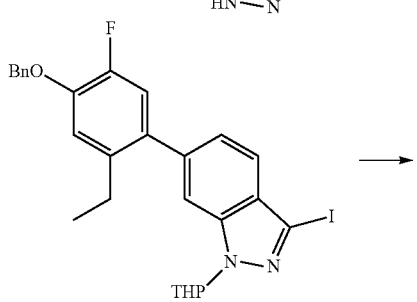

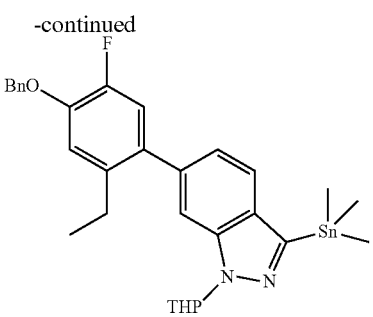

(a) 6-(4-(Benzyloxy)-2-ethyl-5-fluorophenyl)-1-(tetrahydro-2H-pyran-2-yl)-1H-indazole To a solution of 6-bromo-1-(tetrahydro-2H-pyran-2-yl)-1H-indazole (50 g, 178.57 mmol) and 2-(4-(benzyloxy)-2-ethyl-5-fluorophenyl)-4,4,5,5-tetramethyl-1,3,2-dioxaborolane (76.3 g, 214.29 mmol) in DMF:H$_2$O (480:120 mL) was added K$_3$PO$_4$ (94.64 g, 446.86 mmol). The reaction mixture was degassed with nitrogen for 15 min, then Pd(PPh$_3$)$_2$Cl$_2$ catalyst (6.26 g, 8.93 mmol) was added and the mixture was again degassed with nitrogen for 5 min stirred, and heated at 100-110° C. for 5 h. The reaction mixture was filtered through Celite and the residue was washed with EtOAc. The filtrate was diluted with EtOAc, washed with cold water and brine, dried over sodium sulfate and concentrated in vacuo to provide crude product which was purified by flash column chromatography to afford the title intermediate as a white solid (65 g, 86% yield). (m/z): [M+H]$^+$ calcd for C$_{27}$H$_{27}$FN$_2$O$_2$ 431.21 found 431.46. $^1$H NMR (400 MHz, Chloroform-d) δ 8.06-7.98 (m, 2H), 7.70 (d, J=8.2 Hz, 1H), 7.51-7.32 (m, 5H), 7.08 (dd, J=809.6, 8.3 Hz, 1H), 7.03 (d, J=11.9 Hz, 1H), 6.95 (d, J=8.5 Hz, 1H), 5.76-5.64 (m, 1H), 5.20 (s, 2H), 4.04 (d, J=10.1 Hz, 1H), 3.72 (t, J=9.7 Hz, 1H), 2.52 (q, J=7.5 Hz, 2H), 2.22-2.02 (m, 3H), 1.80-1.71 (m, 3H), 1.06 (t, J=7.5 Hz, 3H).

(b) 6-(4-(Benzyloxy)-2-ethyl-5-fluorophenyl)-1H-indazole

To a solution of the product of the previous step (65 g, 151.16 mmol) in methanol (700 mL) was added conc. HCl (120 mL) and the resulting solution was heated at 60-65° C. for 3 h, cooled to RT, and concentrated in vacuo. The residue was dissolved in EtOAc and washed with saturated NaHCO$_3$ aqueous solution and water. The organic layer was dried over anhydrous Na$_2$SO$_4$ and concentrated in vacuo to afford the title intermediate as a white solid (52 g, 99% (crude)). $^1$H NMR (400 MHz, Chloroform-d) δ 8.13 (s, 1H), 7.77 (d, J=8.3 Hz, 1H), 7.59-7.30 (m, 6H), 7.10 (d, J=8.3 Hz, 1H), 7.01 (d, J=11.8 Hz, 1H), 6.96 (d, J=8.4 Hz, 1H), 5.21 (s, 2H), 2.53 (q, J=7.5 Hz, 2H), 1.05 (t, J=7.5 Hz, 3H).

(c) 6-(4-(Benzyloxy)-2-ethyl-5-fluorophenyl)-3-iodo-1H-indazole

To a solution of 6-(4-(benzyloxy)-2-ethyl-5-fluorophenyl)-1H-indazole (56 g, 161.18 mmol) in DMF (400 mL) was added KOH (36.2 g, 647.39 mmol) and the mixture was stirred for 5 min. A solution of iodine (82.2 g, 323.69 mmol) in DMF (100 mL) was added slowly at 0° C. and stirred at RT for 30 min, diluted with water (3×150 mL) and extracted with EtOAc (3×200 mL). The organic layer was washed with saturated sodium metabisulfite aqueous solution (3×200 mL) and water (400 mL), dried over anhydrous Na₂SO₄ and concentrated under reduced pressure to get crude product which was purified by flash column chromatography to afford the title intermediate as a brownish semi-solid (64 g, 84% yield). ¹H NMR (400 MHz, Chloroform-d) δ 10.49 (s, 1H), 7.57-7.32 (m, 7H), 7.16 (d, J=8.3 Hz, 1H), 7.04-6.91 (m, 2H), 5.20 (s, 2H), 2.51 (q, J=7.4 Hz, 2H), 1.04 (t, J=7.5 Hz, 3H).

(d) 6-(4-(Benzyloxy)-2-ethyl-5-fluorophenyl)-3-iodo-1-(tetrahydro-2H-pyran-2-yl)-1H-indazole To an ice-cold solution of the product of the previous step (60 g, 127.12 mmol) in DCM (700 mL) was added p-toluensulfonic acid (4.84 g, 25.423 mmol) followed by 3,4-dihydro-2H-pyran (17.43 mL, 190.68 mmol) drop wise. The reaction mixture was stirred at RT overnight, diluted with DCM and washed with saturated NaHCO₃ aqueous solution and brine. The organic layer was dried over anhydrous Na₂SO₄ and concentrated under reduced pressure to provide crude product which was purified by flash chromatography (silica gel) to afford the title intermediate as an off white solid (64 g, 91% yield). (m/z): [M+H]⁺ calcd for C₂₇H₂₆FIN₂O₂ 557.10 found 557.30. ¹H NMR (400 MHz, Chloroform-d) δ 7.56-7.31 (m, 7H), 7.14 (d, J=8.3 Hz, 1H), 7.01 (d, J=11.8 Hz, 1H), 6.95 (d, J=8.5 Hz, 1H), 5.68 (d, J=9.3 Hz, 1H), 5.20 (s, 2H), 4.08-3.99 (m, 1H), 3.77-3.64 (m, 1H), 2.50 (q, J=7.2 Hz, 2H), 2.23-1.97 (m, 3H), 1.81-1.68 (m, 3H), 1.06 (t, J=7.4 Hz, 3H).

(e) 6-(4-(benzyloxy)-2-ethyl-5-fluorophenyl)-1-(tetrahydro-2H-pyran-2-yl)-3-(trimethylstannyl)-1H-indazole To a solution of 6-(4-(benzyloxy)-2-ethyl-5-fluorophenyl)-3-iodo-1-(tetrahydro-2H-pyran-2-yl)-1H-indazole (20 g, 35.97 mmol) in toluene (150 mL) was added hexamethylditin (9.2 mL, 43.17 mmol). The reaction mixture was degassed with nitrogen for 20 min followed by addition of tetrakis (2.0 g, 1.80 mmol) and then stirred at 100° C. for 2 h, cooled to RT, filtered through Celite and residue washed with EtOAc The filtrate was concentrated and purified by column chromatography (over neutral alumina), eluted with 2-5%. EtOAc:Hexane to afford the title compound (17.50 g, 82% yield). (m/z): [M+H]⁺ calcd for C₃₀H₃₅FN₂O₂Sn 595.17, 593.17 found 595.49, 593.55. ¹H NMR (400 MHz, Chloroform-d) δ 7.68 (d, J=8.0 Hz, 1H), 7.57-7.29 (m, 6H), 7.13-7.00 (m, 2H), 6.96 (d, J=8.4 Hz, 1H), 5.81-5.68 (m, 1H), 5.21 (s, 2H), 4.13-4.00 (m, 1H), 3.81-3.66 (m, 1H), 2.54 (q, J=7.3 Hz, 2H), 2.23-2.00 (m, 2H), 1.87-1.59 (m, 4H), 1.08 (t, J=7.5 Hz, 3H), 0.47 (s, 9H).

Preparation 10: 5-(tert-butyl) 6-methyl (S)-2-iodo-3-((2-trimethylsilyl)ethoxy) methyl)-3,4,6,7-tetrahydro-5H-imidazo[4,5-c]pyridine-5,6-dicarboxylate

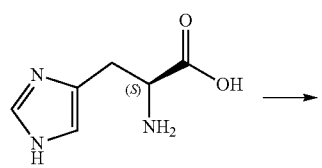

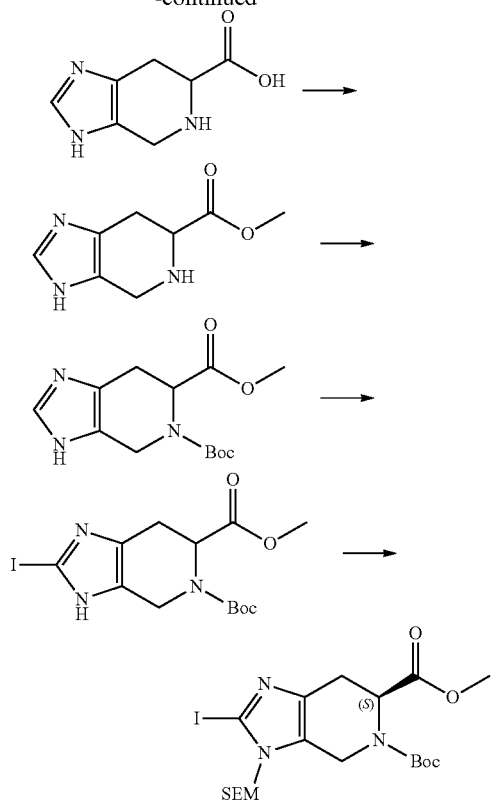

(a) (S)-4,5,6,7-Tetrahydro-3H-imidazo[4,5-c]pyridine-6-carboxylic acid

To a stirred suspension of L-histidine (50 g, 322.24 mmol) in water (420 mL) was added conc. HCl (29 mL) drop wise at 0° C. followed by formaldehyde (55 mL, 676.72 mmol) in one portion at 0° C. The resulting reaction mixture was stirred for 30 min and then heated at 75° C. for 6 h and concentrated. The resulting crude was stirred for 2 h with diethyl ether, filtered and washed with IPA:THF (100:300 mL) to provide the HCl salt of the title intermediate as an off white solid (75 g 99% yield (crude)). (m/z): [M+H]⁺ calcd for C₇H₉N₃O₂ 168.07 found 168.17.

(b) Methyl (S)-4,5,6,7-tetrahydro-3H-imidazo[4,5-c]pyridine-6-carboxylate

To a stirred solution of the product of the previous step (75.0 g, 312.5 mmol) in methanol (1500 mL) was added SOCl₂ (45.6 mL, 625 mmol) dropwise at 0° C. and stirred at RT for 16 h, then heated up to reflux (70° C.) for 1 h. The solvent was removed by distillation and the crude product was triturated with methanol followed by diethyl ether to provide the crude HCl salt of the title intermediate as an off white solid (80 g crude). ¹H NMR (400 MHz, DMSO-d₆) δ 9.05 (s, 1H), 4.71 (dd, J=9.4, 5.2 Hz, 1H), 4.36 (d, J=15.5 Hz, 1H), 4.30 (d, J=15.6 Hz, 1H), 3.82 (s, 3H), 3.44-3.21 (m, 2H).

(c) 5-(tert-Butyl) 6-methyl (S)-3,4,6,7-tetrahydro-5H-imidazo[4,5-c]pyridine-5,6-dicarboxylate To a stirred solution of the product of the previous step (80.0 g, 314.96 mmol) in methanol (1000 mL) was added DIPEA (282 mL, 1574 mmol) followed by di-tert-butyl dicarbonate (172 mL, 787.48 mmol) at 0° C. The reaction mixture was stirred at RT for 16 h and then liquid $NH_3$ (150 mL, 25% in water) was added and the reaction mixture was stirred again for 16 h at RT, methanol was removed by distillation and the residue was extracted in DCM (3×200 mL). Combined organic extracts were dried over anhydrous $Na_2SO_4$, concentrated and purified by flash chromatography (100-200 mesh silica gel), eluted with 5% MeOH:DCM to afford the title intermediate (41 g, 46%. yield). (m/z): $[M+H]^+$ calcd for $C_{13}H_{19}N_3O_4$ 282.14 found 282.21. $^1H$ NMR (400 MHz, DMSO-$d_6$) δ 11.85 (s, 1H), 7.50 (s, 1H), 5.18 (dd, J=49.3, 5.1 Hz, 1H), 4.51 (t, J=14.2 Hz, 1H), 4.09 (dd, J=43.9, 16.1 Hz, 1H), 3.59 (s, 3H), 3.08 (d, J=15.5 Hz, 1H), 2.94 (d, J=15.1 Hz, 1H), 1.45 (s, 9H).

(d) 5-(tert-Butyl) 6-methyl (S)-2-iodo-3,4,6,7-tetrahydro-5H-imidazo[4,5-c]pyridine-5,6-dicarboxylate To a solution of the product of the previous step (41.0 g, 145.9 mmol) in THF (500 mL) was added N-iodosuccinimide (66.0 g, 291.8 mmol) at 0° C. and the resulting solution was stirred at RT for 4 h, diluted with water and extracted with ethyl acetate. The organic portion was washed with 10% sodium thiosulphate solution (3×200 mL). The combined organic layer was dried over anhydrous sodium sulfate, and concentrated to provide the title compound 60 g (crude), which was used in the next step without further purification. (m/z): $[M+H]^+$ calcd for $C_{13}H_{18}IN_3O_4$ 408.03 found 408.31. $^1H$ NMR (400 MHz, DMSO-$d_6$) δ 12.48 (s, 1H), 5.34-4.97 (m, 1H), 4.67-4.35 (m, 1H), 4.12-3.95 (m, 1H), 3.60 (s, 3H), 3.14-2.82 (m, 2H), 1.44 (s, 9H).

(e) 5-(tert-Butyl) 6-methyl (S)-2-iodo-3-((2-trimethylsilyl)ethoxy) methyl)-3,4,6,7-tetrahydro-5H-imidazo[4,5-c]pyridine-5,6-dicarboxylate To a stirred solution of 5-(tert-butyl) 6-methyl (S)-2-iodo-3,4,6,7-tetrahydro-5H-imidazo[4,5-c]pyridine-5,6-dicarboxylate (40 g, 0.098 mol) in DMF (150 mL) was added DIPEA (35.1 mL, 0.19 mol) at 0° C. The reaction mixture was stirred for 10 min then 2-(trimethylsilyl)-ethoxymethyl chloride (19.1 mL, 0.10 mol) was added drop wise at 0° C. The resulting reaction mixture was stirred for 3 h at RT. After 4 h chilled water was added and the reaction mixture was extracted with EtOAc (2×200 mL). The organic layer was dried over anhydrous sodium sulphate, concentrated, and purified by flash column chromatography, eluted with 20-35% EtOAc:Hexane, to afford the title product as a pale yellow viscous liquid (27 g). (m/z): [M+H]+ calcd for $C_{19}H_{32}IN_3O_5Si$ 538.12 found 538.42. $^1H$ NMR (400 MHz, DMSO-$d_6$) δ 5.33-5.04 (m, 3H), 4.79-4.56 (m, 1H), 4.54-4.14 (m, 1H), 3.60 (s, 3H), 3.47 (t, J=7.8 Hz, 2H), 3.31-3.16 (m, 1H), 2.97 (t, J=18.9 Hz, 1H), 1.44 (s, 9H), 0.92-0.74 (m, 2H), −0.03 (s, 9H).

Preparation 11: (6S)-5-(tert-butoxycarbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic acid

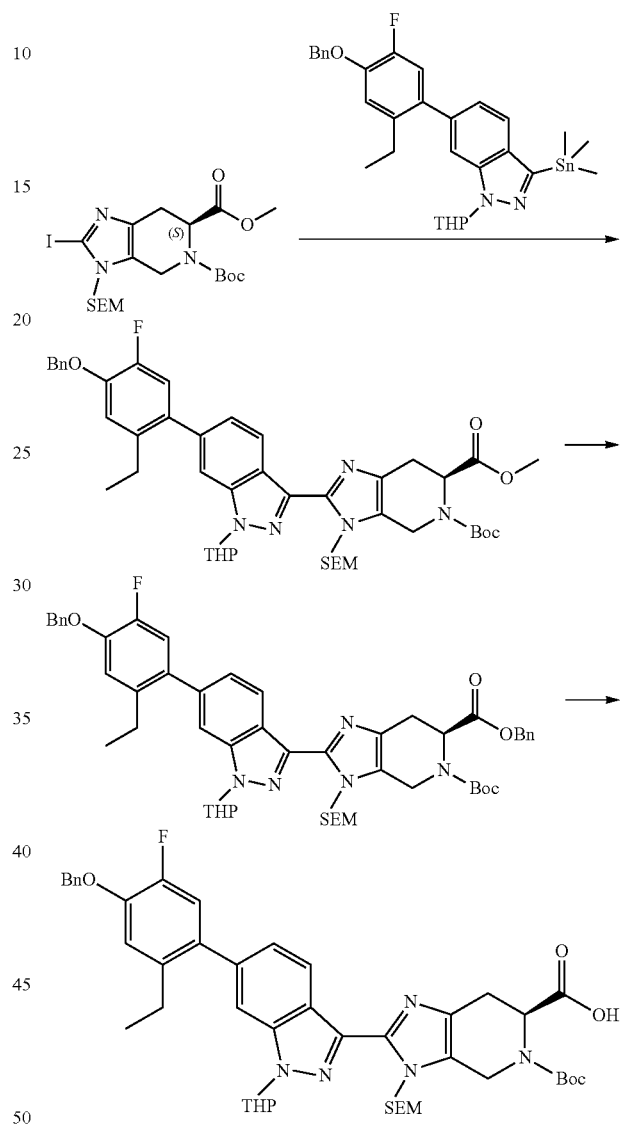

(a) 5-(tert-Butyl) 6-methyl (6S)-2-(6-(4-(benzyloxy)-2-ethyl-5-fluorophenyl)-1-(tetrahydro-2H-pyran-2-yl)-1H-indazol-3-yl)-3-((2-(trimethylsilyl) ethoxy) methyl)-3,4,6,7-tetrahydro-5H-imidazo[4,5-c]pyridine-5,6-dicarboxylate To a stirred solution of 5-(tert-butyl) 6-methyl (S)-2-iodo-3-((2-trimethylsilyl)ethoxy) methyl)-3,4,6,7-tetrahydro-5H-imidazo[4,5-c]pyridine-5,6-dicarboxylate (17.0 g, 31.65 mmol) in toluene (500 mL) was added 6-(4-(benzyloxy)-2-ethyl-5-fluorophenyl)-1-(tetrahydro-2H-pyran-2-yl)-3-(trimethylstannyl)-1H-indazole (20 g, 34.82 mmol). The reaction mixture was purged with argon for 15 min, Pd(PPh$_3$)$_4$ (3.6 g, 3.16 mmol) and copper iodide (1.20 g, 6.33 mmol) were added and the reaction mixture was stirred at 120° C. for 16 h. The reaction mixture was filtered through Celite, the filtrate was concentrated under reduced pressure and purified by silica gel column chromatography (Redisep 80 g column, eluted with DCM for 10 min and then 15-20% EtOAc in Hexane to afford the title intermediate as a yellow solid (15.10 g, 58% yield). (m/z): [M+H]$^+$ calcd for $C_{46}H_{58}FN_5O_7Si$ 840.41 found 840.54. $^1$H NMR (400 MHz, Chloroform-d) δ 8.43 (s, 1H), 7.54-7.33 (m, 6H), 7.20 (s, 1H), 7.05 (d, J=11.4 Hz, 1H), 6.95 (d, J=8.5 Hz, 1H), 6.09-5.69 (m, 3H), 5.59-5.36 (m, 1H), 5.20 (s, 2H), 4.97-4.80 (m, 1H), 4.12-3.90 (m, 1H), 3.68 (s, 3H), 3.57-3.47 (m, 2H), 3.40 (d, 1H), 3.21-3.05 (m, 1H), 2.74-2.34 (m, 4H), 2.25-2.07 (m, 2H), 1.94-1.65 (m, 4H), 1.54 (s, 9H), 1.12-0.99 (m, 3H), 0.91-0.75 (m, 2H), −0.12 (s, 9H).

(b) 6-Benzyl 5-(tert-butyl) (6S)-2-(6-(4-(benzyloxy)-2-ethyl-5-fluorophenyl)-1-(tetrahydro-2H-pyran-2-yl)-1H-indazol-3-yl)-3-((2-(trimethylsilyl)ethoxy)methyl)-3,4,6,7-tetrahydro-5H-imidazo[4,5-c]pyridine-5,6-dicarboxylate To a round bottom flask was added the product of the previous step (15.0 g, 17.85 mmol) in toluene (400 mL), benzyl alcohol (46.3 mL) and Ti(OEt)$_4$ (7.15 mL, 35.70 mmol) and the reaction mixture was refluxed vigorously (140° C.) for 48 h, diluted with water and extracted with DCM. The suspension was filtered, filtrate was dried over Na$_2$SO$_4$, concentrated under reduced pressure and purified by silica gel column chromatography (Redisep 80 g column, 0-5% EtOAc in hexanes) for 20 min to remove excess benzyl alcohol, then eluted with 10-15% EtOAc in Hexane) to provide the title intermediate. $^1$H NMR consistent with structure. (m/z): [M+H]$^+$ calcd for $C_{52}H_{62}FN_5O_7Si$ 916.44 found 916.86.

(c) (6S)-5-(tert-butoxycarbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)methyl)-4,5,6,7-tetrahydro-3H-imidazo[4,5-c]pyridine-6-carboxylic acid To a stirred solution of the product of the previous step (21.0 g, 22.92 mmol) in 1:1 IPA:THF (400 mL)) was added Pd(OH)$_2$ (5.0 g). The reaction mixture was stirred at RT for 16 h under a hydrogen balloon, filtered through Celite, concentrated under reduced pressure, and purified by silica gel column chromatography (Redisep 80 g column, eluted with 25-40% EtOAc in Hexane) to provide the title compound (6.1 g, 8.29 mmol) as an off-white solid. (m/z): [M+H]$^+$ calcd for $C_{38}H_{50}FN_5O_7Si$ 736.35 found 736.5. $^1$H NMR consistent with structure. (m/z): [M+H]$^+$ calcd for $C_{38}H_{50}FN_5O_7Si$ 736.35 found 736.5. $^1$H NMR (400 MHz, DMSO-d$_6$) δ 12.94 (s, 1H), 9.86 (s, 1H), 8.34 (t, J=7.6 Hz, 1H), 7.66 (s, 1H), 7.20 (d, J=8.7 Hz, 1H), 7.03 (d, J=11.8 Hz, 1H), 6.93 (d, J=9.1 Hz, 1H), 6.11-5.77 (m, 3H), 5.33-5.06 (m, 1H), 4.87-4.56 (m, 1H), 4.52-4.14 (m, 1H), 3.97-3.69 (m, 2H), 3.53-3.40 (m, 2H), 3.23-3.11 (m, 1H), 3.11-2.93 (m, 1H), 2.47-2.44 (m, 2H), 2.13-1.96 (m, 2H), 1.68 (d, J=70.9 Hz, 4H), 1.48 (s, 9H), 1.02 (t, J=7.5 Hz, 3H), 0.86-0.68 (m, 2H), −0.17 (s, 9H).

Preparation 12: (S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid

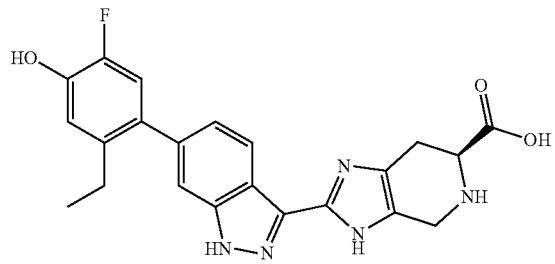 [SMILES: CCc1cc(O)c(F)cc1-c1ccc2c(-c3nc4c([nH]3)CN[C@H](C(=O)O)C4)n[nH]c2c1]

To a stirred solution of (6S)-5-(tert-butoxycarbonyl)-2-(6-(2-ethyl-5-fluoro-4-hydroxyphenyl)-1-(tetrahydro-2H-pyran-2-yl)-1H-indazol-3-yl)-3-((2-(trimethylsilyl)ethoxy)-methyl)-4,5,6,7-tetrahydro-3H-imidazo[4,5-c]pyridine-6-carboxylic acid (5.7 g, 7.75 mmol) in 5:1 dioxane:water (60 mL) was added conc. HCl (20 mL) drop wise at 0° C. The reaction mixture was warmed and stirred at 90° C. for 16 h and distilled under vacuum to provide the crude residue, which was sequentially triturated with chilled diethyl ether and acetonitrile to provide the HCl salt of the title compound (3.6 g. 95% yield) as a light brown solid. (m/z): [M+H]$^+$ calcd for $C_{22}H_{20}FN_5O_3$ 422.16 found 422.24. $^1$H NMR (400 MHz, D$_2$O/DMSO-d$_6$) δ 8.22 (d, J=8.4 Hz, 1H), 7.49 (s, 1H), 7.19 (d, J=8.1 Hz, 1H), 6.99 (d, J=11.9 Hz, 1H), 6.91 (d, J=9.0 Hz, 1H), 4.56-4.51 (m, 1H), 4.36 (d, J=15.5 Hz, 1H), 4.30 (d, J=15.5 Hz, 1H), 3.35-3.25 (m, 1H), 3.15-3.05 (m, 1H), 2.4-2.55 (m, 2H), 0.97 (t, J=7.5 Hz, 3H).

Preparation 13: (S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic acid

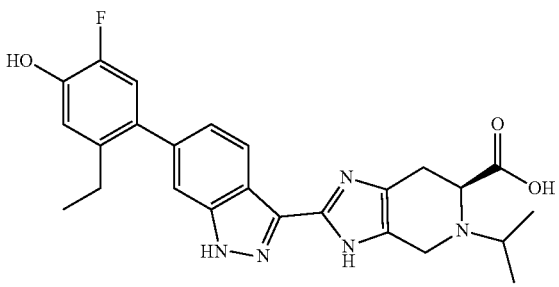 [SMILES: CCc1cc(O)c(F)cc1-c1ccc2c(-c3nc4c([nH]3)CN(C(C)C)[C@H](C(=O)O)C4)n[nH]c2c1]

To a solution of (S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, HCl (400 mg, 0.874 mmol), acetone (0.192 mL, 2.62 mmol), and acetic acid (0.150 mL, 2.62 mmol) in DMF (7 mL), was added sodium cyanoborohydride (274 mg, 4.37 mmol) and the reaction mixture was stirred at RT overnight. Sodium borohydride (33 mg, 0.874 mmol) was added, the solution was concentrated, and purified by preparative HPLC to provide the TFA salt of the title compound (115 mg, 23% yield). (m/z): [M+H]$^+$ calcd for $C_{25}H_{26}FN_5O_3$ 464.20 found 464.5.

Example 7: (S)-(3-(dimethylamino)azetidin-1-yl)(2-(6-(2-ethyl-5-fluoro-4-hydroxyphenyl)-1H-indazol-3-yl)-5-isopropyl-4,5,6,7-tetrahydro-3H-imidazo[4,5-c]pyridin-6-yl)methanone C-1

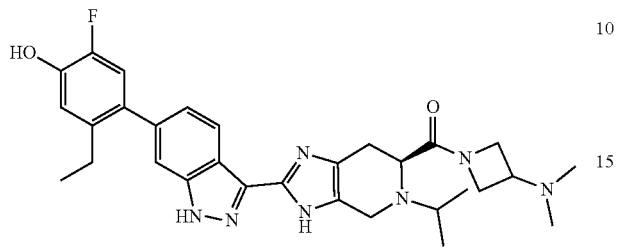

C-1

To a solution of (S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic acid, TFA (179 mg, 0.310 mmol), N,N-dimethylazetidin-3-amine, 2 HCl (107 mg, 0.465 mmol), and DIPEA (0.162 mL 0.930 mmol) in DMF (4 mL), was added HATU (177 mg, 0.465 mmol) and the reaction mixture was stirred at RT overnight. Hydrazine (5 eq) was added, the reaction mixture was concentrated and purified by preparative HPLC to provide the TFA salt of the title compound (63 mg, 26% yield). (m/z): [M+H]+ calcd for $C_{30}H_{36}FN_7O_2$ 546.29 found 546.7. $^1$H NMR (400 MHz, DMSO-$d_6$) δ 9.90 (s, 1H), 8.29 (dd, 1H), 7.34 (s, 1H), 7.07 (d, 1H), 7.01 (d, 1H), 6.89 (d, 1H), 4.35-4.18 (m, 1H), 4.11-3.94 (m, 1H), 3.94-3.73 (m, 3H), 3.70-3.57 (m, 2H), 3.06-2.94 (m, 2H), 2.87-2.66 (m, 2H), 2.48-2.40 (m, 2H), 2.13-2.00 (m, 6H), 1.07 (t, 3H), 1.03-0.93 (m, 6H).

Example 8: (S)-(3-(dimethylamino)-3-methylazetidin-1-yl)(2-(6-(2-ethyl-5-fluoro-4-hydroxyphenyl)-1H-indazol-3-yl)-5-isopropyl-4,5,6,7-tetrahydro-3H-imidazo[4,5-c]pyridin-6-yl)methanone

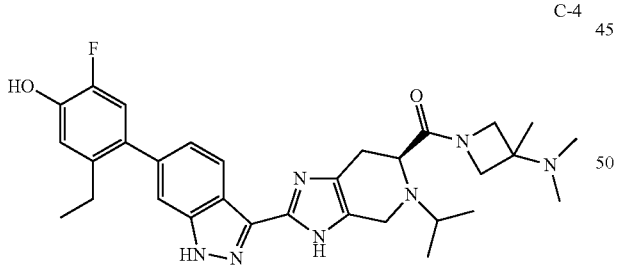

C-4

(S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic acid, TFA (30 mg, 0.052 mmol), N,N,3-trimethylazetidin-3-amine, 2HCl (29.2 mg, 0.156 mmol), and DIPEA (0.045 mL, 0.260 mmol) were dissolved in DMF (1.0 mL), then HATU (29.6 mg, 0.078 mmol) was added and the reaction mixture was stirred at room temperature for 20 hours (reaction progress was monitored by LCMS). Hydrazine (4.90 µl, 0.156 mmol) was added to cleave undesired byproducts, then the solution was stirred at room temperature for 10 minutes. The reaction mixture was then concentrated and the crude product was purified by preparative HPLC (2-70% ACN/Water gradient, C18 column) to provide the TFA salt of the title compound (13 mg, 33% yield). (m/z): [M+H]+ calcd for $C_{31}H_{38}FN_7O_2$ 560.31 found 560.2.

Preparation 14: (S)-5-ethyl-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid

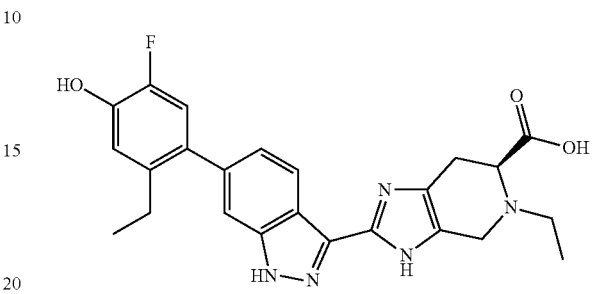

(S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, HCl (450 mg, 0.983 mmol) and acetaldehyde (0.083 mL, 1.474 mmol) were dissolved in DMF (7 mL), then sodium cyanoborohydride (247 mg, 3.93 mmol) was added and the reaction mixture was stirred at room temperature for 24 hours (reaction progress was monitored by LCMS). Sodium borohydride (112 mg, 2.95 mmol) was added to quench any remaining acetaldehyde, then the reaction mixture was concentrated. The crude product was then purified by reverse phase chromatography (5-65% ACN/Water gradient, 100 g C18 aq column) to provide the TFA salt of the title compound (165 mg, 30% yield). (m/z): [M+H]+ calcd for $C_{24}H_{24}FN_5O_3$ 450.19 found 450.2.

Example 9: (S)-(3-(dimethylamino)azetidin-1-yl)(5-ethyl-2-(6-(2-ethyl-5-fluoro-4-hydroxyphenyl)-1H-indazol-3-yl)-4,5,6,7-tetrahydro-3H-imidazo[4,5-c]pyridin-6-yl)methanone

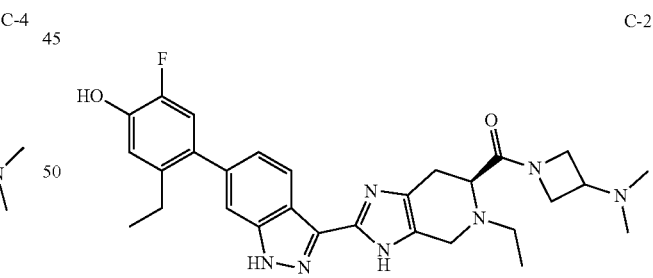

C-2

(S)-5-ethyl-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, TFA (30 mg, 0.053 mmol) and HATU (30.4 mg, 0.080 mmol) were combined in DMF (1.0 mL). To the solution, N,N-dimethylazetidin-3-amine (16 mg, 0.160 mmol) and DIPEA (0.037 mL, 0.213 mmol) were added and the reaction mixture was stirred at room temperature for 6 hours (reaction progress was monitored by LCMS). Hydrazine (4.92 µl, 0.160 mmol) was added to cleave undesired byproducts, then the solution was stirred at room temperature for 10 minutes. The reaction mixture was then concentrated and the crude product was purified by preparative HPLC (10-70% ACN/Water gradient, Zorbax Bonus-RP column) to provide the TFA salt of the title compound (27 mg, 67% yield). (m/z): [M+H]+ calcd for $C_{29}H_{34}FN_7O_2$ 532.28 found 532.2.

Example 10: (S)-(3-(dimethylamino)-3-methylazetidin-1-yl)(5-ethyl-2-(6-(2-ethyl-5-fluoro-4-hydroxyphenyl)-1H-indazol-3-yl)-4,5,6,7-tetrahydro-3H-imidazo[4,5-c]pyridin-6-yl)methanone

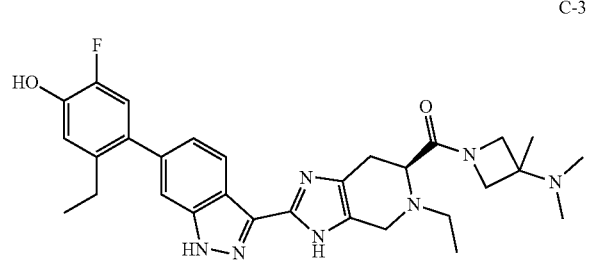 [SMILES: CCc1cc(O)c(F)cc1-c1ccc2c(-c3nc4c([nH]3)CN(CC)[C@H](C(=O)N3CC(C)(N(C)C)C3)C4)n[nH]c2c1]

C-3

(S)-5-ethyl-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, TFA (30 mg, 0.053 mmol) and HATU (30.4 mg, 0.080 mmol) were combined in DMF (1.0 mL). To the solution, N,N,3-trimethylazetidin-3-amine (18 mg, 0.160 mmol) and DIPEA (0.037 mL, 0.213 mmol) were added and the reaction mixture was stirred at room temperature for 6 hours (reaction progress was monitored by LCMS). Hydrazine (4.92 μl, 0.160 mmol) was added to cleave undesired byproducts, then the solution was stirred at room temperature for 10 minutes. The reaction mixture was then concentrated and the crude product was purified by preparative HPLC (10-70% ACN/Water gradient, Zorbax Bonus-RP column) to provide the TFA salt of the title compound (28 mg, 68% yield). (m/z): [M+H]+ calcd for $C_{30}H_{36}FN_7O_2$ 546.29 found 546.2.

Preparation 15: (S)-2-(6-(2-ethyl-5-fluoro-4-hydroxyphenyl)-1H-indazol-3-yl)-5-propyl-4,5,6,7-tetrahydro-3H-imidazo[4,5-c]pyridine-6-carboxylic acid

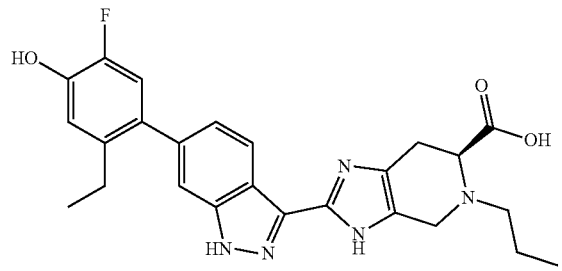 [SMILES: CCCN1Cc2[nH]c(-c3n[nH]c4cc(-c5cc(F)c(O)cc5CC)ccc34)nc2C[C@H]1C(=O)O]

(S)-2-(6-(2-ethyl-5-fluoro-4-hydroxyphenyl)-1H-indazol-3-yl)-4,5,6,7-tetrahydro-3H-imidazo[4,5-c]pyridine-6-carboxylic acid, HCl (300 mg, 0.655 mmol) and propionaldehyde (0.071 mL, 0.983 mmol) were dissolved in DMF (7 mL), then sodium cyanoborohydride (124 mg, 1.966 mmol) was added and the reaction mixture was stirred at room temperature for 72 hours (reaction progress was monitored by LCMS). Sodium borohydride (26 mg, 0.655 mmol) was added to quench any remaining aldehyde, then the reaction mixture was concentrated. The crude product was then purified by preparative HPLC (2-70% ACN/Water gradient, C18 column) to provide the TFA salt of the title compound (117 mg, 31% yield). (m/z): [M+H]+ calcd for $C_{25}H_{26}FN_5O_3$ 464.21 found 464.2.

Example 11: (S)-(3-(dimethylamino)azetidin-1-yl)(2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)methanone

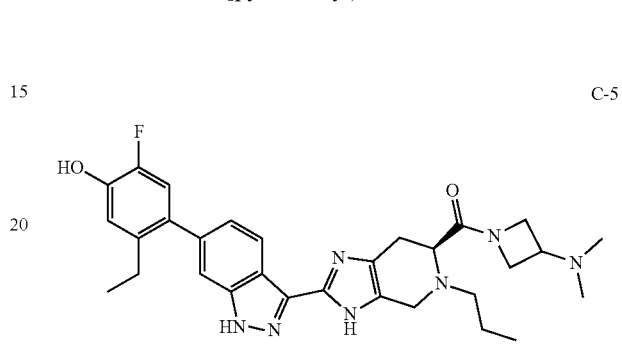

C-5

(S)-2-(6-(2-ethyl-5-fluoro-4-hydroxyphenyl)-1H-indazol-3-yl)-5-propyl-4,5,6,7-tetrahydro-3H-imidazo[4,5-c]pyridine-6-carboxylic acid, TFA (33 mg, 0.057 mmol), N,N-dimethylazetidin-3-amine, 2HCl (29.7 mg, 0.171 mmol), and DIPEA (0.060 mL, 0.343 mmol) were dissolved in DMF (2.0 mL), then HATU (28.2 mg, 0.074 mmol) was added and the reaction mixture was stirred at room temperature for 18 hours (reaction progress was monitored by LCMS). Hydrazine (8.97 μl, 0.286 mmol) was added to cleave undesired byproducts, then the solution was stirred at room temperature for 10 minutes. The reaction mixture was then concentrated and the crude product was purified by preparative HPLC (2-70% ACN/Water gradient, C18 column) to provide the TFA salt of the title compound (27 mg, 61% yield). (m/z): [M+H]+ calcd for $C_{30}H_{36}FN_7O_2$ 546.29 found 546.5.

Example 12: (S)-(3-(dimethylamino)-3-methylazetidin-1-yl)(2-(6-(2-ethyl-5-fluoro-4-hydroxyphenyl)-1H-indazol-3-yl)-5-propyl-4,5,6,7-tetrahydro-3H-imidazo[4,5-c]pyridin-6-yl)methanone

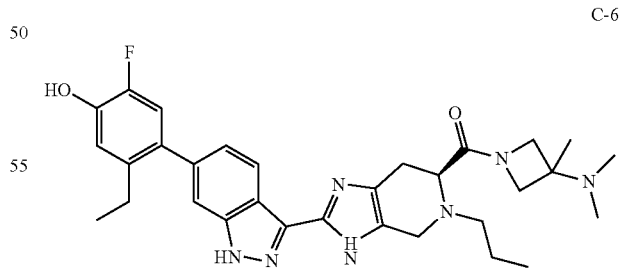

C-6

(S)-2-(6-(2-ethyl-5-fluoro-4-hydroxyphenyl)-1H-indazol-3-yl)-5-propyl-4,5,6,7-tetrahydro-3H-imidazo[4,5-c]pyridine-6-carboxylic acid, TFA (30 mg, 0.052 mmol), N,N,3-trimethylazetidin-3-amine, 2HCl (29.2 mg, 0.156 mmol), and DIPEA (0.045 mL, 0.260 mmol) were dissolved in DMF (1.0 mL), then HATU (29.6 mg, 0.078 mmol) was added and the reaction mixture was stirred at room temperature for 20 hours (reaction progress was monitored by LCMS). Hydrazine (8.89 µl, 0.260 mmol) was added to cleave undesired byproducts, then the solution was stirred at room temperature for 10 minutes. The reaction mixture was then concentrated and the crude product was purified by preparative HPLC (2-70% ACN/Water gradient, C18 column) to provide the TFA salt of the title compound (15 mg, 37% yield). (m/z): [M+H]+ calcd for $C_{31}H_{38}FN_7O_2$ 560.31 found 560.5.

Biological Assays

The compounds of the invention have been characterized in one or more of the following biological assays.

Assay 1: Biochemical JAK Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 µL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 µM, 3 µM, 1.6 µM, and 10 µM; while the substrate concentration is 200 nM for all four assays. Kinase reactions were allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to $pK_i$ (negative logarithm of dissociation constant, Ki) using the Cheng-Prusoff equation.

Test compounds having a lower $K_i$ value or higher $pK_i$ value in the four JAK assays show greater inhibition of JAK activity.

Assay 2: Inhibition of IL-2 Stimulated pSTAT5 in Tall-1 T Cells

The potency of test compounds for inhibition of interleukin-2 (IL-2) stimulated STAT5 phosphorylation was measured in the Tall-1 human T cell line (DSMZ) using AlphaLisa. Because IL-2 signals through JAK1/3, this assay provides a measure of JAK1/3 cellular potency.

Phosphorylated STAT5 was measured via the AlphaLISA SureFire Ultra pSTAT5 (Tyr694/699) kit (PerkinElmer).

Human T cells from the Tall-1 cell line were cultured in a 37° C., 5% $CO_2$ humidified incubator in RPMI (Life Technologies) supplemented with 15% Heat Inactivated Fetal Bovine Serum (FBS, Life Technologies), 2 mM Glutamax (Life Technologies), 25 mM HEPES (Life Technologies) and 1× Pen/Strep (Life Technologies). Compounds were serially diluted in DMSO and dispensed acoustically to empty wells. Assay media (phenol red-free DMEM (Life Technologies) supplemented with 10% FBS (ATCC)) was dispensed (4 µL/well) and plates shaken at 900 rpm for 10 mins. Cells were seeded at 45,000 cells/well in assay media (4 µL/well), and incubated at 37° C., 5% $CO_2$ for 1 hour, followed by the addition of IL-2 (R&D Systems; final concentration 300 ng/mL) in pre-warmed assay media (4 µL) for 30 minutes. After cytokine stimulation, cells were lysed with 6 ul of 3× AlphaLisa Lysis Buffer (PerkinElmer) containing 1× PhosStop and Complete tablets (Roche). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 µL) under green filtered <100 lux light. Plates were shaken at 900 rpm for 2 mins, briefly spun down, and incubated for 2 hrs at RT in the dark. Donor beads were dispensed (5 µL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in a human T cell line. $IC_{50}$ values were determined from analysis of the inhibition curves of signal intensity versus compound concentration. Data are expressed as $pIC_{50}$ (negative decadic logarithm $IC_{50}$) values (mean±standard deviation).

In Vitro Assay Results

TABLE 1

| Example Number | JAK1 $pK_i$ | JAK2 $pK_i$ | JAK3 $pK_i$ | Tyk2 $pK_i$ | Tall-1 pIC50 |
|---|---|---|---|---|---|
| 1   | 10.2 | 10.5 | 10.2 | 9.1 | 8.6 |
| C-1 | 10.4 | 10.8 | 10.1 | 9.5 | 8.8 |
| 2   | 10.3 | 10.7 | 10.3 | 9.2 | 8.7 |
| C-2 | 10.2 | 10.9 | 9.5  | 9.4 | 8.7 |
| 3   | 10.4 | 10.6 | 10.2 | 9.1 | 8.6 |
| C-3 | 10.3 | 10.9 | 9.7  | 9.4 | 8.7 |
| 4   | 10.0 | 10.8 | 9.9  | 9.1 | 8.7 |
| C-4 | 10.1 | 10.9 | 9.5  | 9.4 | 8.6 |
| 5   | 10.5 | 10.6 | 10.3 | 9.0 | 8.7 |
| C-5 | 10.1 | 10.8 | 10.0 | 9.4 | 8.7 |
| 6   | 10.3 | 10.5 | 9.8  | 9.0 | 8.6 |
| C-6 | 10.3 | 10.7 | 10.0 | 9.3 | 8.6 |

Assay 3: Murine (Mouse) Model of IL-13 Induced pSTAT6 Induction in Lung Tissue

IL-13 is an important cytokine underlying the pathophysiology of asthma (Kudlacz et al. *Eur. J. Pharmacol*, 2008, 582, 154-161). IL-13 binds to cell surface receptors activating members of the Janus family of kinases (JAK) which then phosphorylate STAT6 and subsequently activates further transcription pathways. In the described model, a dose of IL-13 was delivered locally into the lungs of mice to induce the phosphorylation of STAT6 (pSTAT6) which is then measured as the endpoint.

Adult Balb/c mice from Harlan were used in the assay. On the day of study, animals were lightly anesthetized with isoflurane and administered either vehicle or test compound (1 mg/mL, 50 µL total volume over several breaths) via oral aspiration. Animals were placed in lateral recumbency post dose and monitored for full recovery from anesthesia before being returned to their home cage. Four hours later, animals were once again briefly anesthetized and challenged with either vehicle or IL-13 (0.03 µg total dose delivered, 50 µL total volume) via oral aspiration before being monitored for recovery from anesthesia and returned to their home cage. One hour after vehicle or IL-13 administration, whole blood and lungs were collected for both pSTAT6 detection in lung homogenates using a Perkin Elmer AlphaLISA® SureFire® Ultra™ HV p-STAT6 (Tyr641) assay kit and for total drug concentration analysis in both lung and plasma. Blood samples were centrifuged (Eppendorf centrifuge, 5804R) for 4 minutes at approximately 12,000 rpm at 4° C. to collect plasma. Lungs were rinsed in DPBS (Dulbecco's Phosphate-Buffered Saline), padded dry, flash frozen, weighed, and homogenized at a dilution of 1:3 in 0.1% formic acid in HPLC water. Plasma and lung levels of test compound were determined by LC-MS analysis against analytical standards constructed into a standard curve in the test matrix. A lung to plasma ratio was determined as the ratio of the lung concentration in ng/g to the plasma concentration in ng/mL at 5 hours.

Activity in the model is evidenced by a decrease in the level of pSTAT6 present in the lungs of treated animals at 5 hours compared to the vehicle treated, IL-13 challenged control animals. The difference between the control animals which were vehicle-treated, IL-13 challenged and the control animals which were vehicle-treated, vehicle challenged dictated the 0% and 100% inhibitory effect, respectively, in any given experiment. The compounds tested in the assay exhibited inhibition of STAT6 phosphorylation at 5 hours after IL-13 challenge as documented below.

TABLE 2 pSTAT6 Inhibition and Plasma/Lung Exposure Observed

| Compound | Lung Concentration (ng/g) at 5 hr | Plasma Concentration (ng/mL) at 5 hr | Lung to Plasma ratio at 5 hr | pSTAT6 inhibition at 5 hours |
|---|---|---|---|---|
| 1 | 10155 ± 1979 | 24.0 ± 16.2 | 423 | 75 |
| 2 | 7750 ± 1652 | 23 ± 6 | 339 | 72 |
| 3 | 5130 ± 2205 | 24 ± 6 | 216 | 73 |
| 4 | 15000 ± 3349 | 55 ± 21 | 271 | 72 |
| 5 | 6940 ± 4248 | 25 ± 9 | 281 | 55 |
| 6 | 7465 ± 3084 | 23 ± 2.5 | 330 | 66 |

Observation of significant compound concentration in the mouse lung confirmed that the observed inhibition of IL-13 induced pSTAT6 induction was a result of the activity of the test compound. The lung to plasma ratio at 5 hours showed that compound 1 exhibited significantly more exposure in the lung than exposure in plasma in mice.

Assay 4: Inhibition of TSLP-Evoked TARC Release in Human Peripheral Blood Mononuclear Cells Thymic stromal lymphopoietin (TSLP) and thymus and activation-regulated chemokine (TARC) are overexpressed in asthmatic airways, and correlate with disease severity. In the lungs, TSLP may be released by bronchial epithelial cells in response to allergens and viral infections. TSLP signals through an IL-7Rα/TSLPR heterodimer found in a broad range of tissues and cell types, including epithelial cells, endothelial cells, neutrophils, macrophages, and mast cells. The binding of TSLP to its receptor induces a conformational change that activates JAK1 and JAK2 to phosphorylate various transcription factors, including STAT3 and STAT5. In immune cells, this triggers a cascade of intracellular events that result in cell proliferation, anti-apoptosis, dendritic cell migration, and production of Th2 cytokines and chemokines. In peripheral blood mononuclear cells (PBMC), TSLP has a proinflammatory effect by activating myeloid dendritic cells to attract and stimulate T cells, a process mediated by the chemoattractant TARC.

In this assay, it was shown that TSLP stimulation induces TARC release from PBMCs, and that this response is attenuated in a dose-dependent manner upon treatment with compound. The potencies of the test compounds were measured for inhibition of TARC release.

PBMC aliquots (previously isolated from whole blood and frozen in aliquots at −80° C.) from 3 to 5 donors were thawed at 37° C. and added dropwise to 40 mL pre-warmed, sterile-filtered, complete RPMI media in 50 mL Falcon tubes. Cells were pelleted and resuspended in complete media at $2.24\times10^6$ cells/mL. Cells were seeded at 85 μL (190,000 cells) per well in a tissue culture treated 96-well flat bottom microplate. Cells were allowed to rest for 1 hour at 37° C. with 5% $CO_2$.

Compounds were received as 10 mM stock solutions in DMSO. 3.7-fold serial dilutions were performed to generate 9 concentrations of test compound in DMSO at 300× the final assay test concentration. 150-fold intermediate dilutions were performed in complete media to generate compound at 2× the final assay test concentration with 0.2% DMSO. After the 1 hour rest period, 95 μL of 2× compound was added to each well of PBMC, for a final assay concentration range of 33.33 μM to 0.95 μM. 95 μL of 0.2% DMSO in complete media was added to the untreated control wells. Cells were pre-treated with compound for 1 hour at 37° C. with 5% $CO_2$ prior to stimulation.

Recombinant human TSLP protein was reconstituted at 10 μg/mL in sterile DPBS with 0.1% BSA and stored in aliquots at −20° C. Immediately prior to use, an aliquot was thawed and prepared at 20× the final assay concentration in complete media. 10 μL of 20×TSLP was added to each well of PBMC, for a final assay concentration of 10 ng/mL. 10 μL of complete media was added to the unstimulated control wells. Cells were stimulated in the presence of compound for 48 hours at 37° C. with 5% $CO_2$.

Following stimulation, the cell culture supernatants were harvested and TARC levels were detected by enzyme-linked immunosorbent assay (ELISA), using Human CCL17/TARC Quantikine ELISA Kit (R&D Systems #DDN00) according to the manufacturer's instructions.

For dose response analysis, the log [test compound (M)] was plotted versus the percent response values for each donor, and $IC_{50}$ values were determined using a nonlinear regression analysis with GraphPad Prism Software using the 4-parameter sigmoidal dose-response algorithm with variable slope. Data are expressed as mean $pIC_{50}$ (negative decadic logarithm $IC_{50}$) values calculated from $pIC_{50}$ values of individual donors and rounded to one decimal place. The potency values for inhibition by original compounds and their des-fluoro modified analogues are summarized in Table 3.

TABLE 3

Potency ($pIC_{50}$) Values of Test Compounds for Inhibition of TSLP-evoked TARC Release in Human Peripheral Blood Mononuclear Cells

| Compound | pIC50 ± st. dev. |
|---|---|
| 1 | 7.2 ± 0.1 |
| C-1 | 7.0 ± 0.1 |

Assay 5: Lung S9 Metabolism

The in vitro metabolic stability of compounds 1 and C-1 were evaluated in human lung S9 fraction (1 μM compound; 1 mg/mL S9 protein). The time 0, 15, 30, and 60 minute samples were analyzed for parent compound by high resolution LC-MS/MS. Lung S9 fractions from human (lot 1410245) were purchased from XenoTech LLC (Lenexa, Kans.). NADPH (Sigma Aldrich, N1630) and 3-phosphoadenosine 5-phosphosulfate (PAPS) (Sigma Aldrich, A1651) were purchased from Sigma Aldrich (St. Louis, Mo.). Acetonitrile and water were obtained from VWR (Radnor, Pa.) and were of HPLC grade or better. Raloxifene and formic acid was purchased from Sigma Aldrich (St. Louis, Mo.). Lung S9 incubations were performed in a water bath at 37° C. in a 96-well polypropylene plate. Lung S9 solutions consisted of 100 mM potassium phosphate buffered to pH 7.4 (BD Biosciences, Woburn, Mass.) supplemented with 1 mM NADPH (Sigma-Aldrich, St. Louis, Mo.), 3 mM magnesium chloride (Sigma Aldrich, M1028) and in the presence of 100 µM PAPS (Sigma-Aldrich, St. Louis, Mo.) cofactor, with final incubation protein concentrations of 1 mg/mL. 10 mM DMSO stocks of Raloxifene (n=1) and compound (n=1) were diluted in buffer and spiked into the incubations to yield 1 µM substrate concentrations (0.001% DMSO v/v). Incubation volumes consisted of 400 µL and time points were taken at 0, 15, 30, and 60 minutes by the removal of a 70 µL aliquot and dilution into 140 µL acetonitrile (0% formic acid). All samples were centrifuged at 2250 g for 10 minutes at 5° C. Supernatant (504) was taken from the centrifuged samples and diluted into 100 µL HPLC water containing internal standard. The samples were run on a Dionex Ultimate 3000 Auto sampler and analyzed using a Thermo Q-Exactive High Resolution Mass Spectrometer (Thermo, Waltham, Mass.) in Full Scan mode in conjunction with an Atlantis T3 column 3 µM-2.1×50 mm (Waters Inc., 186003717). Mobile Phase A consisted of Water+0.2% formic acid and Mobile Phase B consisted of acetonitrile +0.2% formic acid. Peak integration was accomplished using Gubbs GMSU software (Gubbs Inc., Alpharetta, Ga.). For each sample, peak area ratios were calculated by dividing the analyte peak area by the internal standard peak area. For each incubation, the peak area ratios of the analytes in each t0 was set to 100%, and the peak areas ratios from the 60 minute samples were converted to percentages remaining relative to the corresponding t0. Determination of sulfate metabolite formation was made qualitatively by observation of early-eluting peak in the parent ion channel which, based on historical internal data, corresponded to the O-sulfate metabolite of each parent compound. The results of the assay are summarized in Table 4 (n=2 replicate).

TABLE 4

Metabolic Stability in Human Lung S9 Fraction

| Compound | Clearance (µL/min/mg) | Compound Remaining at 60 min (%) | Sulfate Appearance |
|---|---|---|---|
| 1 | 3.5 | 81 | Yes |
| C-1 | 49.0 | 6 | Yes |
| 2 | 0.6 | 98 | Yes |
| C-2 | 46.7 | 6 | Yes |
| 3 | 0.8 | 97 | Yes |
| C-3 | 50.6 | 5 | Yes |
| 4 | 0.0 | 100 | Yes |
| C-4 | 53.2 | 4 | Yes |
| 5 | 1.6 | 96 | Yes |
| C-5 | 50.5 | 5 | Yes |
| 6 | 1.8 | 90 | Yes |
| C-6 | 53.5 | 4 | Yes |

When compared to their corresponding fluoro analog (compounds C-1 to C-6), compounds 1-6 gave rise to significantly less sulfation metabolism.

BD Biosciences) is used to detect STAT3 phosphorylation.

Assay 6: Pharmacokinetics in Plasma and Lung in Mouse

Plasma and lung concentrations of test compounds and ratios thereof were determined in the following manner. BALB/c mice from Charles River Laboratories were used in the assay. Test compounds were individually formulated in 20% propylene glycol in pH 4 citrate buffer at a concentration of 0.2 mg/mL and 50 µL of the dosing solution was introduced into the trachea of a mouse by oral aspiration. At various time points (typically 0.167, 2, 6, 24 hr) post dosing, blood samples were removed via cardiac puncture and intact lungs were excised from the mice. Blood samples were centrifuged (Eppendorf centrifuge, 5804R) for 4 minutes at approximately 12,000 rpm at 4° C. to collect plasma. Lungs were padded dry, weighed, and homogenized at a dilution of 1:3 in sterile water. Plasma and lung concentrations of test compound were determined by LC-MS analysis against analytical standards constructed into a standard curve in the test matrix. A lung-to-plasma ratio was determined as the ratio of the lung AUC in µg hr/g to the plasma AUC in µg hr/mL, where AUC is conventionally defined as the area under the curve of test compound concentration vs. time.

TABLE 5

Plasma and Lung Tissue Exposure Following a Single Oral Aspiration Administration of Test Compounds

| Compound | Plasma $AUC_{(0-24)}$ (µg hr/mL) | Lung Tissue $AUC_{(0-24)}$ (µg hr/g) | Lung Tissue:Plasma AUC ratio |
|---|---|---|---|
| 1 | 0.943 | 54.5 | 57.8 |

Assay 7: IL-5 Mediated Eosinophil Survival Assay

The potency of test compounds for IL-5 mediated eosinophil survival can be measured in human eosinophils isolated from human whole blood (AllCells). Because IL-5 signals through JAK, this assay provides a measure of JAK cellular potency.

Human eosinophils are isolated from fresh human whole blood (AllCells) of healthy donors. Blood is mixed with 4.5% Dextran (Sigma-Aldrich) in a 0.9% sodium chloride solution (Sigma-Aldrich). Red blood cells are left to sediment for 35 minutes. The leukocyte rich upper layer is removed and layered over Ficoll-Paque (GE Healthcare) and centrifuged at 600 g for 30 minutes. The plasma and mononuclear cell layers are removed before the granulocyte layer is lysed with water to remove any contaminating red blood cells. Eosinophils are further purified using a human eosinophil isolation kit (Miltenyi Biotec). A fraction of the purified eosinophils is incubated with anti-CD16 FITC (Miltenyi Biotec) for 10 minutes at 4° C. in the dark. Purity is analyzed using a LSRII flow cytometer (BD Biosciences).

Cells are cultured in a 37° C., 5% $CO_2$ humidified incubator in RPMI 1640 (Life Technologies) supplemented with 10% Heat Inactivated Fetal Bovine Serum (FBS, Life Technologies), 2 mM Glutamax (Life Technologies), 25 mM HEPES (Life Technologies) and 1× Pen/Strep (Life Technologies). Cells are seeded at 10,000 cells/well in media (50 µL). The plate is centrifuged at 300 g for 5 minutes and supernatants removed. Compounds are serially diluted in DMSO and then diluted another 500-fold to a 2× final assay concentration in media. Test compounds (50 µL/well) are added to cells, and incubated at 37° C., 5% $CO_2$ for 1 hour, followed by the addition of IL-5 (R&D Systems; final concentrations 1 ng/mL and 10 pg/mL) in pre-warmed assay media (50 µL) for 72 hours.

After cytokine stimulation, cells are centrifuged at 300 g for 5 min and washed twice with cold DPBS (Life Technologies). To access viability and apoptosis, cells are incubated with Propidium Iodide (Thermo Fisher Scientific) and APC Annexin V (BD Biosciences) and analyzed using a LSRII flow cytometer (BD Biosciences). $IC_{50}$ values are determined from analysis of the viability curves of percent cell viability vs compound concentration. Data are expressed as $pIC_{50}$ (negative decadic logarithm $IC_{50}$) values.

Assay 8: Inhibition of IFNγ and IL-27 Induced Chemokines CXCL9 and CXCL10 in Human 3D Airway Cultures EpiAirway tissue cultures were obtained from Mattek (AIR-100). Cultures were derived from asthmatic donors. In a cell culture insert, human derived tracheal/bronchial epithelial cells were grown and differentiated on a porous membrane support, allowing an air-liquid interface with warmed culture medium below the cells and a gaseous test atmosphere above. Tissues were cultured in maintenance media (Mattek, AIR-100-MM) in a 37° C., 5% $CO_2$ humidified incubator. Four donors were tested. On Day 0, tissue cultures were treated with test compounds in liquid interface at 10 µM, 1 µM and/or 0.1 µM. Compounds were diluted in dimethyl sulfoxide (DMSO, Sigma) to a final concentration of 0.1%. DMSO at 0.1% was used as a vehicle control. Test compounds were incubated with cultures for 1 hour at 37° C., 5% $CO_2$, followed by the addition of pre-warmed media containing IFNγ (R&D Systems) or IL-27 (R&D Systems) at a final concentration of 100 ng/ml. Tissue cultures were maintained for 8 days. Media was replaced every 2 days with fresh media containing compounds and IFNγ or IL-27. On Day 8, tissue cultures and supernatants were collected for analysis. Supernatant samples were assayed for CXCL10 (IP-10) and CXCL9 (MIG) using luminex analysis (EMD Millipore). Data is expressed as % Inhibition+/−standard deviation (±STDV). Percent inhibition was determined by compound inhibitory potency against IFNγ or IL-27 induced CXCL10 or CXCL9 secretion compared to vehicle treated cells. Data is the average from 4 donors. Compound 1 was able to inhibit IFNγ induced CXCL10 secretion by 100%±1.0 (at 10 µM), 76%±13 (at 1 µM) and 18%±22 (at 0.1 µM) when compared to vehicle control. Compound 1 was able to inhibit IFNγ induced CXCL9 secretion by 100%±0.1 (at 10 µM), 93%±6.9 (at 1 µM) and 16%±41 (at 0.1 µM) when compared to vehicle. Compound 1 was able to inhibit IL-27 induced CXCL10 secretion by 100%±0.0 (at 10 µM), 98%±1.0 (at 1 µM) and 25%±26 (at 0.1 µM) when compared to vehicle control. Compound 1 was able to inhibit IL-27 induced CXCL9 secretion by 100%±0.0 (at 10 µM), 97%±2.0 (at 1 µM) and 52%±18 (at 0.1 µM) when compared to vehicle control.

Assay 9: Cellular JAK Potency Assay: Inhibition of IL-2/Anti-CD3 Stimulated IFNγ in Human PBMCs The potency of the test compounds for inhibition of interleukin-2 (IL-2)/anti-CD3 stimulated interferon gamma (IFNγ) can be measured in human peripheral blood mononuclear cells (PBMCs) isolated from human whole blood (Stanford Blood Center). Because IL-2 signals through JAK, this assay provides a measure of JAK cellular potency.

(1) Human peripheral blood mononuclear cells (PBMC) are isolated from human whole blood of healthy donors using a ficoll gradient. Cells are cultured in a 37° C., 5% $CO_2$ humidified incubator in RPMI (Life Technologies) supplemented with 10% Heat Inactivated Fetal Bovine Serum (FBS, Life Technologies), 2 mM Glutamax (Life Technologies), 25 mM HEPES (Life Technologies) and 1× Pen/Strep (Life Technologies). Cells are seeded at 200,000 cells/well in media (50 µL) and cultured for 1 h. Compounds are serially diluted in DMSO and then diluted another 500-fold (to a 2× final assay concentration) in media. Test compounds (100 µL/well) are added to cells, and incubated at 37° C., 5% $CO_2$ for 1 h, followed by the addition of IL-2 (R&D Systems; final concentration 100 ng/mL) and anti-CD3 (BD Biosciences; final concentration 1 µg/mL) in pre-warmed assay media (50 µL) for 24 h.

(2) After cytokine stimulation, cells are centrifuged at 500 g for 5 min and supernatants removed and frozen at −80° C. To determine the inhibitory potency of the test compound in response to IL-2/anti-CD3, supernatant IFNγ concentrations are measured via ELISA (R&D Systems). $IC_{50}$ values are determined from analysis of the inhibition curves of concentration of IFNγ vs compound concentration. Data are expressed as $pIC_{50}$ (negative decadic logarithm $IC_{50}$) values.

Assay 10: Cellular JAK Potency Assay: Inhibition of IL-2 Stimulated pSTAT5 in CD4+ T Cells The potency of test compounds for inhibition of interleukin-2 (IL-2)/anti-CD3 stimulated STAT5 phosphorylation can be measured in CD4-positive (CD4+) T cells in human peripheral blood mononuclear cells (PBMCs) isolated from human whole blood (Stanford Blood Center) using flow cytometry. Because IL-2 signals through JAK, this assay provides a measure of JAK cellular potency.

CD4+ T cells are identified using a phycoerythrobilin (PE) conjugated anti-CD4 antibody (Clone RPA-T4, BD Biosciences), while an Alexa Fluor 647 conjugated anti-pSTAT5 antibody (pY694, Clone 47, BD Biosciences) is used to detect STAT5 phosphorylation.

(1) The protocol of Assay 9 paragraph (1) is followed with the exception that the cytokine stimulation with anti-CD3 is performed for 30 min instead of 24 h.

(2) After cytokine stimulation, cells are fixed with pre warmed fix solution (200 µL; BD Biosciences) for 10 min at 37° C., 5% $CO_2$, washed twice with DPBS buffer (1 mL, Life Technologies), and resuspended in ice cold Perm Buffer III (1000 µL, BD Biosciences) for 30 min at 4° C. Cells are washed twice with 2% FBS in DPBS (FACS buffer), and then resuspended in FACS buffer (100 µL) containing anti-CD4 PE (1:50 dilution) and anti-CD3 anti-CD3Alexa Fluor 647 (1:5 dilution) for 60 min at room temperature in the dark. After incubation, cells are washed twice in FACS buffer before being analyzed using a LSRII flow cytometer (BD Biosciences). To determine the inhibitory potency of test compounds in response to IL-2/anti-CD3, the median fluorescent intensity (MFI) of pSTAT5 is measured in CD4+ T cells. $IC_{50}$ values are determined from analysis of the inhibition curves of MFI vs compound concentration. Data are expressed as $pIC_{50}$ (negative decadic logarithm $IC_{50}$) values.

Assay 11: Cellular JAK Potency Assay: Inhibition of IL-4 Stimulated pSTAT6 in CD3+ T Cells The potency of test compounds for inhibition of interleukin-4 (IL-4) stimulated STAT6 phosphorylation can be measured in CD3-positive (CD3+) T cells in human peripheral blood mononuclear cells (PBMCs) isolated from human whole blood (Stanford Blood Center) using flow cytometry. Because IL-4 signals through JAK, this assay provides a measure of JAK cellular potency.

CD3+ T cells are identified using a phycoerythrobilin (PE) conjugated anti-CD3 antibody (Clone UCHT1, BD Biosciences), while an Alexa Fluor 647 conjugated antipSTAT6 antibody (pY641, Clone 18/P, BD Biosciences) is used to detect STAT6 phosphorylation.

Human peripheral blood mononuclear cells (PBMC) are isolated from human whole blood of healthy donors as in Assays 9 and 10. Cells are seeded at 250,000 cells/well in media (200 μL), cultured for 1 h and then resuspended in assay media (50 μL) (RPMI supplemented with 0.1% bovine serum albumin (Sigma), 2 mM Glutamax, 25 mM HEPES and 1× Penstrep) containing various concentrations of test compounds. Compounds are serially diluted in DMSO and then diluted another 500-fold (to a 2× final assay concentration) in assay media. Test compounds (50 μL) are incubated with cells at 37° C., 5% $CO_2$ for 1 h, followed by the addition of IL-4 (50 μL) (R&D Systems; final concentration 20 ng/mL) in pre-warmed assay media for 30 min. After cytokine stimulation, cells are fixed with pre-warmed fix solution (100 μL) (BD Biosciences) for 10 min at 37° C., 5% $CO_2$, washed twice with FACS buffer (1 mL) (2% FBS in DPBS), and resuspended in ice cold Perm Buffer III (1000 μL) (BD Biosciences) for 30 min at 4° C. Cells are washed twice with FACS buffer, and then resuspended in FACS buffer (100 μL) containing anti-CD3 PE (1:50 dilution) and anti-pSTAT6 Alexa Fluor 647 (1:5 dilution) for 60 min at room temperature in the dark. After incubation, cells are washed twice in FACS buffer before being analyzed using a LSRII flow cytometer (BD Biosciences).

To determine the inhibitory potency of the test compound in response to IL-4, the median fluorescent intensity (MFI) of pSTAT6 is measured in CD3+ T cells. $IC_{50}$ values are determined from analysis of the inhibition curves of MFI vs compound concentration. Data are expressed as $pIC_{50}$ (negative decadic logarithm $IC_{50}$).

Assay 12: Cellular JAK Potency Assay: Inhibition of IL-6 Stimulated pSTAT3 in CD3+ T Cells A protocol analogous to that of Assay 11 can be used to determine the potency of the test compound for inhibition of interleukin-6 (IL-6) stimulated STAT3 phosphorylation. An Alexa Fluor 647 conjugated anti-pSTAT3 antibody (pY705, Clone 4/P, BD Biosciences) is used to detect STAT3 phosphorylation.

Assay 13: Murine Model of *Alternaria alternata*-Induced Eosinophilic Inflammation of the Lung Airway eosinophilia is a hallmark of human asthma. *Alternaria alternata* is a fungal aeroallergen that can exacerbate asthma in humans and induces eosinophilic inflammation in the lungs of mice (Havaux et al. *Clin Exp Immunol.* 2005 February; 139(2):179-88). In mice, it has been demonstrated that alternaria indirectly activates tissue resident type 2 innate lymphoid cells in the lung, which respond to (e.g. IL-2 and IL-7) and release JAK-dependent cytokines (e.g. IL-5 and IL-13) and coordinate eosinophilic inflammation (Bartemes et al. *J Immunol.* 2012 Feb. 1; 188(3):1503-13).

Seven- to nine-week old male C57 mice from Taconic can be used in the study. On the day of study, animals are lightly anesthetized with isoflurane and administered either vehicle or test compound (0.03-1.0 mg/mL, 504 total volume over several breaths) via oropharyngeal aspiration. Animals are placed in lateral recumbency post dose and monitored for full recovery from anesthesia before being returned to their home cage. One hour later, animals are once again briefly anesthetized and challenged with either vehicle or alternaria extract (200 μg total extract delivered, 504 total volume) via oropharyngeal aspiration before being monitored for recovery from anesthesia and returned to their home cage. Forty-eight hours after alternaria administration, bronchoalveolar lavage fluid (BALF) is collected and eosinophils are counted in the BALF using the Advia 120 Hematology System (Siemens). Activity in the model is evidenced by a decrease in the level of eosinophils present in the BALF of treated animals at forty-eight hours compared to the vehicle treated, alternaria challenged control animals. Data are expressed as percent inhibition of the vehicle treated, alternaria challenged BALF eosinophils response. To calculate percent inhibition, the number of BALF eosinophils for each condition is converted to percent of the average vehicle treated, alternaria challenged BALF eosinophils and subtracted from one-hundred percent.

Assay 14: Cellular JAK Potency Assay: Inhibition of IFNγ-Induced pSTAT1

The potency of test compounds for inhibition of interferon gamma (IFNγ) stimulated STAT1 phosphorylation was measured in CD14-positive (CD14+) monocytes derived from human whole blood (Stanford Blood Center) using flow cytometry. Because IFNγ signals through JAK, this assay provides a measure of JAK cellular potency.

Monocytes were identified using a fluorescein isothiocyanate (FITC) conjugated anti-CD14 antibody (Clone RM052, Beckman Coulter), and an Alexa Fluor 647 conjugated anti-pSTAT1 antibody (pY701, Clone 4a, BD Biosciences) was used to detect STAT1 phosphorylation.

Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Fetal Bovine Serum (FBS, Life Technologies), 2 mM Glutamax (Life Technologies), 25 mM HEPES (Life Technologies) and 1× Pen/Strep (Life Technologies). Cells were seeded at 250,000 cells/well in media (200 μL), cultured for 2 h and re-suspended in assay media (50 μL) (RPMI supplemented with 0.1% bovine serum albumin (Sigma), 2 mM Glutamax, 25 mM HEPES and 1× Penstrep) containing various concentrations of test compound. The compound was serially diluted in DMSO and then diluted another 1000-fold in media to bring the final DMSO concentration to 0.1%. Test compound dilutions were incubated with cells at 37° C., 5% $CO_2$ for 1 h, followed by the addition of pre-warmed IFNγ (R&D Systems) in media (50 μL) at a final concentration of 0.6 ng/mL for 30 min. After cytokine stimulation, cells were fixed with pre-warmed fix solution (100 μL) (BD Biosciences) for 10 min at 37° C., 5% $CO_2$, washed twice with FACS buffer (1 mL) (1% BSA in PBS), re-suspended in 1:10 anti-CD14 FITC:FACS buffer (100 μL), and incubated at 4° C. for 15 min. Cells were washed once, and then re-suspended in ice cold Perm Buffer III (BD Biosciences) (100 μL) for 30 min at 4° C. Cells were washed twice with FACS buffer, and then re-suspended in 1:10 anti-pSTAT1 Alexa Fluor 647:FACS buffer (100 μL) for 30 min at RT in the dark, washed twice in FACS buffer, and analyzed using a MACSQuant flow cytometer (Miltenyi).

To determine the inhibitory potency of the test compound, the median fluorescent intensity (MFI) of pSTAT1 was measured in CD14+ monocytes. $IC_{50}$ values were determined from analysis of the inhibition curves of MFI vs compound concentration. Data are expressed as $pIC_{50}$ (negative decadic logarithm $IC_{50}$) values. Compound 1 exhibited a $pIC_{50}$ value of 7.5 in this assay.

Assay 15: Cellular JAK Potency Assay: Inhibition of GM-CSF-Induced pSTAT5

The potency of test compounds for inhibition of granulocyte-macropage colony-stimulating factor (GM-CSF) stimulated STAT5 phosphorylation was measured in CD14-positive (CD14+) monocytes derived from human whole blood (Stanford Blood Center) using flow cytometry. Because GM-CSF signals through JAK, this assay provides a measure of JAK cellular potency.

Monocytes were identified using a fluorescein isothiocyanate (FITC) conjugated anti-CD14 antibody (Clone RM052, Beckman Coulter), and an Alexa Fluor 647 conjugated anti-pSTAT5 antibody (pY694, BD Biosciences) was used to detect STAT5 phosphorylation.

Human peripheral blood mononuclear cells (PBMC) were isolated from human whole blood of healthy donors using a ficoll gradient. Cells were cultured in a 37° C., 5% $CO_2$ humidified incubator in RPMI (Life Technologies) supplemented with 10% Fetal Bovine Serum (FBS, Life Technologies), 2 mM Glutamax (Life Technologies), 25 mM HEPES (Life Technologies) and 1× Pen/Strep (Life Technologies). Cells were seeded at 250,000 cells/well in media (200 µL), cultured for 2 h and re-suspended in assay media (50 µL) (RPMI supplemented with 0.1% bovine serum albumin (Sigma), 2 mM Glutamax, 25 mM HEPES and 1× Penstrep) containing various concentrations of test compounds. The compound was serially diluted in DMSO and then diluted another 1000-fold in media to bring the final DMSO concentration to 0.1%. Test compound dilutions were incubated with cells at 37° C., 5% $CO_2$ for 1 h, followed by the addition of pre-warmed GM-CSF (R&D Systems) in media (50 µL) at a final concentration of 0.3 ng/mL for 15 min. After cytokine stimulation, cells were fixed with pre-warmed fix solution (100 µL) (BD Biosciences) for 10 min at 37° C., 5% $CO_2$, washed twice with FACS buffer (1 mL) (1% BSA in PBS), re-suspended in 1:10 anti-CD14 FITC: FACS buffer (100 µL), and incubated at 4° C. for 15 min. Cells were washed once, and then re-suspended in ice cold Perm Buffer III (BD Biosciences) (100 µL) for 30 min at 4° C. Cells were washed twice with FACS buffer, and then re-suspended in 1:10 anti-pSTAT1 Alexa Fluor 647:FACS buffer (100 µL) for 30 min at RT in the dark, washed twice in FACS buffer, and analyzed using a MACSQuant flow cytometer (Miltenyi).

To determine the inhibitory potency of the test compound, the median fluorescent intensity (MFI) of pSTAT5 was measured in CD14+ monocytes. $IC_{50}$ values were determined from analysis of the inhibition curves of MFI vs compound concentration. Data are expressed as $pIC_{50}$ (negative decadic logarithm $IC_{50}$) values. Compound 1 exhibited a $pIC_{50}$ value of 6.9 in this assay.

Assay 16: Cellular JAK Potency Assay: Inhibition of IL-12-Induced pSTAT4

The potency of test compounds for inhibition of interleukin-12 (IL-12) stimulated STAT4 phosphorylation was measured in CD3-positive (CD3+) T cells derived from human whole blood (Stanford Blood Center) using flow cytometry. Because IL-12 signals through JAK, this assay provides a measure of JAK cellular potency.

CD3+ T cells were identified using a phycoerythrin (PE) conjugated anti-CD3 antibody (clone UCHT1, BD Biosciences), and an Alexa Fluor 647 conjugated anti-pSTAT4 antibody (clone 38/p-Stat4, BD Biosciences) was used to detect STAT4 phosphorylation.

Human peripheral blood mononuclear cells (PBMC) were isolated from human whole blood of healthy donors using a ficoll gradient. Cells were cultured in RPMI (Life Technologies) supplemented with 10% Fetal Bovine Serum (FBS, Life Technologies), 2 mM Glutamax (Life Technologies), 25 mM HEPES (Life Technologies), 1× Pen/Strep (Life Technologies), plate bound purified anti-CD3 antibody (5 µg/ml, clone UCHT1, BD Biosciences) and soluble anti-CD28 antibody (1 µg/ml, clone CD28.2, BD Biosciences) for 3 days in a 37° C., 5% $CO_2$ humidified incubator. Cells were harvested, washed with media and then re-suspended in media containing interleukin-2 (IL-2, 10 ng/ml, R&D Systems). Cells were cultured for 3 days in a 37° C., 5% $CO_2$ humidified incubator. Cells were harvested, washed with RPMI and seeded at 250,000 cells/well in media (200 µL), cultured for 2 h and re-suspended in assay media (50 µL) (RPMI supplemented with 0.1% bovine serum albumin (Sigma), 2 mM Glutamax, 25 mM HEPES and 1× Penstrep) containing various concentrations of test compounds. The compound was serially diluted in DMSO and then diluted another 1000-fold in media to bring the final DMSO concentration to 0.1%. Test compound dilutions were incubated with cells at 37° C., 5% $CO_2$ for 1 h, followed by the addition of pre-warmed IL-12 (R&D Systems) in media (50 µL) at a final concentration of 10 ng/mL for 30 min. After cytokine stimulation, cells were fixed with pre-warmed fix solution (100 µL) (BD Biosciences) for 10 min at 37° C., 5% $CO_2$, washed twice with FACS buffer (1 mL) (1% BSA in PBS), and re-suspended in ice cold Perm Buffer III (1000 µL) (BD Biosciences) for 30 min at 4° C. Cells were washed twice with FACS buffer, and then re-suspended in FACS buffer (100 µL) containing anti-CD3 PE (1:50 dilution) and anti-pSTAT4 Alexa Fluor 647 (1:10 dilution) for 45 min at room temperature in the dark. After incubation, cells were washed twice in FACS buffer before being analyzed using a MACSQuant flow cytometer (Miltenyi). To determine the inhibitory potency of the test compound, the median fluorescent intensity (MFI) of pSTAT4 was measured in CD3+ T cells. $IC_{50}$ values were determined from analysis of the inhibition curves of MFI vs compound concentration. Data are expressed as $pIC_{50}$ (negative decadic logarithm $IC_{50}$) values. Compound 1 exhibited a $pIC_{50}$ value of 6.0 in this assay.

Assay 17: Inhibition of IFNγ Secretion in a Mixed Lymphocyte Reaction Assay

The mixed lymphocyte reaction assay is an in-vitro assay that mimics transplant rejection. T cells from one donor are cultured with allogeneic dendritic cells from another donor. This reaction induces a cellular immune response such as IFNγ secretion.

CD14+ monocytes were isolated from human whole blood (Stanford blood center) of donor A using a ficoll gradient and magnetic seperation (CD14 microbeads, Miltenyi). Monocytes were differentiated into dendritic cells by culturing cells in RPMI (Life Technologies) supplemented with 10% Fetal Bovine Serum (FBS, Life Technologies), 2 mM Glutamax (Life Technologies), 1× Pen/Strep (Life Technologies), interleukin-4 (IL-4, 50 ng/ml, R&D Systems) and granulocyte-macrophage colony-stimulating factor (GM-CSF, 50 ng/ml, R&D Systems) for 6 days in a 37° C., 5% $CO_2$ humidified incubator. Dendritic cells were harvested, washed with media and then activated by culturing cells in media containing lipopolysaccharide from *Escherichia coli* (LPS, 100 ng/ml, Sigma) for 24 hours in a 37° C., 5% $CO_2$ humidified incubator. Cells were harvested, washed with media, re-suspended to 400,000 cells/ml in media and plated at 10,000 cells/well/25 µl. CD4+ T cells were freshly isolated from human whole blood (Stanford blood center) of donor B using a ficoll gradient and magnetic separation (CD4+ T cell isolation kit, Miltenyi). T cells were re-susepended to 4,000,000 cells/ml in RPMI (Life Technologies) supplemented with 10% Fetal Bovine Serum (FBS, Life Technologies), 2 mM Glutamax (Life Technologies), 25 mM HEPES (Life Technologies) and 1× Pen/Strep (Life Technologies). CD4+ T cells were mixed with the dendritic cells at 100,000 cells/well/25 µl. Cells were treated with test compounds (50 µl at 20 µM, 2 µM and/or 0.2 µM) to a final concentration of 10 µM, 1 µM and/or 0.1 µM. Compounds were diluted in dimethyl sulfoxide (DMSO, Sigma) to a final concentration of 0.1%. DMSO at 0.1% was used as a vehicle control. Cells were maintained for 5 days in a 37° C., 5% $CO_2$ humidified incubator. On day 5, supernatants were collected and measured for interferon gamma (INFγ) using enzyme linked immunosorbent assay (ELISA). Percent inhibition was determined by compound inhibitory potency against IFNγ secretion compared to vehicle treated cells. Data is the average from 4 donors. Compound 1 was able to inhibit IFNγ secretion by 99%±0.4 (at 10 µM), 76%±10 (at µM) and 43%±12 (at 0.1 µM) when compared to vehicle control.

Assay 18: Inhibition of Spontaneous Periostin and IL-6 Secretion in Human 3D Airway Cultures Derived from Asthmatic Donors EpiAirway tissue cultures were obtained from Mattek (AIR-100). Cells were derived from asthmatic donors that spontaneously secrete periostin, a matricellular protein associated with Th2 mediated asthma (eosinophilic), and interleukin-6 (IL-6), an inflammatory cytokine that plays a role in both Th2 and non-Th2 related asthma. In a cell culture insert, human derived tracheal/bronchial epithelial cells were grown and differentiated on a porous membrane support, allowing an air-liquid interface with warmed culture medium below the cells and a gaseous test atmosphere above. Tissues were cultured in maintenance media (Mattek, AIR-100-MM) in a 37° C., 5% CO2 humidified incubator. Four donors were tested. On Day 0, tissue cultures were treated with test compounds in liquid interface at 10 µM, 1 µM and/or 0.1 µM. Compounds were diluted in dimethyl sulfoxide (DMSO, Sigma) to a final concentration of 0.1%. DMSO at 0.1% was used as a vehicle control. Tissue cultures were maintained for 8 days. Media was replaced every 2 days with fresh media containing compounds. On Day 8, supernatants were collected for analysis. Supernatant samples were assayed for periostin and interleukin-6 (IL-6) using luminex analysis (EMD Millipore). Data is expressed as % Inhibition+/−standard deviation (±STDV). Percent inhibition was determined by compound inhibitory potency against spontaneous secretion of periostin and IL-6 compared to vehicle treated cells. Data is the average from 3 or 4 donors. Compound 1 was able to inhibit spontaneous periostin secretion by 62%±25 (at 10 µM) and 40%±28 (at 1 µM) when compared to vehicle control. Compound 1 was able to inhibit spontaneous IL-6 secretion by 91%±9.0 (at 10 µM), 70%±33 (at 1 µM) and 10%±40 (at 0.1 µM) when compared to vehicle.

Crystal Structure

A co-crystal structure was obtained of compound C-1 bound to human JAK1 at a resolution of 2.28 Å. The ligand was observed to bind in the ATP binding site. Seven specific hydrogen bonding interactions were identified based upon a distance of 3.5 Å or less between donor and acceptor atoms. Of particular note, a hydrogen bonding interaction was identified between the carbonyl of the exocyclic amide of the compound of C-1 and the sidechain of Arg879 of JAK1. A similar interaction can be expected for the compounds of the invention. In earlier modeling studies this interaction had been proposed as a way to provide selectivity for JAK1 over other tyrosine kinases, as otherwise closely related kinases (e.g. TRKA, VEGFR, ABL1) did not possess an arginine residue at the equivalent location. The observed results of the hydrogen bonding interaction in the crystal structure and improved kinome selectivity compared to series not possessing the exocyclic amide validate this design hypothesis.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A compound of formula (I):

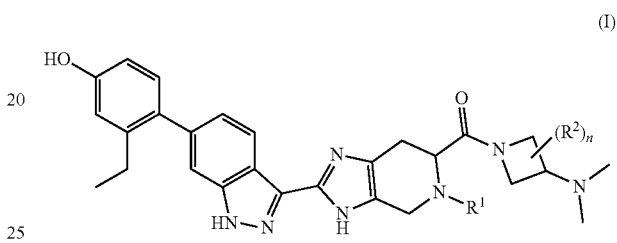

or a pharmaceutically-acceptable salt thereof
wherein:
n is 0, 1 or 2;
$R^1$ is $C_{1-3}$ alkyl; and
each $R^2$ is independently $C_{1-3}$ alkyl.

2. The compound of claim 1, or a pharmaceutically-acceptable salt thereof, having the formula (II):

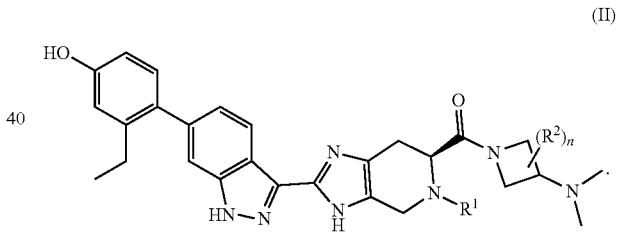

3. The compound of claim 1, or a pharmaceutically-acceptable salt thereof, having the formula (III):

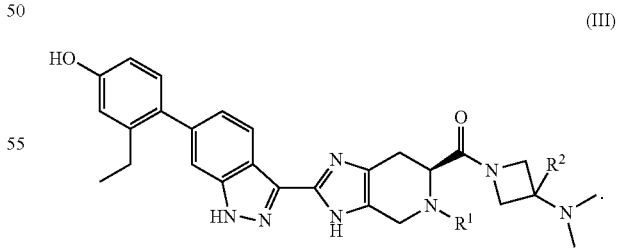

4. The compound of claim 3, or a pharmaceutically-acceptable salt thereof, wherein $R^1$ is selected from the group consisting of ethyl, propyl, and isopropyl.

5. The compound of claim 2, or a pharmaceutically-acceptable salt thereof, wherein n is 0.

6. The compound of claim 2, or a pharmaceutically-acceptable salt thereof, wherein n is 1.

7. The compound of claim 2, or a pharmaceutically-acceptable salt thereof, wherein n is 1 and $R^2$ is methyl.

8. A compound of formula 1:

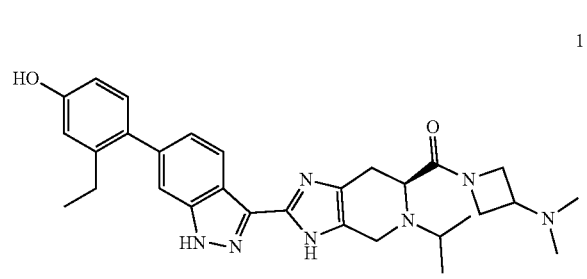 [SMILES: CCc1cc(O)ccc1-c1ccc2c(-c3nc4c([nH]3)CN(C(C)C)[C@H](C(=O)N3CC(N(C)C)C3)C4)n[nH]c2c1]

1 or a pharmaceutically-acceptable salt thereof.

9. A compound of formula 1:

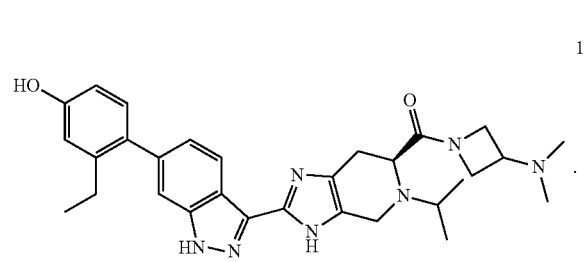 [SMILES: CCc1cc(O)ccc1-c1ccc2c(-c3nc4c([nH]3)CN(C(C)C)[C@H](C(=O)N3CC(N(C)C)C3)C4)n[nH]c2c1]

1

10. The compound of claim 1 having the formula 2:

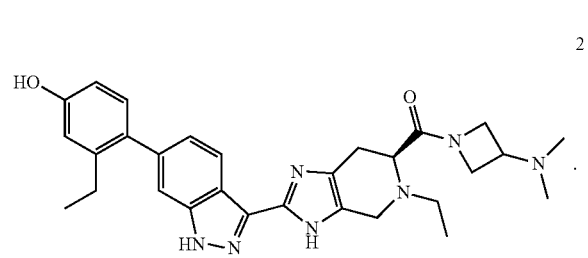 [SMILES: CCc1cc(O)ccc1-c1ccc2c(-c3nc4c([nH]3)CN(CC)[C@H](C(=O)N3CC(N(C)C)C3)C4)n[nH]c2c1]

2 or a pharmaceutically-acceptable salt thereof.

11. The compound of claim 1 having the formula 3:

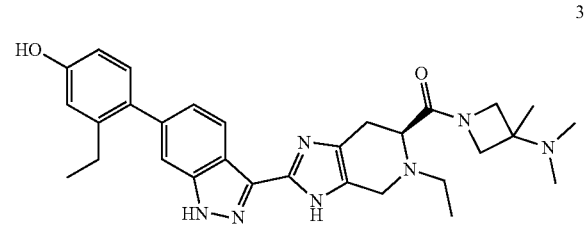 [SMILES: CCc1cc(O)ccc1-c1ccc2c(-c3nc4c([nH]3)CN(CC)[C@H](C(=O)N3CC(C)(N(C)C)C3)C4)n[nH]c2c1]

3 or a pharmaceutically-acceptable salt thereof.

12. The compound of claim 1 having the formula 4:

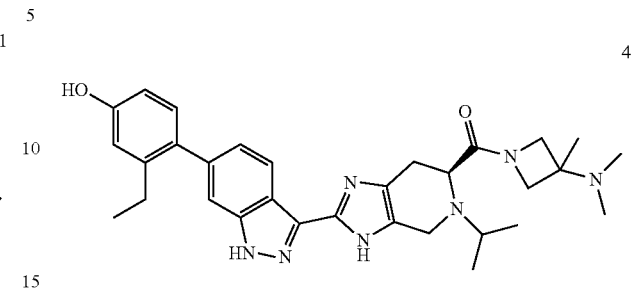

4 or a pharmaceutically-acceptable salt thereof.

13. The compound of claim 1 having the formula 5:

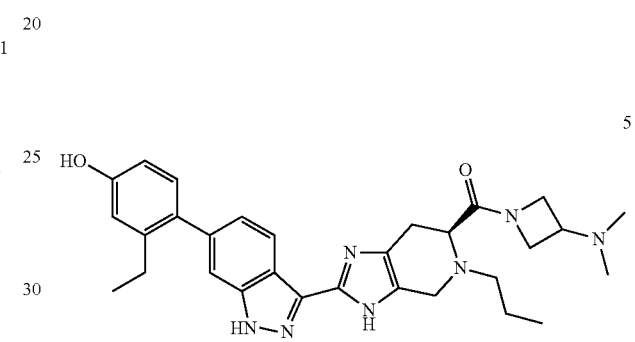

5 or a pharmaceutically-acceptable salt thereof.

14. The compound of claim 1 having the formula 6:

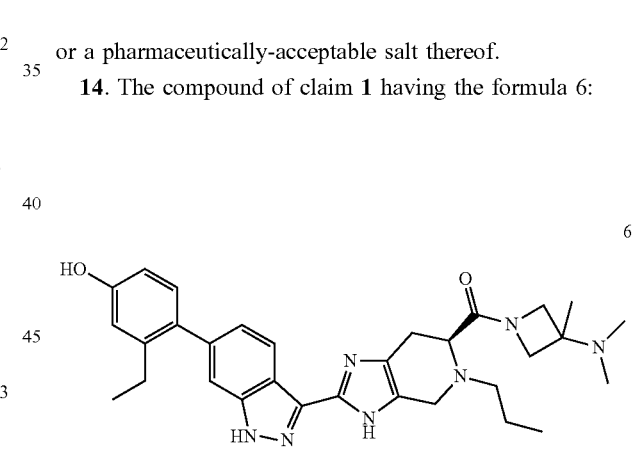

6 or a pharmaceutically-acceptable salt thereof.

15. A pharmaceutical composition comprising a compound of any one of claims 1, 2, 3 or 8, or a pharmaceutically-acceptable salt thereof, and a pharmaceutically-acceptable carrier.

* * * * *